US012775016B2

(12) United States Patent
Pehrsson et al.

(10) Patent No.: US 12,775,016 B2
(45) Date of Patent: Oct. 27, 2026

(54) BIOMARKER OF FIBROSIS

(71) Applicant: Nordic Bioscience A/S, Herlev (DK)

(72) Inventors: Martin Pehrsson, Herlev (DK); Morten Asser Karsdal, Kobenhavn Ø (DK); Diana Julie Leeming, Klampenborg (DK); Mette Juul Fisker, Kobenhavn S (DK); Tina Manon-Jensen, Brøndby (DK); Joachim Høg Mortensen, Hundige Strand (DK)

(73) Assignee: Nordic Bioscience A/S, Herlev (DK)

( * ) Notice: Subject to any disclaimer, the term of this patent is extended or adjusted under 35 U.S.C. 154(b) by 1009 days.

(21) Appl. No.: 17/919,270

(22) PCT Filed: Apr. 15, 2021

(86) PCT No.: PCT/EP2021/059759
§ 371 (c)(1),
(2) Date: Oct. 16, 2022

(87) PCT Pub. No.: WO2021/209540
PCT Pub. Date: Oct. 21, 2021

(65) Prior Publication Data

US 2024/0003906 A1 Jan. 4, 2024

(30) Foreign Application Priority Data

Apr. 16, 2020 (GB) ........................................ 2005564
Nov. 16, 2020 (GB) ........................................ 2017987

(51) Int. Cl.
*G01N 33/68* (2006.01)
*C07K 16/18* (2006.01)

(52) U.S. Cl.
CPC ......... *G01N 33/6887* (2013.01); *C07K 16/18* (2013.01); *C07K 2317/34* (2013.01); *G01N 2333/78* (2013.01); *G01N 2470/04* (2021.08); *G01N 2800/065* (2013.01); *G01N 2800/085* (2013.01); *G01N 2800/52* (2013.01); *G01N 2800/56* (2013.01); *G01N 2800/7052* (2013.01)

(58) Field of Classification Search
CPC ........... G01N 33/6887; G01N 2333/78; G01N 2470/04; G01N 2800/065; G01N 2800/085; G01N 2800/52; G01N 33/575; C07K 16/18; C07K 2317/34
See application file for complete search history.

(56) References Cited

U.S. PATENT DOCUMENTS 6,143,511 A * 11/2000 Eyre ........................ G01N 33/53 435/7.94
6,596,476 B1 * 7/2003 Lesniewski et al. .... C12Q 1/70 435/5

OTHER PUBLICATIONS

Harlow, E. and Lane, D., Antibodies: A Laboratory Manual (1988) Cold Spring Harbor Laboratory Press, Cold Spring Harbor, NY, pp. 23-26 (Year: 1988).*
Lederman et al., "A single amino acid substitution in a common African allele of the CD4 molecule ablates binding of the monoclonal antibody, OKT4" Mol Immunol. Nov. 1991;28(11):1171-81 (Year: 1991).*
Colman, Peter M. "Effects of amino acid sequence changes on antibody-antigen interactions." Research in Immunology 145.1 (1994): 33-36. (Year: 1994).*
Brown M, Rittenburg MB, Chen C, Roberts VA. Tolerance of single, but not multiple, amino acid replacements in antibody VH CDR 2: a means of minimizing B cell wastage from somatic hypermutation? J Immunol. May 1, 1996;156(9):3285-91. PMID: 8617951. (Year: 1996).*
"Enzyme-Linked Immunosorbent Assay Kit For Cross Linked C-Telopeptide Of Type III Collagen (CTXIII)" by Cloud-Clone Corp. published Jul. 2013 (Year: 2013).*
NCBI "telo-propeptide of alpha 1 (III) procollagen, partial [*Homo sapiens*]" sequence information at https://www.ncbi.nlm.nih.gov/protein/CAA25878.1 (Year: 2026).*
Haaften, W. T., et al. "Misbalance in type III collagen formation/degradation as a novel serological biomarker for penetrating (Montreal B3) Crohn's disease." Alimentary Pharmacology & Therapeutics 46.1 (2017). (Year: 2017).*

* cited by examiner

*Primary Examiner* — Bao-Thuy L Nguyen
*Assistant Examiner* — Christopher Evans
(74) *Attorney, Agent, or Firm* — Benjamin Aaron Adler

(57) ABSTRACT

The present invention relates to a sandwich immunoassay and kits for detecting in a biological sample cross-linked CTX-III, and its use in evaluating the efficacy of drugs targeting lysyl oxidases (LOXs). Cross-linked CTX-III can be used as a biomarker in diseases associated with fibrosis, including liver fibrosis, chronic intestinal disease, eosinophilic esophagitis and cancer.

19 Claims, 12 Drawing Sheets

Figure 2:
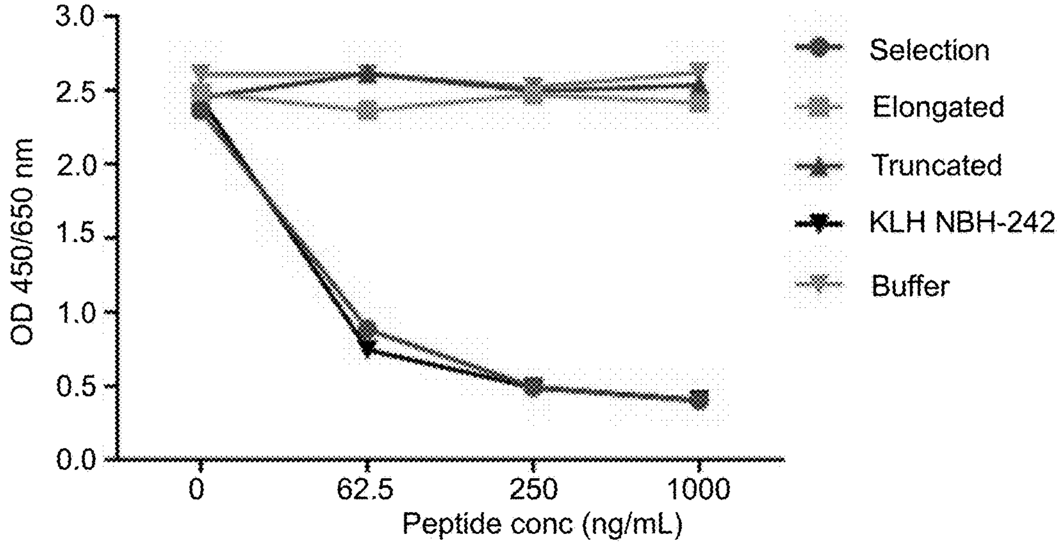

Specification includes a Sequence Listing.

```
sp|P13941|CO3A1_RAT    --GAAIAGVGGEKSGGFSPYYGDDPMDFKINTEEIMSSLKSVNGQIESLI SEQ ID NO:21
sp|P08121|CO3A1_MOUSE  G-AAAIAGVGGEKSGGFSPYYGDDPMDFKINTEEIMSSLKSVNGQIESLI SEQ ID NO:22
sp|P02461|CO3A1_HUMAN  VGAAAIAGIGGEKAGGFAPYYGDEPMDFKINTDEIMTSLKSVNGQIESLI SEQ ID NO:23
                         .*****:****:***:*****:********:***:*************
```

Figure 1

SEQUENCE LISTING

```
<160> NUMBER OF SEQ ID NOS: 23

<210> SEQ ID NO 1
<211> LENGTH: 10
<212> TYPE: PRT
<213> ORGANISM: Artificial Sequence
<220> FEATURE:
<223> OTHER INFORMATION: Synthetic C-terminal telopeptide peptide
      sequence of type III collagen against which the monoclonal
      antibody NBH-242 is raised

<400> SEQUENCE: 1

Lys Ala Gly Gly Phe Ala Pro Tyr Tyr Gly
1               5                   10


<210> SEQ ID NO 2
<211> LENGTH: 11
<212> TYPE: PRT
<213> ORGANISM: Artificial Sequence
<220> FEATURE:
<223> OTHER INFORMATION: Elongated peptide sequence
<220> FEATURE:
<221> NAME/KEY: SITE
<222> LOCATION: 11
<223> OTHER INFORMATION: X is any amino acid

<400> SEQUENCE: 2

Lys Ala Gly Gly Phe Ala Pro Tyr Tyr Gly Xaa
1               5                   10
```

<210> SEQ ID NO 3
<211> LENGTH: 12
<212> TYPE: PRT
<213> ORGANISM: Artificial Sequence
<220> FEATURE:
<223> OTHER INFORMATION: Elongated peptide sequence
<220> FEATURE:
<221> NAME/KEY: SITE
<222> LOCATION: 12
<223> OTHER INFORMATION: X is one or more amino acids of the sequence of collagen type III or X is absent

<400> SEQUENCE: 3

```
Lys Ala Gly Gly Phe Ala Pro Tyr Tyr Gly Asp Xaa
1               5                   10
```

<210> SEQ ID NO 4
<211> LENGTH: 11
<212> TYPE: PRT
<213> ORGANISM: Artificial Sequence
<220> FEATURE:
<223> OTHER INFORMATION: Elongated peptide sequence

<400> SEQUENCE: 4

```
Lys Ala Gly Gly Phe Ala Pro Tyr Tyr Gly Asp
1               5                   10
```

<210> SEQ ID NO 5
<211> LENGTH: 9
<212> TYPE: PRT
<213> ORGANISM: Artificial Sequence
<220> FEATURE:
<223> OTHER INFORMATION: Truncated peptide sequence

<400> SEQUENCE: 5

```
Lys Ala Gly Gly Phe Ala Pro Tyr Tyr
1               5
```

<210> SEQ ID NO 6
<211> LENGTH: 16
<212> TYPE: PRT
<213> ORGANISM: Artificial Sequence
<220> FEATURE:
<223> OTHER INFORMATION: Light chain complementary determining region CDR-L1 sequence

<400> SEQUENCE: 6

```
Arg Ser Ser Lys Ser Leu Leu His Ser Asn Gly Asn Thr Tyr Leu Tyr
1               5                   10                  15
```

<210> SEQ ID NO 7
<211> LENGTH: 7
<212> TYPE: PRT
<213> ORGANISM: Artificial Sequence
<220> FEATURE:
<223> OTHER INFORMATION: Light chain complementary determining region CDR-L2 sequence

<400> SEQUENCE: 7

```
Arg Met Ser Asn Leu Ala Ser
1               5
```

<210> SEQ ID NO 8
<211> LENGTH: 9
<212> TYPE: PRT
<213> ORGANISM: Artificial Sequence
<220> FEATURE:
<223> OTHER INFORMATION: Light chain complementary determining region CDR-L3 sequence

<400> SEQUENCE: 8

Met Gln His Leu Glu Phe Pro Leu Thr
1 5

<210> SEQ ID NO 9
<211> LENGTH: 5
<212> TYPE: PRT
<213> ORGANISM: Artificial Sequence
<220> FEATURE:
<223> OTHER INFORMATION: Heavy chain complementary determining region CDR-H1 sequence

<400> SEQUENCE: 9

Asp His Gly Met His
1 5

<210> SEQ ID NO 10
<211> LENGTH: 17
<212> TYPE: PRT
<213> ORGANISM: Artificial Sequence
<220> FEATURE:
<223> OTHER INFORMATION: Heavy chain complementary determining region CDR-H2 sequence

<400> SEQUENCE: 10

Val Ile Ser Thr Tyr Tyr Gly Asp Ala Thr Tyr Asn Gln Lys Phe Lys
1 5 10 15

Gly

<210> SEQ ID NO 11
<211> LENGTH: 13
<212> TYPE: PRT
<213> ORGANISM: Artificial Sequence
<220> FEATURE:
<223> OTHER INFORMATION: Heavy chain complementary determining region CDR-H3 sequence

<400> SEQUENCE: 11

Ser Met Gly Gly Asn Tyr Val Gly Thr Gly Phe Ala Tyr
1 5 10

<210> SEQ ID NO 12
<211> LENGTH: 79
<212> TYPE: PRT
<213> ORGANISM: Artificial Sequence
<220> FEATURE:
<223> OTHER INFORMATION: Light chain complementary determining regions and framework sequence

<400> SEQUENCE: 12

Arg Ser Ser Lys Ser Leu Leu His Ser Asn Gly Asn Thr Tyr Leu Tyr
1 5 10 15

Trp Phe Leu Gln Arg Pro Gly Gln Ser Pro Gln Leu Leu Ile Tyr Arg
20 25 30

Met Ser Asn Leu Ala Ser Gly Val Pro Asp Arg Phe Ser Gly Ser Gly
35 40 45

Ser Gly Thr Ala Phe Thr Leu Arg Ile Ser Arg Val Glu Ala Glu Asp
50 55 60

Val Gly Val Tyr Tyr Cys Met Gln His Leu Glu Phe Pro Leu Thr
65 70 75

<210> SEQ ID NO 13
<211> LENGTH: 81

<212> TYPE: PRT
<213> ORGANISM: Artificial Sequence
<220> FEATURE:
<223> OTHER INFORMATION: Heavy chain complementary determining regions
      and framework sequence

<400> SEQUENCE: 13

```
Asp His Gly Met His Trp Val Lys Gln Ser Gln Ala Lys Ser Leu Glu
1               5                   10                  15

Trp Ile Gly Val Ile Ser Thr Tyr Tyr Gly Asp Ala Thr Tyr Asn Gln
            20                  25                  30

Lys Phe Lys Gly Lys Ala Thr Met Thr Val Asp Lys Ser Ser Ser Thr
        35                  40                  45

Ala Tyr Met Glu Leu Ala Arg Leu Thr Ser Glu Asp Ser Ala Ile Tyr
    50                  55                  60

Tyr Cys Ala Arg Ser Met Gly Gly Asn Tyr Val Gly Thr Gly Phe Ala
65                  70                  75                  80

Tyr
```

<210> SEQ ID NO 14
<211> LENGTH: 112
<212> TYPE: PRT
<213> ORGANISM: Artificial Sequence
<220> FEATURE:
<223> OTHER INFORMATION: Light chain variable region sequence

<400> SEQUENCE: 14

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Phe Pro Leu Thr Phe Gly Ala Gly Thr Lys Leu Glu Leu Lys
            100                 105                 110
```

<210> SEQ ID NO 15
<211> LENGTH: 122
<212> TYPE: PRT
<213> ORGANISM: Artificial Sequence
<220> FEATURE:
<223> OTHER INFORMATION: Heavy chain variable region sequence

<400> SEQUENCE: 15

```
Gln Val Gln Leu Gln Gln Ser Gly Ala Glu Leu Val Arg Pro Gly Val
1               5                   10                  15

Ser Val Lys Ile Ser Cys Lys Gly Ser Gly His Thr Phe Thr Asp His
            20                  25                  30

Gly Met His Trp Val Lys Gln Ser Gln Ala Lys Ser Leu Glu Trp Ile
        35                  40                  45

Gly Val Ile Ser Thr Tyr Tyr Gly Asp Ala Thr Tyr Asn Gln Lys Phe
    50                  55                  60

Lys Gly Lys Ala Thr Met Thr Val Asp Lys Ser Ser Ser Thr Ala Tyr
```

```
65                  70                  75                  80

Met Glu Leu Ala Arg Leu Thr Ser Glu Asp Ser Ala Ile Tyr Tyr Cys
                85                  90                  95

Ala Arg Ser Met Gly Gly Asn Tyr Val Gly Thr Gly Phe Ala Tyr Trp
            100                 105                 110

Gly Gln Gly Thr Leu Val Thr Val Ser Ala
        115                 120


<210> SEQ ID NO 16
<211> LENGTH: 11
<212> TYPE: PRT
<213> ORGANISM: Artificial Sequence
<220> FEATURE:
<223> OTHER INFORMATION: Monomer selection peptide sequence of a dimeric
      peptide
<220> FEATURE:
<221> NAME/KEY: DISULFID
<222> LOCATION: 1
<223> OTHER INFORMATION: N-terminal Cys at position 1 on both monomers
      in the dimeric peptide forms the crosslik

<400> SEQUENCE: 16

Cys Lys Ala Gly Gly Phe Ala Pro Tyr Tyr Gly
1               5                   10


<210> SEQ ID NO 17
<211> LENGTH: 12
<212> TYPE: PRT
<213> ORGANISM: Artificial Sequence
<220> FEATURE:
<223> OTHER INFORMATION: Monomer elongated peptide sequence of a dimeric
      peptide
<220> FEATURE:
<221> NAME/KEY: DISULFID
<222> LOCATION: 1
<223> OTHER INFORMATION: N-terminal Cys at position 1 on both monomers
      in the dimeric peptide forms the crosslik

<400> SEQUENCE: 17

Cys Lys Ala Gly Gly Phe Ala Pro Tyr Tyr Gly Asp
1               5                   10


<210> SEQ ID NO 18
<211> LENGTH: 10
<212> TYPE: PRT
<213> ORGANISM: Artificial Sequence
<220> FEATURE:
<223> OTHER INFORMATION: Monomer truncated peptide sequence of a dimeric
      peptide
<220> FEATURE:
<221> NAME/KEY: DISULFID
<222> LOCATION: 1
<223> OTHER INFORMATION: N-terminal Cys at position 1 on both monomers
      in the dimeric peptide forms the crosslik

<400> SEQUENCE: 18

Cys Lys Ala Gly Gly Phe Ala Pro Tyr Tyr
1               5                   10


<210> SEQ ID NO 19
<211> LENGTH: 452
<212> TYPE: PRT
<213> ORGANISM: Artificial Sequence
<220> FEATURE:
<223> OTHER INFORMATION: Heavy chain sequence of monoclonal antibody
      NBH-242, mouse IgG isotype

<400> SEQUENCE: 19
```

```
Gln Val Gln Leu Gln Gln Ser Gly Ala Glu Leu Val Arg Pro Gly Val
1               5                   10                  15

Ser Val Lys Ile Ser Cys Lys Gly Ser Gly His Thr Phe Thr Asp His
            20                  25                  30

Gly Met His Trp Val Lys Gln Ser Gln Ala Lys Ser Leu Glu Trp Ile
        35                  40                  45

Gly Val Ile Ser Thr Tyr Tyr Gly Asp Ala Thr Tyr Asn Gln Lys Phe
    50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Ser Met Gly Gly Asn Tyr Val Gly Thr Gly Phe Ala Tyr Trp
            100                 105                 110

Gly Gln Gly Thr Leu Val Thr Val Ser Ala Ala Lys Thr Thr Ala Pro
        115                 120                 125

Ser Val Tyr Pro Leu Ala Pro Val Cys Gly Asp Thr Thr Gly Ser Ser
    130                 135                 140

Val Thr Leu Gly Cys Leu Val Lys Gly Tyr Phe Pro Glu Pro Val Thr
145                 150                 155                 160

Leu Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
            180                 185                 190

Thr Ser Ser Thr Trp Pro Ser Gln Ser Ile Thr Cys Asn Val Ala His
        195                 200                 205

Pro Ala Ser Ser Thr Lys Val Asp Lys Lys Ile Glu Pro Arg Gly Pro
    210                 215                 220

Thr Ile Lys Pro Cys Pro Pro Cys Lys Cys Pro Ala Pro Asn Leu Leu
225                 230                 235                 240

Gly Gly Pro Ser Val Phe Ile Phe Pro Pro Lys Ile Lys Asp Val Leu
                245                 250                 255

Met Ile Ser Leu Ser Pro Ile Val Thr Cys Val Val Val Asp Val Ser
            260                 265                 270

Glu Asp Asp Pro Asp Val Gln Ile Ser Trp Phe Val Asn Asn Val Glu
        275                 280                 285

Val His Thr Ala Gln Thr Gln Thr His Arg Glu Asp Tyr Asn Ser Thr
    290                 295                 300

Leu Arg Val Val Ser Ala Leu Pro Ile Gln His Gln Asp Trp Met Ser
305                 310                 315                 320

Gly Lys Glu Phe Lys Cys Lys Val Asn Asn Lys Asp Leu Pro Ala Pro
                325                 330                 335

Ile Glu Arg Thr Ile Ser Lys Pro Lys Gly Ser Val Arg Ala Pro Gln
            340                 345                 350

Val Tyr Val Leu Pro Pro Pro Glu Glu Glu Met Thr Lys Lys Gln Val
        355                 360                 365

Thr Leu Thr Cys Met Val Thr Asp Phe Met Pro Glu Asp Ile Tyr Val
    370                 375                 380

Glu Trp Thr Asn Asn Gly Lys Thr Glu Leu Asn Tyr Lys Asn Thr Glu
385                 390                 395                 400

Pro Val Leu Asp Ser Asp Gly Ser Tyr Phe Met Tyr Ser Lys Leu Arg
                405                 410                 415

Val Glu Lys Lys Asn Trp Val Glu Arg Asn Ser Tyr Ser Cys Ser Val
```

```
            420                 425                 430

Val His Glu Gly Leu His Asn His His Thr Thr Lys Ser Phe Ser Arg
        435                 440                 445

Thr Pro Gly Lys
    450


<210> SEQ ID NO 20
<211> LENGTH: 218
<212> TYPE: PRT
<213> ORGANISM: Artificial Sequence
<220> FEATURE:
<223> OTHER INFORMATION: Light chain sequence of monoclonal antibody
      NBH-242, mouse kappa isotype

<400> SEQUENCE: 20

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Phe Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu
    210                 215


<210> SEQ ID NO 21
<211> LENGTH: 48
<212> TYPE: PRT
<213> ORGANISM: Rattus
<220> FEATURE:
<223> OTHER INFORMATION: Type III collagen alpha1-chain sequence

<400> SEQUENCE: 21

Gly Ala Ala Ile Ala Gly Val Gly Gly Glu Lys Ser Gly Gly Phe Ser
1               5                   10                  15

Pro Tyr Tyr Gly Asp Asp Pro Met Asp Phe Lys Ile Asn Thr Glu Glu
            20                  25                  30

Ile Met Ser Ser Leu Lys Ser Val Asn Gly Gln Ile Glu Ser Leu Ile
        35                  40                  45
```

-continued

```
<210> SEQ ID NO 22
<211> LENGTH: 49
<212> TYPE: PRT
<213> ORGANISM: Mus musculus
<220> FEATURE:
<223> OTHER INFORMATION: Type III collagen alpha1-chain sequence

<400> SEQUENCE: 22

Gly Ala Ala Ala Ile Ala Gly Val Gly Gly Glu Lys Ser Gly Gly Phe
1               5                   10                  15

Ser Pro Tyr Tyr Gly Asp Asp Pro Met Asp Phe Lys Ile Asn Thr Glu
            20                  25                  30

Glu Ile Met Ser Ser Leu Lys Ser Val Asn Gly Gln Ile Glu Ser Leu
        35                  40                  45

Ile


<210> SEQ ID NO 23
<211> LENGTH: 50
<212> TYPE: PRT
<213> ORGANISM: Homo sapiens
<220> FEATURE:
<223> OTHER INFORMATION: Type III collagen alpha1-chain sequence

<400> SEQUENCE: 23

Val Gly Ala Ala Ala Ile Ala Gly Ile Gly Gly Glu Lys Ala Gly Gly
1               5                   10                  15

Phe Ala Pro Tyr Tyr Gly Asp Glu Pro Met Asp Phe Lys Ile Asn Thr
            20                  25                  30

Asp Glu Ile Met Thr Ser Leu Lys Ser Val Asn Gly Gln Ile Glu Ser
        35                  40                  45

Leu Ile
    50
```

BIOMARKER OF FIBROSIS

TECHNICAL FIELD OF THE INVENTION

The present invention relates to a sandwich immunoassay for detecting in a biological sample cross-linked CTX-III, and its use in evaluating the efficacy of drugs targeting lysyl oxidases (LOXs). The invention also relates to a kit for performing the sandwich immunoassay.

DESCRIPTION OF THE RELATED ART

Fibrotic diseases (including those listed in Table A) are a leading cause of morbidity and mortality, e.g. cirrhosis with 800,000 deaths per year worldwide.

TABLE A

Different fibrotic diseases.

| Tissue | Examples of Causes |
|---|---|
| Liver | Viral hepatitis<br>Schistosomiasis<br>Steatohepatitis (Alcoholic or non-alcoholic)<br>Autoimmune and biliary liver diseases |
| Lung | Idiopathic pulmonary fibrosis (IPF)<br>Systemic sclerosis (Scleroderma) |
| Kidney | Nephrogenic systemic fibrosis (NSF)<br>Diabetes<br>Untreated hypertension |
| Heart | Heart attack<br>Hypertension<br>Atherosclerosis<br>Restenosis |
| Eye | Macular degeneration, retinal and vitreal retinopathy |
| Skin | Systemic sclerosis and scleroderma, keloids, hypertrophic scars, burns, genetic factors<br>NFS |
| Pancreas | Autoimmune/hereditary causes |
| Intestine | Inflammatory bowel disease |
| Brain | Alzheimer's disease, |
| Bone marrow | Cancer, ageing |
| Multi-organ fibrosis | Surgical complications, chemotherapeutic drug-induced fibrosis, radiation-induced fibrosis, mechanical injuries |

A 'fibrotic disease' is any disease giving rise to fibrosis, whether as a main or a secondary symptom. Fibrosis is the end result of chronic inflammatory reactions induced by a variety of stimuli including persistent infections, autoimmune reactions, allergic responses, chemical insults, radiation, and tissue injury. Fibrosis is characterized by the accumulation and reorganization of the extracellular matrix (ECM). Despite having obvious etiological and clinical distinctions, most chronic fibrotic disorders have in common a persistent irritant that sustains the production of growth factors, proteolytic enzymes, angiogenic factors, and fibrogenic cytokines, which together stimulate the deposition of connective tissue elements, especially collagens and proteoglycans, which progressively remodel and destroy normal tissue architecture. Despite its enormous impact on human health, there are currently no approved treatments that directly target the mechanisms of fibrosis.

The role of type III collagen and its involvement in fibrosis of the liver (1), intestines (2), kidneys (3), and lungs (4) has shown altered turnover. Being one of the major fibrillary collagens produced by fibroblasts, type III collagen is also thought to be involved in the pro-fibrotic cross-linking events. Here, the excessive formation of cross-links results in a protease inaccessible matrix (5) with increased matrix stiffness (6). This consequently leads to ECM accumulation through (myo)fibroblast activation (7), differentiation (8), and migration (9) through cell:ECM interactions activating pro-fibrotic signalling cascades.

Cross-Linking of the Fibrillary Collagens

One of the final steps of collagen fibril maturation is the formation of intra- and inter-molecular cross-links catalysed by enzymes such as lysyl oxidase (LOX), lysyl oxidase like-enzymes (LOXL)s, and transglutaminases (TGs) (10). The formation of these cross-links provides both mechanical and functional properties to their respective tissue, including tensile strength 11, elasticity, as well as affecting several cellular functions (12-14). While various types of both enzymatic and non-enzymatic cross-links exist within the fibrillary collagens (collagen type I, II, III, V, IX, and XI) (10), enzymatic cross-link formation catalysed by the LOX (L)s and TGs is of interest. This is due to their involvement in both physiological and pathological cross-linking events (15,16). LOX(L)s catalyse the oxidatively deamination of specific lysines or hydroxylysines within the fibrillary collagen telopeptides leading to spontaneous cross-link formation, whereas TGs catalyse the formation of an isopeptide bond between glutamine and lysine. Though the final biochemical nature of the LOX(L) derived cross-links differ depending on their tissue expression, the cross-linking sites within the major fibrillary collagens seem to be conserved, which indicates tissue specific rather than collagen specific cross-links (10).

The importance of the physiological cross-links is evident when observing their absence in animal models, and certain genetic diseases, showing decreased tissue strength and elasticity. In addition to the detrimental effects of reduced or weakened cross-linking, excessive formation and biochemical alterations can also become detrimental to the tissue function as is observed in both tissue fibrosis and cancer. In situations of continued tissue insult, the repeated activation of the wound healing cascade results in upregulation and accumulation of fibrillar collagens such as type I and type III collagen (17), and pro-fibrotic factors including LOX(L)s and TGs. This excessive accumulation of collagens and their cross-linking enzymes mediates the formation of a stiff fibrotic extracellular matrix (ECM).

Assessment of Fibrotic Resolution

For determining the effects of the anti-fibrotic therapy, a sensitive, reliable, and optimally, a minimally invasive method of assessment is needed. As the current therapeutic options, nintedanib and pirfenidone only slows the progression as was observed in patients of idiopathic pulmonary fibrosis (18,19) or failing to provide any significant effect on skin fibrosis as was the case in a study of system sclerosis (20), the goal of completely inhibiting and reversing the fibrosis have yet to achieved. Likewise, the use of anti-inflammatory drugs may not affect the fibrosis, which is often the case with intestinal fibrosis of inflammatory bowel disease (IBD) patients (21,22) However, with the increasing knowledge and appreciation of the involvement of the fibrillar collagens and their cross-links in organ fibrosis, new potential targets have been revealed. These include small molecular inhibitors of LOXL2/3 (23) and TG2 (24), as well as inhibitors targeting the Rho kinases (25) thereby inhibiting the pro-fibrotic intracellular signalling cascades. With tissue biopsies currently being the golden standard in liver—(26) and kidney—(27) fibrosis, and other either cumbersome or invasive methods used for intestinal (28) and lung fibrosis (29), novel serological biomarkers could be applied. Presenting a crucial part of fibrosis, targeting fragments of cross-linked fibrillar collagens could potentially aid in the accurate assessment of fibrosis resolution. This was in part shown in the clinical setting of bone resorption and cartilage destruction with the application of the CTX-I (30) and CTX-II (31) biomarkers measuring degradation fragments of collagen type I and type II cross-linking, respectively. Thus, there is need to develop a novel biomarker of cross-linked type III collagen (CTX-III) as a biomarker of fibrosis resolution.

Eosinophilic Esophagitis

Eosinophilic Esophagitis (EoE) describes a food-allergen induced chronic inflammation of the esophagus characterized by a significant influx of eosinophils and Th2 cell driven inflammation. Activation of the Th2 inflammatory pathway results in recruitment of eosinophils which in turn add to the secretion of pro-inflammatory and pro-fibrotic mediators such as transforming growth factor β. With time, the sustained inflammation and secretion of pro-fibrotic mediators initiate fibroblast to myofibroblast differentiation, resulting in fibrogenesis (46-48). Myofibroblast are the principal cells in tissue fibrosis with significant secretion of collagens and cross-linking enzymes such as lysyl oxidase (LOX) and LOX-like enzymes (LOXL). Histological evaluation by Masson trichrome staining of esophageal biopsies demonstrates significant deposition of collagens in the subepithelial compartment of the lamina propria (46, 49).

Common clinical symptoms include dysphagia and food impaction in which fibrosis play an essential part as progressive fibrostenosis can result in esophageal narrowing and stricture formation. Diagnosis of EoE is primarily based on endoscopic evaluation and esophageal biopsies in patients experiencing dysphagia (50). Due to the patchy nature of EoE single biopsies are insufficient with a sensitivity of 55% (51). Therefore, a total of six biopsies are acquired increasing sensitivity to 99% (52). Endoscopies provide visual confirmation of clinical symptoms, but as up to 10% of EoE patients present with no endoscopic findings, biopsies are required for all patients. As esophageal biopsies require upper endoscopy and sedation, alternative methods such as blood-based biomarkers are being developed. The use of blood-based biomarkers is not in current regular clinical use for EoE, though several serum biomarkers have been evaluated (53,54). Thus, a medical need for minimally invasive tools such as blood-based biomarkers are needed. Similarly, to data obtained in inflammatory bowel disease (55,56), blood-based biomarkers targeting collagen metabolites reflecting either fibrogenesis or fibrolysis could be applied for EoE. These biomarkers could aid in early identification of patients with sub-clinical fibrosis not observable by endoscopy allowing for early intervention. Furthermore, degradation metabolites could reflect subepithelial inflammation or resolution of fibrosis, reflecting treatment effects. The introduction of validated blood-based biomarkers of collagen remodelling could therefore provide essential tools for evaluating deep tissue esophageal remodelling potentially limiting the need for tissue biopsies.

Additional tools include high-resolution manometry providing information of physical properties of the esophagus, with increasing pressure associated with fibrostenosis (57). Furthermore, results of brush cytology with the Cytosponge demonstrated correlation with endoscopic findings and a good sensitivity and specificity with both proximal and distal esophageal eosinophilia (58).

Inflammatory Bowel Disease

The pathological heterogenicity of inflammatory bowel disease (IBD) and especially the sub pathology of Crohn's Disease (CD) has necessitated the creation of several disease classification systems. Clinical parameters involving patient- and pathological-assessments by clinicians have resulted in determination of clinically inactive or active disease (63,64). Furthermore, the use of the Montreal classification based on endoscopy provides a visual and a more objective classification of the disease enabling stratification of patients based on endoscopic manifestations such as non-stricturing and non-penetration (B1), strictures (B2) or penetrating (B3) (65). Strictures and fistulas are two severe complications of CD characterized by either fibrostenosis, the excessive build-up of tissue especially the collagens, or severe tissue and collagen degradation resulting in transmural wounds. Representing a significant proportion of the intestinal tissue, collagens in the extracellular matrix possess important structural and signalling cues in both the healthy and inflamed intestinal tissue (66). As a result of the chronic inflammation in IBD, activated myofibroblast in the interstitial matrix deposit significant amounts of fibrillar collagen such as type I, III, and V collagen in combination with cross-linking enzymes such as LOX(L)s and TG2. This process will eventually cause an increase in matrix stiffness due to extensive collagen cross-linking propagating the fibrotic processes independently of inflammation (67). Furthermore, myofibroblast and recruited inflammatory cells produce huge amounts of ECM degrading proteases such as matrix metalloproteases (MMPs) driving collagen remodelling. Stricturing disease caused by fibrostenosis is the result of extensive deposition and cross-linking of collagens, whereas a penetrating disease is characterized by a predominance of proteolytic degradation of collagen.

Clinical parameters and endoscopy represent standardized methods in the IBD field. Questionaries for determining clinical parameters lack objectivity and proper identification of tissue manifestations. Furthermore, endoscopy, currently the golden standard, introduce patient discomfort, limited reach of the small intestine, and a lack of validated histopathological systems (68) limited in reaching areas in the small intestine often affected in CD patients. More recent techniques such as MRE is emerging as a non-invasive and high precision tool for assessing disease manifestations but does include an increased handling cost (69).

Therefore, the development of non-invasive biomarkers capable of assessing the underlying molecular processes driving the various disease manifestations especially markers reflecting intestinal fibrogenesis and resolution of intestinal fibrosis is urgently needed.

Cancer

Despite years of dedicated research, cancer remains the second leading cause of death globally. A key element in the survival of cancer patients is early diagnosis and the ability to predict response to treatment.

Similar to organ fibrosis, cancer is characterized by a pathological degree of ECM remodelling (72,73). Here, cancer and stromal cells secrete large amounts of MMPs that degrade the surrounding ECM components including collagens. In addition to ECM degradation, Cancer associated fibroblasts (CAFs) provide a significant deposition of collagens within the tumor stroma which are submitted to heavy enzymatic cross-linking by LOX(L)s, and TG2, enhancing tumor progression (74,75). This process regulates cell signalling, proliferation, differentiation, gene expression, migration, invasion, and metastasis (76,77). With CAFs leading the way, the alignment and enzymatic cross-linking of the fibrillar collagens pave the way for invading tumor cells. Furthermore, the heavily cross-linked ECM is thought to impede migration of T-cells thereby shielding tumor cells from the host immune system (78). This shielding effect could explain why certain cancer patients respond poorly to immunotherapy (78,79).

With emerging evidence underlining the important role of fibrillar collagen deposition and subsequent enzymatic cross-linking in tumor progression and treatment response, the CTX-III biomarker was investigated in a range of cancer types. CTX-III quantification and subsequent patient stratification may aid in assessing molecular processes within the tumor stroma and identify patients potentially benefitting from immunotherapy.

WO20178/34172 describes measuring cross-linked N-terminal propeptide of type III collagen (PIIINP) in a suitable sample as a marker for fibrosis. This method utilized a monoclonal antibody disclosed in WO 2014/170312. This marker is solely produced in the formation process.

The applicant has developed a highly sensitive immunoassay targeting a neo-epitope of the C-terminal telopeptide of cross-linked type III collagen generated by C-proteinases with subsequent fragment release by additional unknown proteases, capable of accurately assessing degradation of fibrotic ECM.

The direct sandwich enzyme linked immunosorbent assay (ELISA) was developed using highly specific monoclonal antibodies targeting C-terminal telopeptide neo-epitopes of cross-linked type III collagen. The assay can be used in a clinical setting as a quantitative assessment of fibrolysis.

SUMMARY

The present invention is directed to a sandwich immunoassay for detecting in a biological sample cross-linked C-terminal telopeptide III collagen (CT-III) where the cross-linked CT-III comprises at least two strands of CT-III joined together by inter-strand cross-linking. The method comprises contacting the biological sample comprising the cross-linked CT-III with a first monoclonal antibody bound to a surface, where each strand of CT-III comprised in the cross-linked CT-III has a C-terminal neo-epitope of CT-III generated by N-protease cleavage of intact type III procollagen, and adding a second monoclonal antibody. Both monoclonal antibodies are specifically reactive with the C-terminal neo-epitope of CT-III, and said neo-epitope is comprised in a C-terminal amino acid sequence KAGGFAPYYG-COOH (SEQ ID NO: 1). The method further comprises determining the amount of binding of the second monoclonal antibody.

As used herein the term "CT-III" refers to the C-terminal telopeptide of type III collagen.

The present invention also is directed to a method for evaluating the efficacy of an antagonist drug targeting lysyl oxidases (LOXs). The method comprises using the sandwich immunoassay as described herein to quantify the amount of cross-linked CT-III in at least two biological samples obtained from a subject at a first time point and at least one subsequent time point during a period of administration of the antagonist drug to the subject. A reduction in the quantity of cross-linked CT-III from the first time point to the at least one subsequent time point during the period of administration of the antagonist drug is indicative of an efficacious antagonist drug targeting LOXs.

The present invention is directed further to a kit for use in the sandwich immunoassay as described herein. The kit comprises a solid support to which is bound the first monoclonal antibody as described above and a labelled second monoclonal antibody as described herein.

The present invention also is directed to a method of identifying the fibrosis response phenotype of a patient with fibrosis, the method comprising using the sandwich immunoassay described herein to quantify the amount of cross-linked CT-III in a biofluid sample obtained from the patient, and correlating said of cross-linked CT-III with i) values associated with known fibrotic response phenotype and/or ii) a predetermined cut-off value. The method may further comprise further comprising quantifying the amount of N-terminal type III collagen propeptide (PRO-C3) present in the biofluid sample, determining the ratio of cross-linked type III collagen (CTX-III) to PRO-C3, and correlating said ratio of cross-linked type III collagen (CTX-III) to PRO-C3 with a predetermined cut-off value.

DESCRIPTION OF THE INVENTION

Accordingly, in a first aspect the present invention relates to a monoclonal antibody that specifically recognises and binds to C-terminal telopeptide neo-epitopes of cross-linked type III collagen (also referred to herein as the target peptide), the C-terminus having the amino acid sequence KAGGFAPYYG (SEQ ID NO: 1) (also referred to herein as the target sequence).

Preferably, the monoclonal antibody is a monoclonal antibody that has been raised against a synthetic peptide having the C-terminus amino acid sequence KAGGFAPYYG (SEQ ID NO: 1). The synthetic peptide used to raise the antibody may be a synthetic peptide linked at its N-terminus to a carrier protein. Exemplary carrier proteins include proteins such as, but not limited to, keyhole limpet hemocyanin (KLH). The synthetic peptide may be linked to the carrier protein via any suitable linkage, which may include one or more additional amino acid residues at the N-terminus of the peptide. The monoclonal antibody may have been raised via suitable techniques known those skilled in the art such as, but not limited to, immunizing a mouse or other mammal, isolating and fusing spleen cells from the immunized mammal with hybridoma cells, and then culturing the resultant hybridoma cells to secure monoclonal growth.

In a preferred embodiment, the monoclonal antibody does not specifically recognise or bind to a peptide having the C-terminus amino acid sequence KAGGFAPYYGX (SEQ ID NO: 2), wherein X represents any amino acid. Thus, the monoclonal antibody preferably does not specifically recognise or bind to elongated variants of the target peptide in which the target amino acid sequence has been extended at the C-terminus by one or more amino acids. Preferably, the monoclonal antibody does not substantially recognise or bind an elongated version of said C-terminal amino acid sequence which is KAGGFAPYYGDZ-COOH (SEQ ID NO: 3), wherein Z is absent or is one or more amino acids of the sequence of collagen type III. Preferably, the monoclonal antibody preferably does not specifically recognise or bind to a peptide having the C-terminus amino acid sequence KAGGFAPYYGD (SEQ ID NO: 4).

In a preferred embodiment, the monoclonal antibody does not specifically recognise or bind to a peptide having the C-terminus amino acid sequence KAGGFAPYY (SEQ ID NO: 5). Thus, the monoclonal antibody preferably does not specifically recognise or bind to shortened variants of the target peptide in which the target amino acid sequence has been truncated at the C-terminus by one or more amino acids.

Preferably, the monoclonal antibody or fragment thereof may preferably comprise one or more complementarity-determining regions (CDRs) selected from:

CDR-L1:
(SEQ ID NO: 6)
RSSKSLLHSNGNTYLY

CDR-L2:
(SEQ ID NO: 7)
RMSNLAS

CDR-L3:
(SEQ ID NO: 8)
MQHLEFPLT

CDR-H1:
(SEQ ID NO: 9)
DHGMH

CDR-H2:
(SEQ ID NO: 10)
VISTYYGDATYNQKFKG

CDR-H3:
(SEQ ID NO: 11)
SMGGNYVGTGFAY.

Preferably the antibody or fragment thereof comprises at least 2, 3, 4, 5 or 6 of the above listed CDR sequences.

Preferably the monoclonal antibody or fragment thereof has a light chain variable region comprising the CDR sequences

CDR-L1:
(SEQ ID NO: 6)
RSSKSLLHSNGNTYLY

CDR-L2:
(SEQ ID NO: 7)
RMSNLAS
and

CDR-L3:
(SEQ ID NO: 8)
MQHLEFPLT.

Preferably the monoclonal antibody or fragment thereof has a light chain that comprises framework sequences between the CDRs, wherein said framework sequences are substantially identical or substantially similar to the framework sequences between the CDRs in the light chain sequence below (in which the CDRs are shown in bold and underlined, and the framework sequences are shown in italics).

(SEQ ID NO: 12)
RSSKSLLHSNGNTYLY*WFLQRPGQSPQLLIY*RMSNLAS*GVPDRFSGSGS*
*GTAFTLRISRVEAEDVGVYYC*MQHLEFPLT

Preferably the monoclonal antibody or fragment thereof has a heavy chain variable region comprising the CDR sequences

CDR-H1:
(SEQ ID NO: 9)
DHGMH

CDR-H2:
(SEQ ID NO: 10)
VISTYYGDATYNQKFKG
and

CDR-H3:
(SEQ ID NO: 11)
SMGGNYVGTGFAY

Preferably the monoclonal antibody or fragment thereof has a heavy chain that comprises framework sequences between the CDRs, wherein said framework sequences are substantially identical or substantially similar to the framework sequences between the CDRs in the light chain sequence below (in which the CDRs are shown in bold and underlined, and the framework sequences are shown in italics).

(SEQ ID NO: 13)
DHGMH*WVKQSQAKSLEWIG*VISTYYGDATYNQKFKG*KATMTVDKSSSTA*
*YMELARLTSEDSAIYYCAR*SMGGNYVGTGFAY

As used herein, the framework amino acid sequences between the CDRs of an antibody are substantially identical or substantially similar to the framework amino acid sequences between the CDRs of another antibody if they have at least 70%, 80%, 90% or at least 95% similarity or identity. The similar or identical amino acids may be contiguous or non-contiguous.

The framework sequences may contain one or more amino acid substitutions, insertions and/or deletions. Amino acid substitutions may be conservative, by which it is meant the substituted amino acid has similar chemical properties to the original amino acid. A skilled person would understand which amino acids share similar chemical properties. For example, the following groups of amino acids share similar chemical properties such as size, charge and polarity: Group 1 Ala, Ser, Thr, Pro, Gly; Group 2 Asp, Asn, Glu, Gln; Group 3 His, Arg, Lys; Group 4 Met, Leu, Ile, Val, Cys; Group 5 Phe Thy Trp.

A program such as the CLUSTAL program to can be used to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention. Identity or similarity is preferably calculated over the entire length of the framework sequences.

In certain preferred embodiments, the monoclonal antibody or fragment thereof may comprise the light chain variable region sequence:

(SEQ ID NO: 14)
*DIVMTQAAPSVPVTPGESVSISC*RSSKSLLHSNGNTYLY*WFLQRPGQSP*
*QLLIY*RMSNLAS*GVPDRFSGSGSGTAFTLRISRVEAEDVGVYYC*MQHLE
FPLT*FGAGTKLELK*
(CDRs bold and underlined; Framework sequences in italics)

(CDRs bold and underlined; Framework sequences in italics)

and/or the heavy chain variable region sequence:

(SEQ ID NO: 15)
*QVQLQQSGAELVRPGVSVKISCKGSGHTFT*DHGMH*WVKQSQAKSLEWIG*
VISTYYGDATYNQKFKG*KATMTVDKSSSTAYMELARLTSEDSAIYYCAR*
SMGGNYVGTGFAY*WGQGTLVTVSA*
(CDRs bold and underlined; Framework sequences in italics)

The present invention relates to a sandwich immunoassay for detecting in a biological sample cross-linked C-terminal telopeptide of type III collagen (CT-III), said cross-linked CT-III comprising at least two strands of CT-III joined together by inter-strand cross-linking, said method comprising:

contacting said biological sample comprising said cross-linked CT-III with a first monoclonal antibody bound to a surface, wherein each strand of CT-III comprised in the cross-linked CT-III comprises a C-terminal neo-epitope of CT-III generated by C-proteinase cleavage of intact type III collagen;

adding a second monoclonal antibody; and determining the amount of binding of said second monoclonal antibody;

wherein both said first monoclonal antibody and said second monoclonal antibody are specifically reactive with said C-terminal neo-epitope of CT-III, said neo-epitope being comprised in a C-terminal amino acid sequence KAGGFAPYYG-COOH (SEQ ID NO: 1).

Preferably, the monoclonal antibody does not substantially recognise or bind an elongated version of said C-terminal amino acid sequence which is KAGGFAPYYGDZ-COOH (SEQ ID NO: 3), wherein Z is absent or is one or more amino acids of the sequence of collagen type III.

Preferably, the monoclonal antibody does not substantially recognise or bind a truncated version of said C-terminal amino acid sequence which is KAGGFAPYY-COOH (SEQ ID NO: 5).

The herein described sandwich immunoassay uses the same antibody as both catcher and detector antibody, therefore a double strand peptide (i.e. cross-linked) can be recognized by the assay.

Preferably, the sandwich immunoassay is used to quantify the amount of cross-linked CT-III in a biofluid, wherein said biofluid may be, but is not limited to, serum, plasma, urine, amniotic fluid, tissue supernatant or cell supernatant.

The sandwich immunoassay may be, but is not limited to, a radioimmunoassay, fluorescence immunoassay, or an enzyme-linked immunosorbent assay.

In a preferred embodiment, the second monoclonal antibody may be labeled in order to determine the amount of binding of said second monoclonal antibody.

Preferably, the second monoclonal antibody may be an enzyme-linked antibody. The enzyme may be, but is not limited to, horseradish peroxidase (HRP).

Preferably, the second monoclonal antibody may be radiolabeled or linked to a fluorophore.

Although these are preferred labels to be used with the invention, it is envisaged that any suitable labeling system may be employed, such as, but not limited to, DNA reporters or electrochemiluminescent tags.

Alternatively, a further labeled antibody which recognises the second monoclonal antibody may be used to determine the amount of binding of said second monoclonal antibody. The further labeled antibody may be labeled using a label as described above.

In a preferred embodiment of the invention, the sandwich immunoassay may further comprise correlating the quantity of cross-linked CT-III determined by said method with standard disease samples of known disease severity to evaluate the severity of a disease. The disease may be a fibrotic disease. Such a fibrotic disease may be, but is not limited to, liver disease, in particular non-alcoholic fatty liver disease (NAFLD), or viral liver fibrosis, such as HCV related liver fibrosis. Alternatively, the disease may be a chronic intestinal disease. Such a chronic intestinal disease may be, but is not limited to, Crohn's disease, or ulcerative colitis, preferably Crohn's disease. Alternatively, the disease may be a cancer. Such a cancer may be, but is not limited to, breast cancer, bladder cancer, colorectal cancer, head and neck cancer, kidney cancer, lung cancer, pancreatic cancer, stomach (gastric) cancer, ovarian cancer, liver cancer, prostate cancer, or melanoma. Preferably the cancer is breast cancer.

The sandwich immunoassay can also be used to monitor the progress of a disease by comparing the quantity of cross-linked CT-III determined by said method with the quantity of cross-linked CT-III determined in a second sample obtained from the same patient at a different time point. The second sample can be obtained several hours, days, weeks, or years before or after the sample being tested. Multiple samples can be taken at different time points, the quantity of cross-linked CT-III determined and the results compared. The sandwich immunoassay can be used to monitor the progress of a disease following treatment, to identify if the treatment has been successful. Preferably the disease is a fibrotic disease. Such a fibrotic disease may be, but is not limited to, liver disease, in particular non-alcoholic fatty liver disease (NAFLD), or viral liver fibrosis, such as HCV related liver fibrosis. Alternatively, the disease may be eosinophilic esophagitis. Alternatively, the disease may be a chronic intestinal disease. Such a chronic intestinal disease may be, but is not limited to, Crohn's disease, or ulcerative colitis, preferably Crohn's disease. Alternatively, the disease may be a cancer. Such a cancer may be, but is not limited to, breast cancer, bladder cancer, colorectal cancer, head and neck cancer, kidney cancer, lung cancer, pancreatic cancer, stomach (gastric) cancer, ovarian cancer, liver cancer, prostate cancer, or melanoma. Preferably the cancer is breast cancer.

The sandwich assay described herein may further comprise determining the amount of collagen type III formation, preferably by determining the amount of PRO-C3 present in the sample.

The ratio of PRO-C3 and crosslinked CT-III (CTX-III) can be used to determine the net deposition of type III collagen, which is significantly elevated in some disease states. Pro-C3 is produced during and is a measure of collagen formation, whereas CTX-III is produced during and is a measure of degradation. Therefore, the ratio of crosslinked CT-III (CTX-III) to PRO-C3 can be used to determine the net fibrolysis, which is significantly elevated in some disease states. For example, in patients with HCV related liver fibrosis, those with a lower Ishak score (an indicator of the severity of fibrosis) had a higher degree of net fibrolysis compared to patients with a higher Ishak score. Additionally, in patients with Crohn's disease and ulcerative colitis, those with less severe disease, i.e. non-stricturing and non-penetrating disease indicated by the Montreal classification of B1 had a higher degree of net fibrolysis compared to patients with a Montreal classification of B2. Furthermore, in patients with breast cancer, those at Stage III (an indicator of the severity of the cancer) had a higher degree of net fibrolysis compared to patients at Stage II.

In a further aspect, the sandwich immunoassay described herein may be used in a method for evaluating the efficacy of a drug targeting lysyl oxidases (LOXs), such as an antagonist drug targeting LOXs.

Accordingly, the present invention also relates to a method for evaluating the efficacy of an antagonist drug targeting lysyl oxidases (LOXs), wherein said method comprises using the sandwich immunoassay described herein to quantify the amount of cross-linked CT-III in at least two biological samples, said biological samples having been obtained from a subject at a first time point and at least one subsequent time point during a period of administration of the antagonist drug to said subject, and wherein a reduction in the quantity of cross-linked CT-III from said first time point to said at least one subsequent time point during the period of administration of the antagonist drug is indicative of an efficacious antagonist drug targeting LOXs.

Preferably, the method quantifies the efficaciousness of the antagonist drug.

Preferably, the method evaluates the efficacy of an antagonist drug targeting LOXL2.

In another aspect, the present invention relates to a kit for use in the sandwich immunoassay as described herein, the kit comprising a solid support to which is bound a first monoclonal antibody as described above; and a labelled second monoclonal antibody as described above.

In another aspect, the present invention also relates to a method of identifying the fibrosis response phenotype of a patient with fibrosis, the method comprising using the sandwich immunoassay described herein to quantify the amount of cross-linked CT-III in a biofluid sample obtained from the patient, and correlating said of cross-linked CT-III with i) values associated with known fibrotic response phenotype and/or ii) a predetermined cut-off value. The method may further comprise further comprising quantifying the amount of PRO-C3 present in the biofluid sample, determining the ratio of cross-linked type III collagen (CTX-III) to PRO-C3, and correlating said ratio of cross-linked type III collagen (CTX-III) to PRO-C3 with a predetermined cut-off value.

The quantity of cross-linked CT-III determined can be compared to a pre-determined cut-off value. The predetermined cut-off value is preferably at least 3.5 ng/mL, more preferably at least 3.8 ng/mL, even more preferably at least 4.0 ng/mL, even more preferably at least 4.2 ng/mL, and most preferably at least 4.5 ng/mL. In this regard, through the combined use of various statistical analyses it has been found that a measured amount of binding between the monoclonal antibody (described above) and the C-terminus CTX-III biomarker of at least 3.5 ng/mL or greater may be determinative of the patient who has a “spontaneous regressive” phenotype. By having a statistical cutoff value of at least 3.5 ng/mL, more preferably at least 3.8 ng/mL, even more preferably at least 4.0 ng/mL, even more preferably at least 4.2 ng/mL, and most preferably at least 4.5 ng/mL, it is possible to utilise the method of the invention to identify patients who have a spontaneous regressive phenotype, with a high level of confidence.

The ratio of cross-linked type III collagen (CTX-III) and type III collagen (PRO-C3) measured in a sample can be compared to a pre-determined cut-off value. The predetermined cut-off value is preferably at least 0.5, more preferably at least 0.6, even more preferably at least 0.75, even more preferably at least 0.8, and most preferably at least 0.9. In this regard, through the combined use of various statistical analyses it has been found that a ratio of cross-linked type III collagen (CTX-III) and type III collagen (PRO-C3) of at least 0.5 or greater may be determinative of the patient who have a spontaneous regressive phenotype. By having a statistical cutoff ratio value of preferably at least 0.5, more preferably at least 0.6, even more preferably at least 0.75, even more preferably at least 0.8, and most preferably at least 0.9, it is possible to utilise the method of the invention to identify patients who have a spontaneous regressive phenotype with a high level of confidence.

In another aspect, the present invention also relates to a method of identifying a patient with a fibrotic disease, the method comprising using the sandwich immunoassay described herein to quantify the amount of cross-linked CT-III in a biofluid sample obtained from the patient, and correlating said amount of cross-linked CT-III with i) values associated with known fibrotic disease patients and/or normal healthy controls and/or ii) a predetermined cut-off value. The method may further comprise further comprising quantifying the amount of PRO-C3 present in the biofluid sample, determining the ratio of cross-linked type III collagen (CTX-III) to PRO-C3, and correlating said ratio of cross-linked type III collagen (CTX-III) to PRO-C3 with i) values associated with known fibrotic disease patients and/or normal healthy controls and/or ii) a predetermined cut-off value. An elevated level of cross-linked CT-III or a significantly different ratio compared to normal healthy controls is indicative of a fibrotic disease.

The fibrotic disease may be selected from, but not limited to liver disease, in particular non-alcoholic fatty liver disease (NAFLD), or viral liver fibrosis, such as HCV related liver fibrosis.

In another aspect, the present invention also relates to a method of identifying a patient with eosinophilic esophagitis, the method comprising using the sandwich immunoassay described herein to quantify the amount of cross-linked CT-III in a biofluid sample obtained from the patient, and correlating said amount of cross-linked CT-III with i) values associated with known eosinophilic esophagitis patients and/or normal healthy controls and/or ii) a predetermined cut-off value. The method may further comprise further comprising quantifying the amount of PRO-C3 present in the biofluid sample, determining the ratio of cross-linked type III collagen (CTX-III) to PRO-C3, and correlating said ratio of cross-linked type III collagen (CTX-III) to PRO-C3 with i) values associated with known eosinophilic esophagitis patients and/or normal healthy controls and/or ii) a predetermined cut-off value. An elevated level of cross-linked CT-III or a significantly different ratio compared to normal healthy controls is indicative of eosinophilic esophagitis.

In another aspect, the present invention also relates to a method of identifying a patient with chronic intestinal disease, the method comprising using the sandwich immunoassay described herein to quantify the amount of cross-linked CT-III in a biofluid sample obtained from the patient, and correlating said amount of cross-linked CT-III with i) values associated with known patients with chronic intestinal disease and/or normal healthy controls and/or ii) a predetermined cut-off value. The method may further comprise further comprising quantifying the amount of PRO-C3 present in the biofluid sample, determining the ratio of cross-linked type III collagen (CTX-III) to PRO-C3, and correlating said ratio of cross-linked type III collagen (CTX-III) to PRO-C3 with i) values associated with known patients with chronic intestinal disease and/or normal healthy controls and/or ii) a predetermined cut-off value. An elevated level of cross-linked CT-III or a significantly different ratio compared to normal healthy controls is indicative of the presence of a chronic intestinal disease.

The chronic intestinal disease may be selected from, but not limited an irritable bowel disease, such as Crohn’s disease, or ulcerative colitis. Preferably the chronic intestinal disease is Crohn’s disease or ulcerative colitis, more preferably Crohn’s disease.

In another aspect, the present invention also relates to a method of identifying a patient with cancer, the method comprising using the sandwich immunoassay described herein to quantify the amount of cross-linked CT-III in a biofluid sample obtained from the patient, and correlating said amount of cross-linked CT-III with i) values associated with known cancer patients and/or normal healthy controls and/or ii) a predetermined cut-off value. The method may further comprise further comprising quantifying the amount of PRO-C3 present in the biofluid sample, determining the ratio of cross-linked type III collagen (CTX-III) to PRO-C3, and correlating said ratio of cross-linked type III collagen (CTX-III) to PRO-C3 with i) values associated with known cancer patients and/or normal healthy controls and/or ii) a predetermined cut-off value. An elevated level of cross-linked CT-III or a significantly different ratio compared to normal healthy controls is indicative of the presence of a cancer.

The cancer may be selected from, but not limited to breast cancer, bladder cancer, colorectal cancer, head and neck cancer, kidney cancer, lung cancer, pancreatic cancer, stomach (gastric) cancer, ovarian cancer, liver cancer, prostate cancer, or melanoma. Preferably the cancer is breast cancer.

In another aspect the present invention provides a method of identifying a patient who would benefit from treatment, the method comprising using the sandwich immunoassay described herein to quantify the amount of cross-linked CT-III in a biofluid sample obtained from the patient, and correlating said amount of cross-linked CT-III with i) values associated with known disease patients and/or normal healthy controls and/or ii) a predetermined cut-off value. The method may further comprise further comprising quantifying the amount of PRO-C3 present in the biofluid sample, determining the ratio of cross-linked type III collagen (CTX-III) to PRO-C3, and correlating said ratio of cross-linked type III collagen (CTX-III) to PRO-C3 with i) values associated with known disease patients and/or normal healthy controls and/or ii) a predetermined cut-off value. An elevated level of cross-linked CT-III or a significantly different ratio compared to normal healthy controls is indicative of the need for treatment.

The method may further comprise administering the treatment to the patient.

The treatment is preferably administration of a medicament which targets collagen cross-linking, such as an antagonist drug targeting lysyl oxidases (LOXs).

The disease may be a fibrotic disease. Such a fibrotic disease may be, but is not limited to, liver disease, in particular non-alcoholic fatty liver disease (NAFLD), or viral liver fibrosis, such as HCV related liver fibrosis. Alternatively, the disease may be eosinophilic esophagitis. Alternatively, the disease may be a chronic intestinal disease. Such a chronic intestinal disease may be, but is not limited to, irritable bowel syndrome, such as Crohn's disease, or ulcerative colitis. Alternatively, the disease may be a cancer. Such a cancer may be, but is not limited to, breast cancer, bladder cancer, colorectal cancer, head and neck cancer, kidney cancer, lung cancer, pancreatic cancer, stomach (gastric) cancer, ovarian cancer, liver cancer, prostate cancer, or melanoma. Preferably the cancer is breast cancer.

Applying the statistical cut-off value to the method of the invention is particularly advantageous as it results in a standalone diagnostic assay; i.e. it removes the need for any direct comparisons with healthy individuals and/or patients with known disease severity in order to arrive at a diagnostic conclusion. This may also be particularly advantageous when utilising the assay to evaluate patients that already have medical signs or symptoms that are generally indicative of fibrosis, (e.g. as determined by a physical examination and/or consultation with a medical professional) as it may act as a quick and definitive tool for corroborating the initial prognosis and thus potentially remove the need for more invasive procedures, such as endoscopy or biopsy, and expedite the commencement of a suitable treatment regimen. Preferably, the predetermined cut-off value corresponds to the cut-off value as measured in human blood, serum or plasma.

Definitions

As used herein the term "neo-epitope" refers to an N- or C-terminal peptide sequence at the extremity of a polypeptide, i.e. at the N- or C-terminal end of the of the polypeptide, and is not to be construed as meaning in the general direction thereof.

As used herein the term, the monoclonal antibody NBH-242 refers to a neo-epitope specific antibody directed towards the C-terminal neo-epitope located in the C-terminal telopeptide of type III collagen (CT-III), said neo-epitope comprising the C-terminal sequence KAGGFAPYYG-COOH (SEQ ID NO: 1).

As used herein the term "PRO-C3" refers to N-terminal propeptide of type III collagen.

As used herein the term "PCX3" refers to crosslinked N-terminal propeptide of type III collagen.

As used herein the term "PRO-C3 assay" refers to the competitive ELISA for detecting and quantifying neo-epitope in the N-terminal propeptide previously described (32).

As used herein the term "PCX3 assay" refers to the competitive ELISA for detecting and quantifying the cross-linked N-terminal propeptide previously described in WO2017/134172.

As used herein the term "CT-III" refers to the C-terminal telopeptide of type III collagen.

As used herein the term "CTX-III" refers to crosslinked C-terminal telopeptide of type III collagen comprising at least two strands of CT-III joined together by inter-strand cross-linking.

As used herein the term "CTX-III" assay refers to the herein described sandwich assay for detecting and quantifying crosslinked a C-terminal telopeptide neo-epitope of cross-linked type III collagen i.e. crosslinked CT-III.

As used herein, the terms "peptide" and "polypeptide" are used synonymously.

As used herein the term "monoclonal antibody" refers to both whole antibodies and to fragments thereof that retain the binding specificity of the whole antibody, such as for example a Fab fragment, Fv fragment, or other such fragments known to those skilled in the art. Antibodies which retain the same binding specificity may contain the same complementarity-determining regions (CDR). The CDR of an antibody can be determined using methods known in the art such as that described by Kabat et al. (45).

Antibodies can be generated from B cell clones as described in the examples. The isotype of the antibody can be determined by ELISA specific for human IgM, IgG or IgA isotype, or human IgG1, IgG2, IgG3 or IgG4 subclasses. Other suitable methods can be used to identify the isotype.

The amino acid sequence of the antibodies generated can be determined using standard techniques. For example, RNA can be isolated from the cells, and used to generate cDNA by reverse transcription. The cDNA is then subjected to PCR using primers which amplify the heavy and light chains of the antibody. For example, primers specific for the leader sequence for all VH (variable heavy chain) sequences can be used together with primers that bind to a sequence located in the constant region of the isotype which has been previously determined. The light chain can be amplified using primers which bind to the 3' end of the Kappa or Lambda chain together with primers which anneal to the V kappa or V lambda leader sequence. The full length heavy and light chains can be generated and sequenced.

As used herein the term "C-terminus" refers to the extremity of a polypeptide, i.e. at the C-terminal end of the polypeptide, and is not to be construed as meaning in the general direction thereof. Likewise, the term "N-terminus" refers to the extremity of a polypeptide, i.e. at the N-terminal end of the polypeptide, and is not to be construed as meaning in the general direction thereof.

As used herein the term, the term "competitive immunoassay" refers to an immunoassay in which the target peptide present in a sample (if any) competes with known amount of target of peptide (which, for example, is bound to a fixed substrate or is labelled) for binding to an antibody, which is a technique known to those skilled in the art.

As used herein the term "ELISA" (enzyme-linked immunosorbent assay) refers to an immunoassay in which the target peptide present in a sample (if any) is detected using antibodies linked to an enzyme, such as horseradish peroxidase or alkaline phosphatase. The activity of the enzyme is then assessed by incubation with a substrate generating a measurable product. The presence and/or amount of target peptide in a sample can thereby be detected and/or quantified. ELISA is a technique known to those skilled in the art.

As used herein the term "sandwich immunoassay" refers to the use of at least two antibodies for the detection of an antigen in a sample, and is a technique known to the person skilled in the art.

As used herein the term "amount of binding" refers to the quantification of binding between monoclonal antibody and target peptide, which said quantification is determined by comparing the measured values of target peptide in the biofluid samples against a calibration curve, wherein the calibration curve is produced using standard samples of known concentration of the target peptide. In the specific assay disclosed herein which measures in biofluids target peptides having the C-terminus amino acid sequence KAGGFAPYYG (SEQ ID NO: 1), the calibration curve is produced using standard samples of known concentration of a calibration peptide having the C-terminus amino acid sequence KAGGFAPYYG (SEQ ID NO: 1) (and which may in particular consist of the amino acid sequence KAGGFAPYYG (SEQ ID NO: 1)). The values measured in the biofluid samples are compared to the calibration curve to determine the actual quantity of target peptide in the sample.

As used herein, the "cut-off value" means an amount of binding or level of fibrolysis that is determined statistically to be indicative of a high likelihood of a fibrotic disease, such as liver fibrosis, in a patient, in that a measured value of biomarker in a patient sample that is at or above the statistical cut-off value corresponds to at least a 70% probability, preferably at least an 80% probability, preferably at least an 85% probability, more preferably at least a 90% probability, and most preferably at least a 95% probability of the presence or likelihood of a fibrotic disease, such as liver fibrosis. A "cut-off value" can also means an amount of binding or level of fibrolysis that is determined statistically to be indicative of a high likelihood of a patient having a spontaneous regression phenotype.

As used herein, a "fibrosis response phenotype" refers to the phenotype of a patient which indicates how the severity of the fibrosis will change without treatment. Patients who have a "spontaneous regressive" phenotype are those who have a reduced Ishak score after 52 weeks of treatment with a placebo. Patients who have undergo no change in Ishak score after 52 weeks of treatment with a placebo have a "stable" phenotype, while those who have an increased Ishak score after 52 weeks of treatment with a placebo have a "progressive" phenotype. Patients with a "spontaneous regressive" phenotype may require a different treatment regime i.e. lower dosage or shorter treatment cycle compared to those with a stable or progressive phenotype.

As used herein the term "values associated with normal healthy subjects and/or values associated with known disease severity" means standardised quantities of cross-linked type III collagen (CTX-III) or standardised ratio of cross-linked type III collagen (CTX-III) to N-terminal propeptide of type III collagen (PRO-C3) determined by the method described supra for subjects considered to be healthy, i.e. without a disease (e.g. without fibrotic disease, such as liver disease, in particular non-alcoholic fatty liver disease (NAFLD), or viral liver fibrosis, such as HCV related liver fibrosis; chronic intestinal disease such as Crohn's disease, or ulcerative colitis; cancer, such as breast cancer, bladder cancer, colorectal cancer, head and neck cancer, kidney cancer, lung cancer, pancreatic cancer, stomach (gastric) cancer, ovarian cancer, liver cancer, prostate cancer, or melanoma), and/or standardised quantities of cross-linked type III collagen (CTX-III) or standardised ratio of cross-linked type III collagen (CTX-III) to N-terminal propeptide of type III collagen (PRO-C3) determined by the method described supra for subjects known to have a disease (e.g. fibrotic disease, such as liver disease, in particular non-alcoholic fatty liver disease (NAFLD), or viral liver fibrosis, such as HCV related liver fibrosis; chronic intestinal disease such as Crohn's disease, or ulcerative colitis; cancer, such as breast cancer, bladder cancer, colorectal cancer, head and neck cancer, kidney cancer, lung cancer, pancreatic cancer, stomach (gastric) cancer, ovarian cancer, liver cancer, prostate cancer, or melanoma), of a known severity.

As used herein, a "fibrotic disease", refers such as liver disease, in particular non-alcoholic fatty liver disease (NAFLD), or viral liver fibrosis, such as HCV related liver fibrosis.

As used herein, a "chronic intestinal disease" may be selected from, but not limited an irritable bowel disease, such as Crohn's disease, or ulcerative colitis; Preferably the chronic intestinal disease is Crohn's disease or ulcerative colitis, more preferably Crohn's disease.

As used herein, a "cancer" may be selected from, but not limited to breast cancer, bladder cancer, colorectal cancer, head and neck cancer, kidney cancer, lung cancer, pancreatic cancer, stomach (gastric) cancer, ovarian cancer, liver cancer, prostate cancer, or melanoma. Preferably the cancer is breast cancer.

FIGURES

The invention will be demonstrated in the examples below which refer to the following figures:

FIG. 1: Sequence alignment of the type III collagen α1-chain between rat (top), mouse (middle), and human (bottom) sequence. The red box frames the target sequence of neo-epitope in CT-III. The alignment was made using the corresponding species sequences from uniprot.org and the CLUSTALW 2.1 multiple alignment tool.

FIG. 2: Final inhibition of the monoclonal NBH-242 antibody in an indirect competitive ELISA. The antibody specificity was tested against the selection peptide, elongated peptide, truncated peptide, immunogenic peptide, and the buffer.

Figure 3:
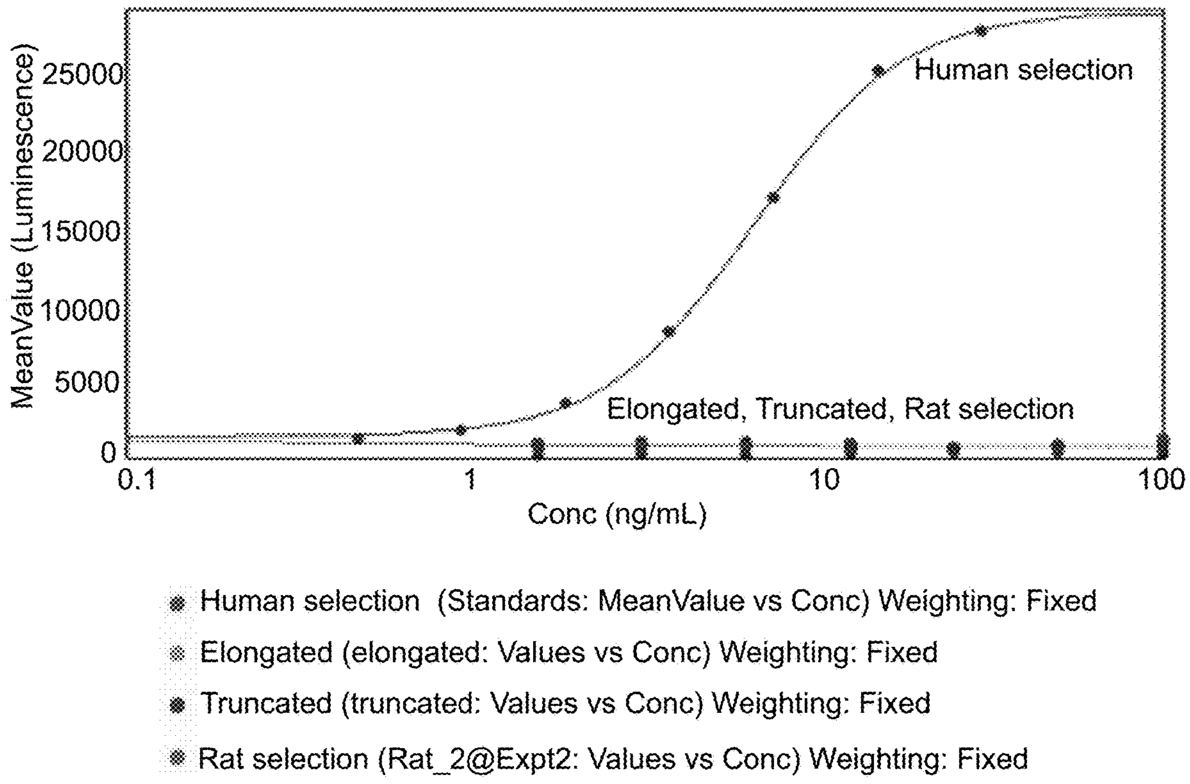

FIG. 3: Depicts a 4-parameter logistical model of antibody specificity towards the human selection peptide, the elongated peptide, the truncated peptide, and the rat selection peptide.

Figure 4:
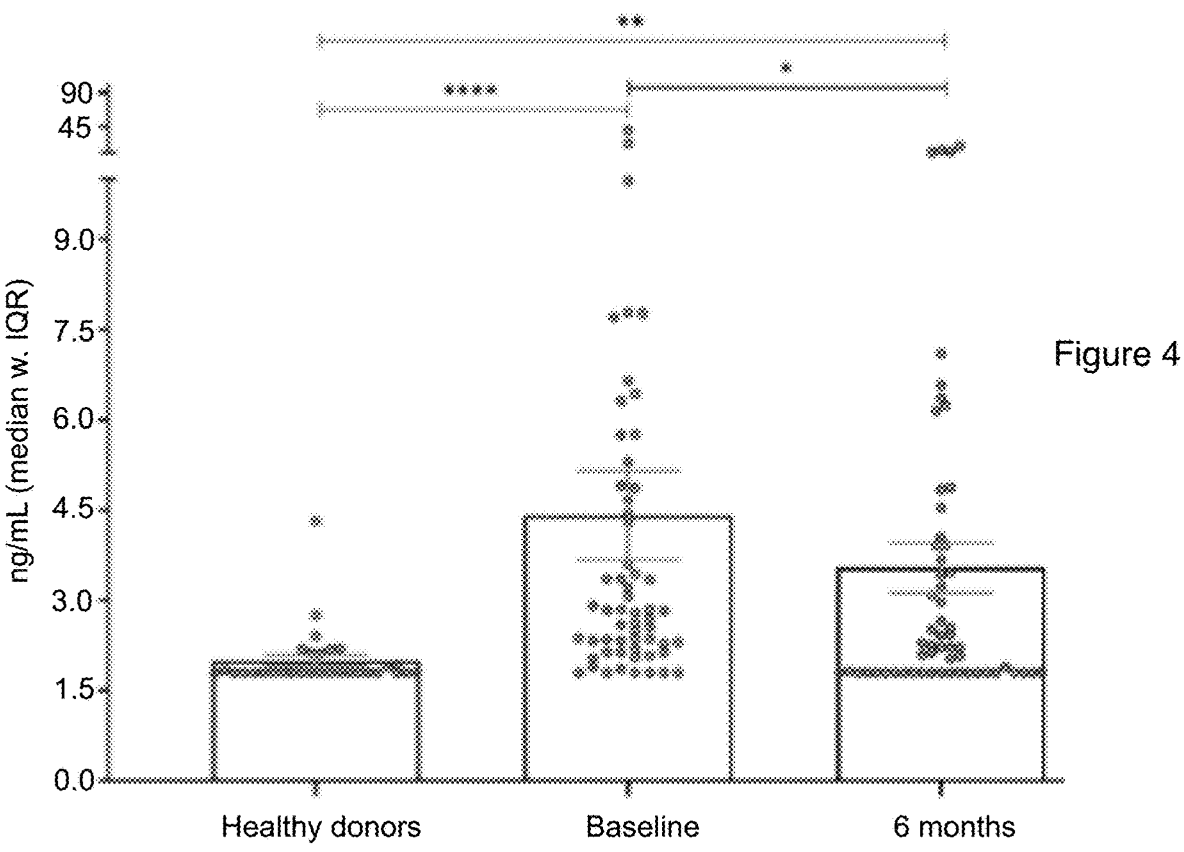

FIG. 4: Depicts the CTX-III levels of the healthy human plasma EDTA donors, and the bariatric surgery patients at baseline and 6 months follow-up. Levels below LLMR was defined as the LLMR level (1.8 ng/mL). Asterisks indicate the following: *: p<0.05; : p<0.01; *: p<0.001; ****: p<0.0001.

Figure 5:
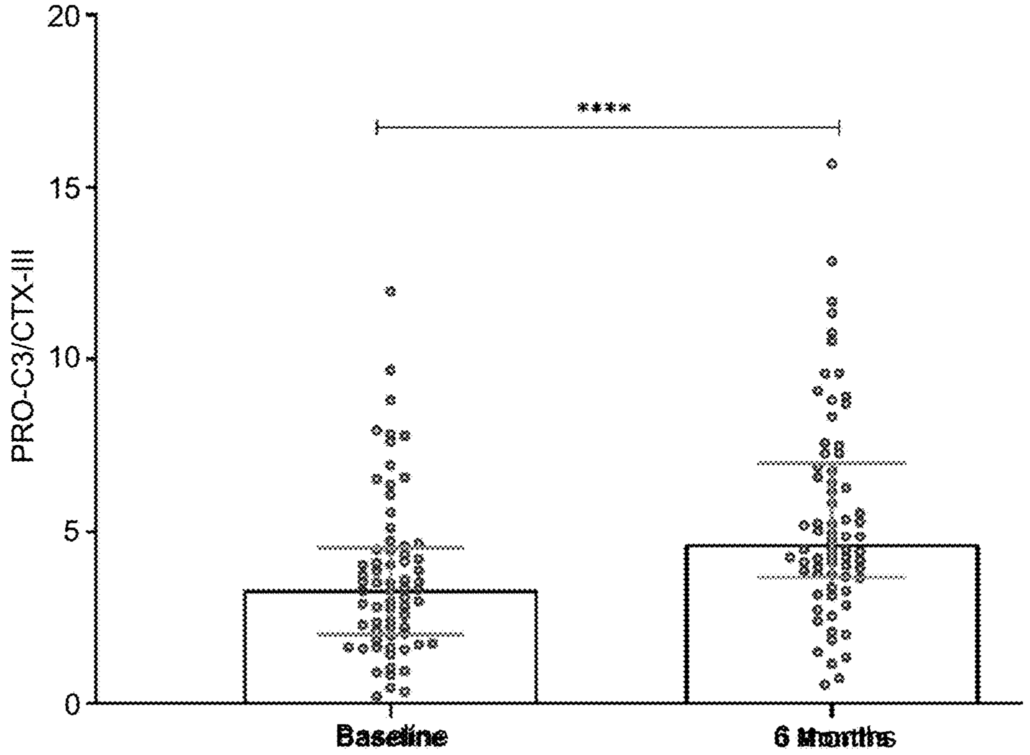

FIG. 5: Represents the net deposition of type III collagen as the ratio between the biomarker levels of PRO-C3 (type III collagen formation) and CTX-III (cross-linked type III collagen degradation) at baseline and 6 months follow-up. Asterisks indicate the following: ****: p<0.0001.

Figure 6:
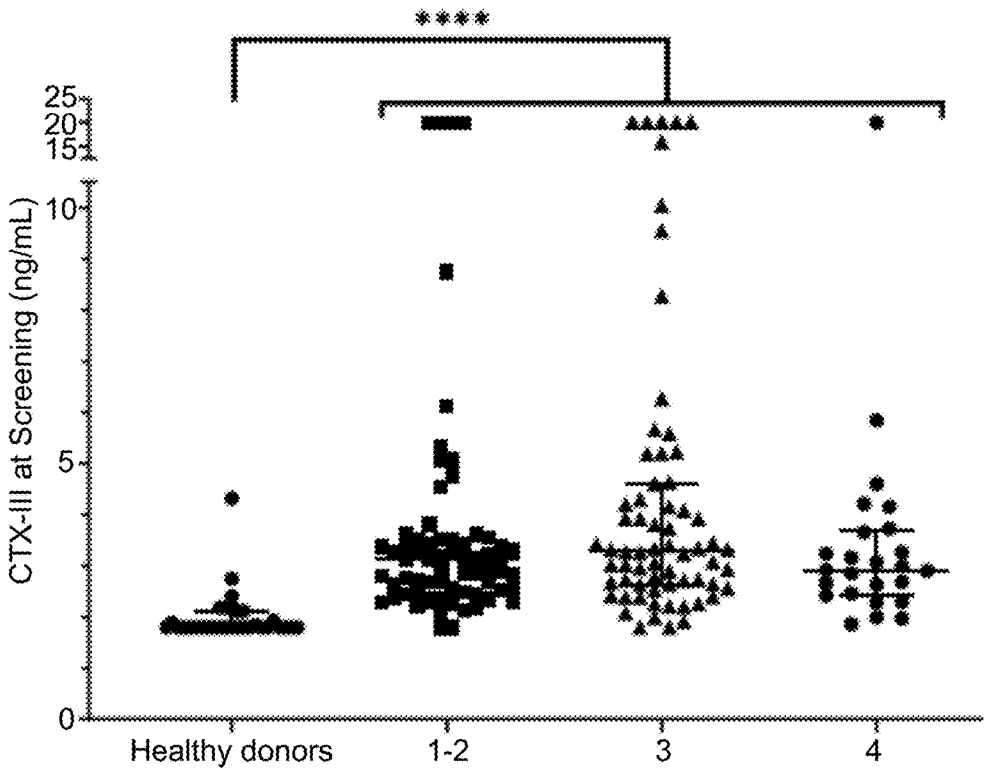

FIG. 6. Depicts Patients with HCV related liver fibrosis was stratified according to their Ishak score (1-2, 3, and 4-5) and their CTX-III levels at screening plotted against CTX-III levels of healthy donors. Data plotted as median+IQR and significance depicted as: p<0.0001****

Figure 7:
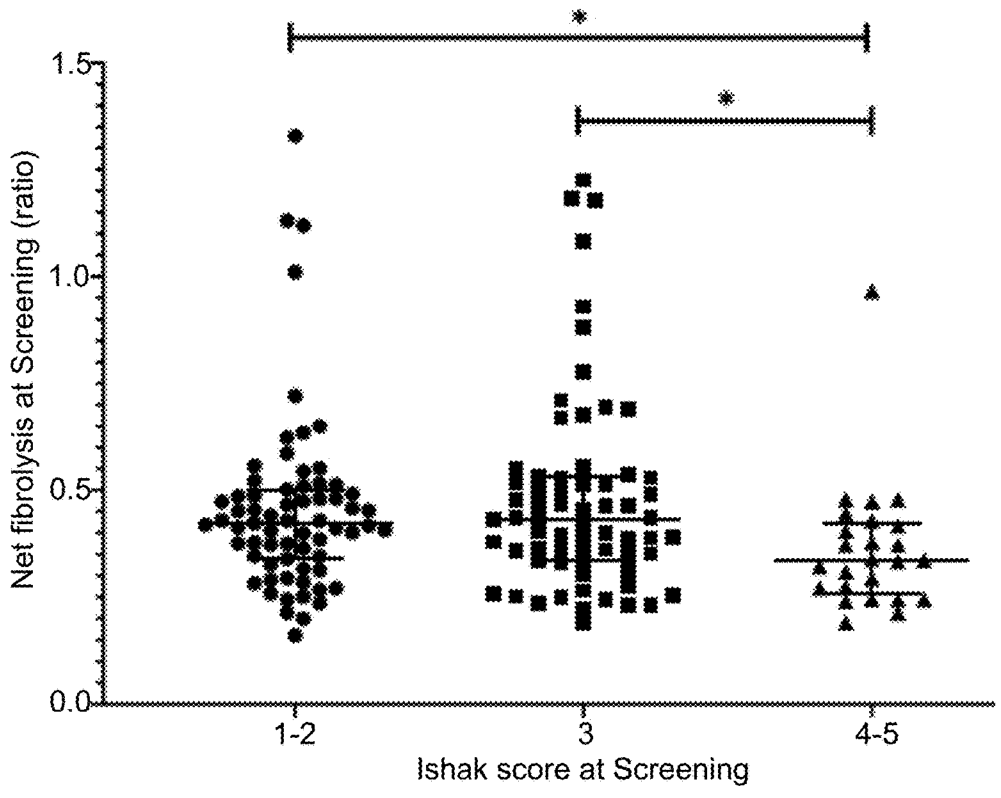

FIG. 7: Depicts levels of net fibrolysis of patients divided according to their Ishak score; 1-2, 3, and 4-5. Data plotted as median+IQR and significance depicted as: p<0.05*

Figure 8A:
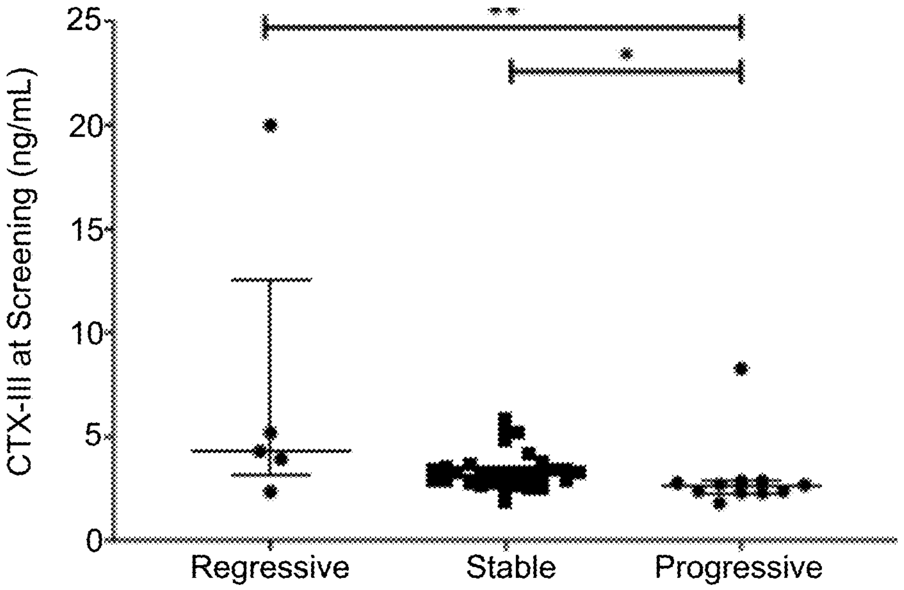
Figure 8B:
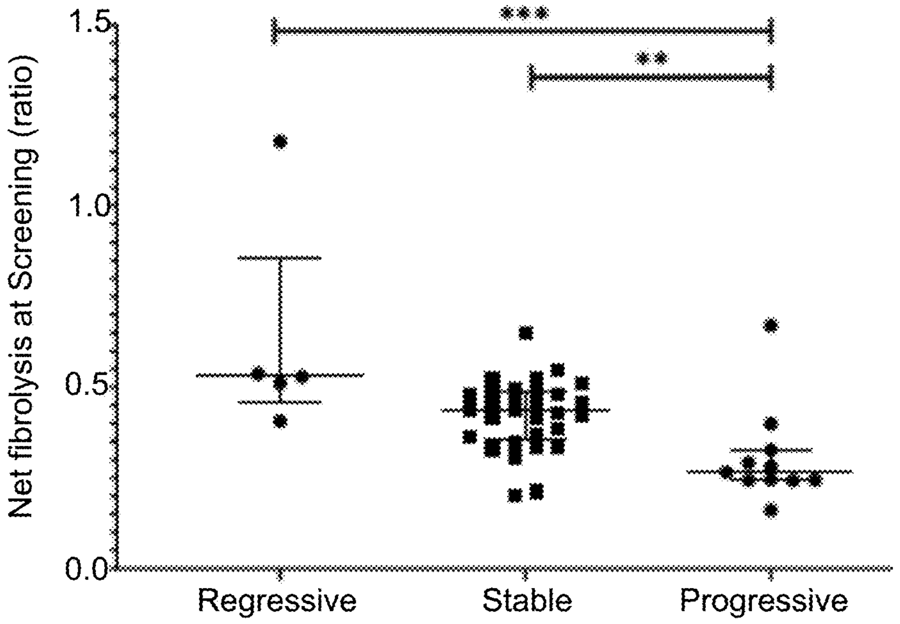

FIGS. 8A-8B: show CTX-III (FIG. 8A) or net fibrolysis (FIG. 8B) levels at screening of patients within the placebo group stratified according to their spontaneous fibrotic phenotype; Regressive, Stable, or Progressive. Data plotted with median+IQR and significance depicted as: p<0.05*, p<0.01 , and p<0.001 *

Figure 9A:
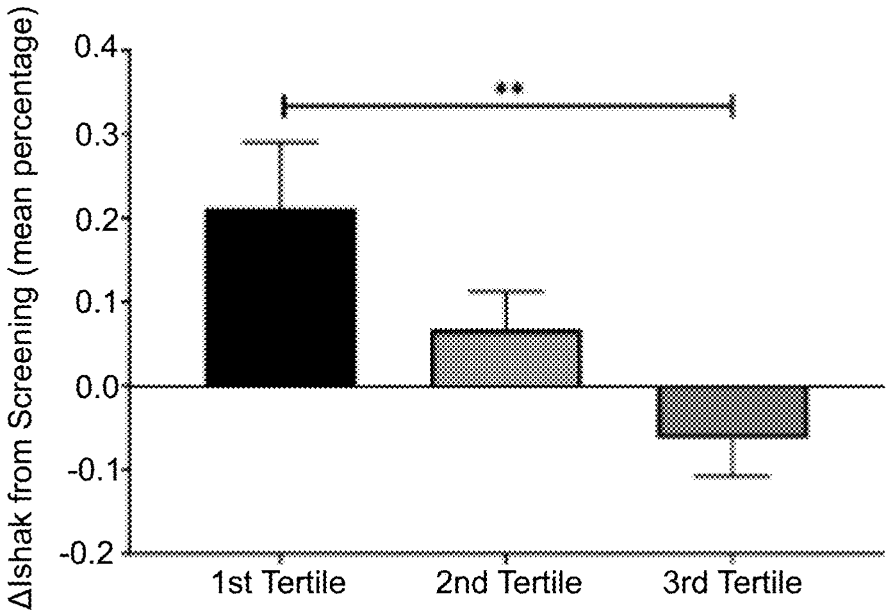
Figure 9B:
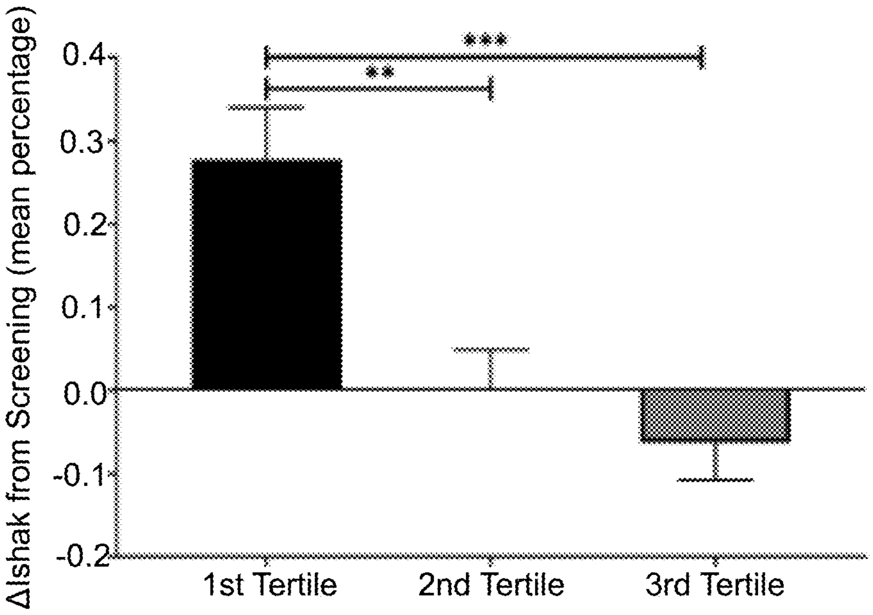

FIGS. 9A-9B: Depict the percentage change of patient Ishak score based on their CTX-III (FIG. 9A) or net fibrolysis (FIG. 9B) levels at screening by dividing patients into tertiles from lowest to highest levels (1st-, 2nd-, and 3rd-tertile). Data plotted as mean+SEM and significance depicted as: p<0.01 , and p<0.001 *

Figure 10A:
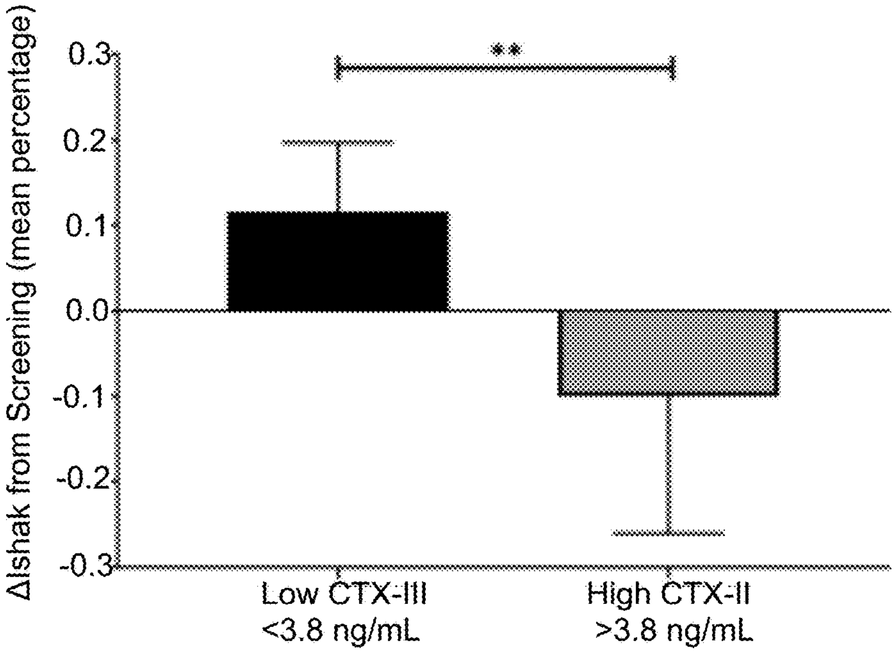
Figure 10B:
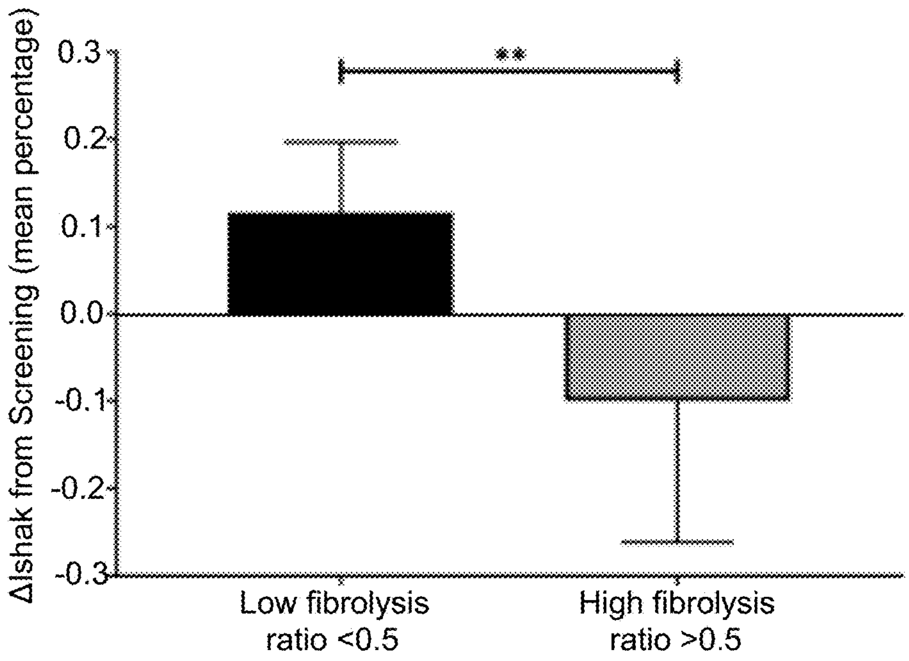

FIGS. 10A-10B: show the mean percentage change of patient Ishak score based on CTX-III (FIG. 10A) or net fibrolysis (FIG. 10B) levels at screening utilizing a cut-off level calculated by the Youden index. Data plotted as mean+SEM and significance depicted as: p<0.01 **

Figure 11:
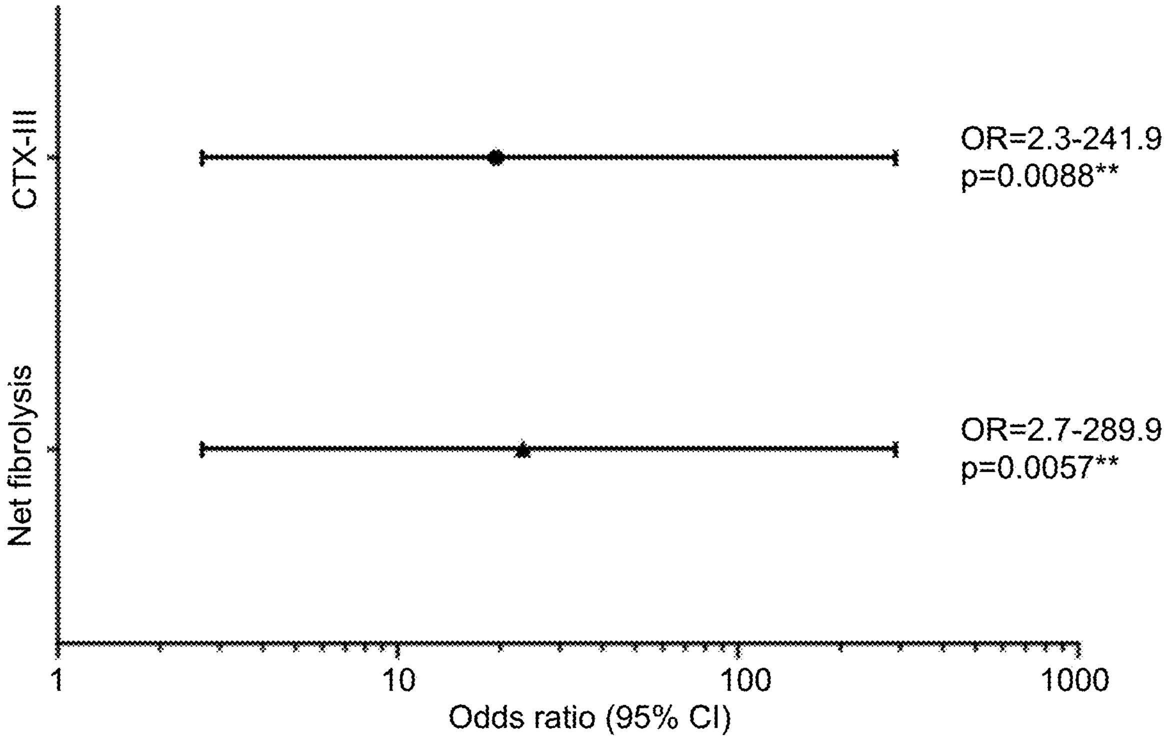

FIG. 11: Depicts the odds ratio for being presenting with a regressive fibrotic phenotype based on Youden index determined levels of CTX-III or net fibrolysis at screening. Odds ratio plotted with 95% CI and significance depicted as: p<0.01**

Figure 12:
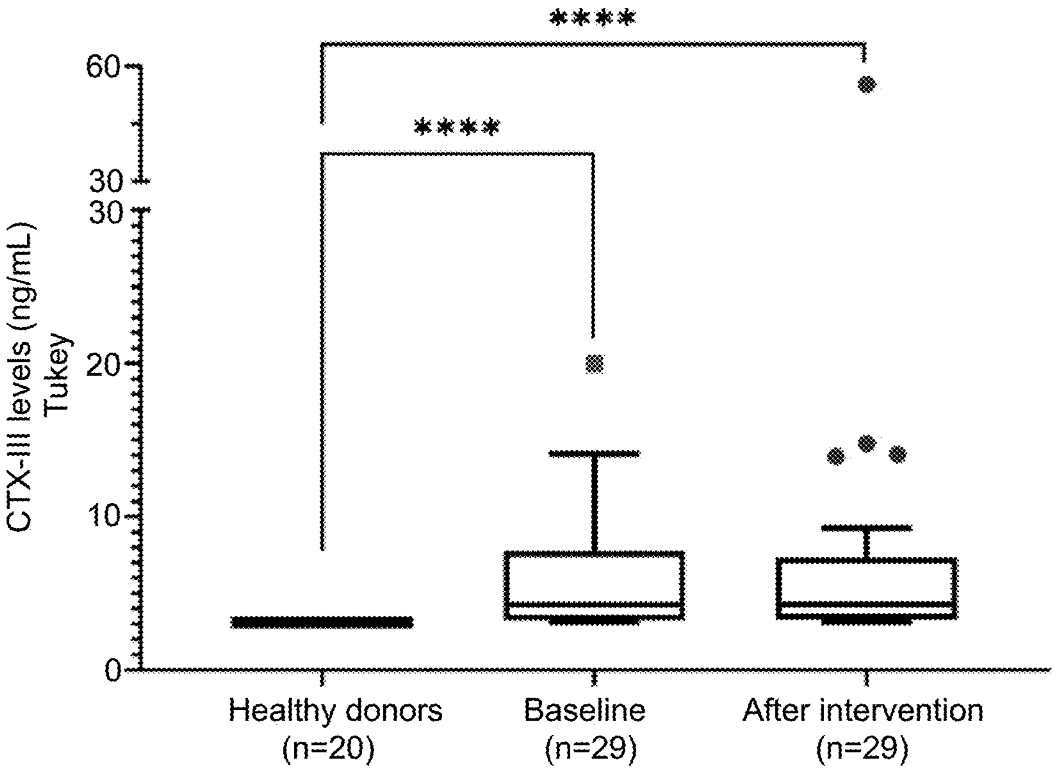

FIG. 12: Serum CTX-III plotted for the healthy donors and EoE patients at baseline and after intervention. Significant differentiation calculated by one-way ANOVA and depicted as follows: p<0.0001****

Figure 13:
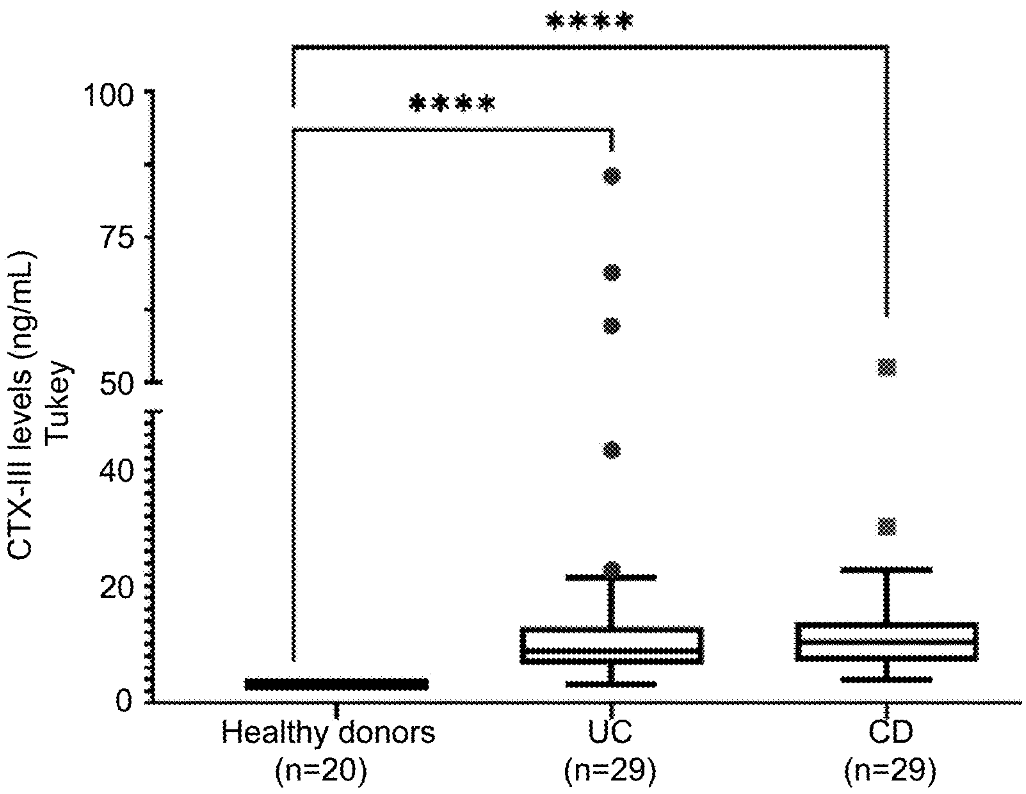

FIG. 13: Plotted CTX-III levels of healthy donors, CD- and UC patients. The statistical difference was calculated by Kruskal-Wallis one-way ANOVA with significance depicted as: p<0.0001****

Figure 14A:
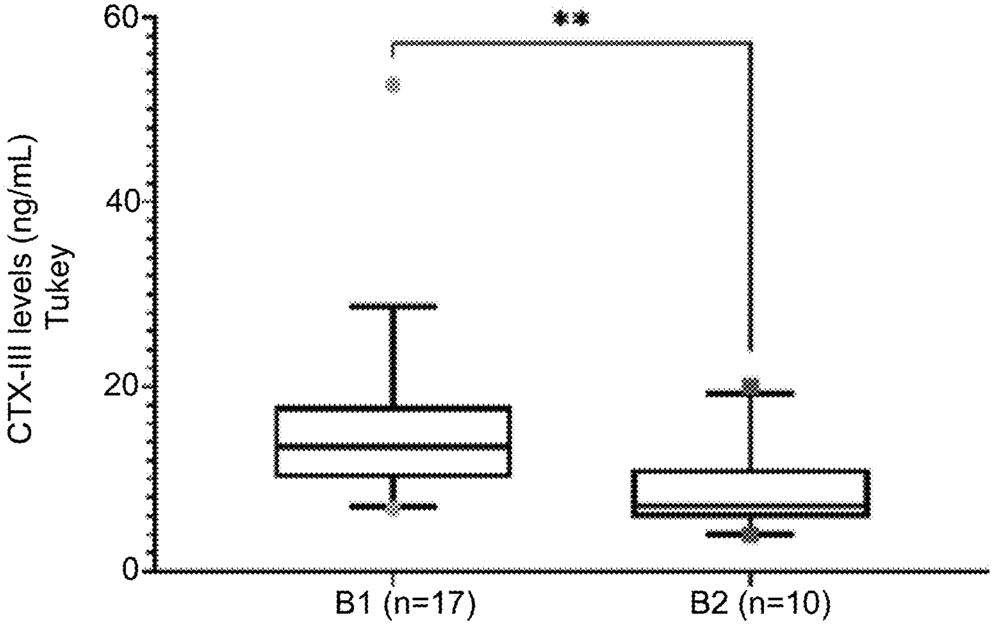
Figure 14B:
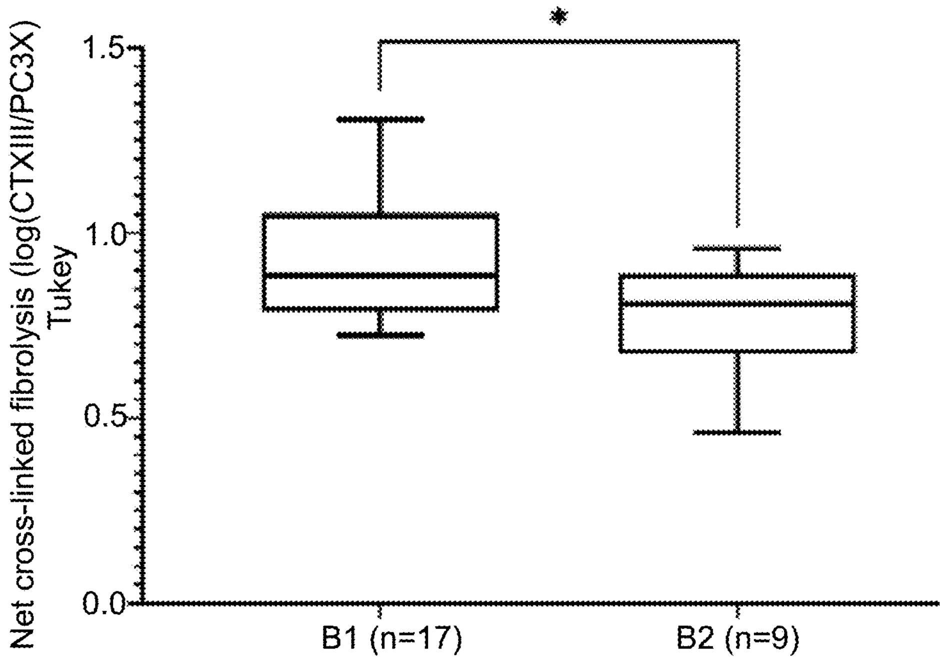
Figure 14C:
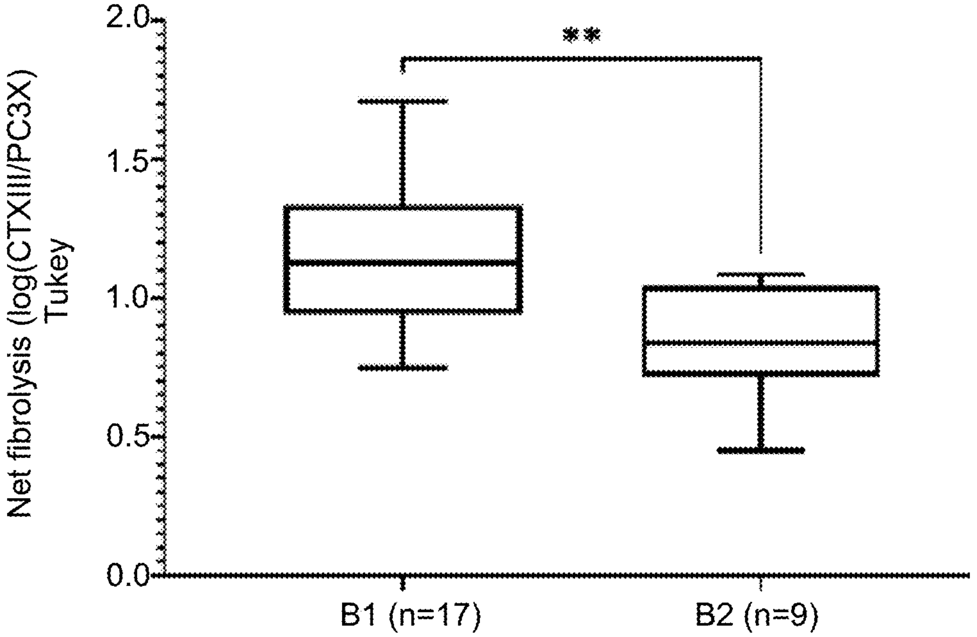

FIGS. 14A-14C: Plasma levels of CTX-III (FIG. 14A), net cross-linked fibrolysis (log (CTX-III/PC3X)) (FIG. 14B), and net fibrolysis (log (CTX-III/PRO-C3)) of patients with either non-stricturing and non-penetrating (B1) or stricturing disease manifestations (B2) as determined by endoscopy. Statistical difference calculated by Mann-Whitney (FIG. 14A) and unpaired t-test (FIG. 14B+FIG. 14C) with the significance depicted as: p<0.05*, and p<0.01 **.

Figure 15:
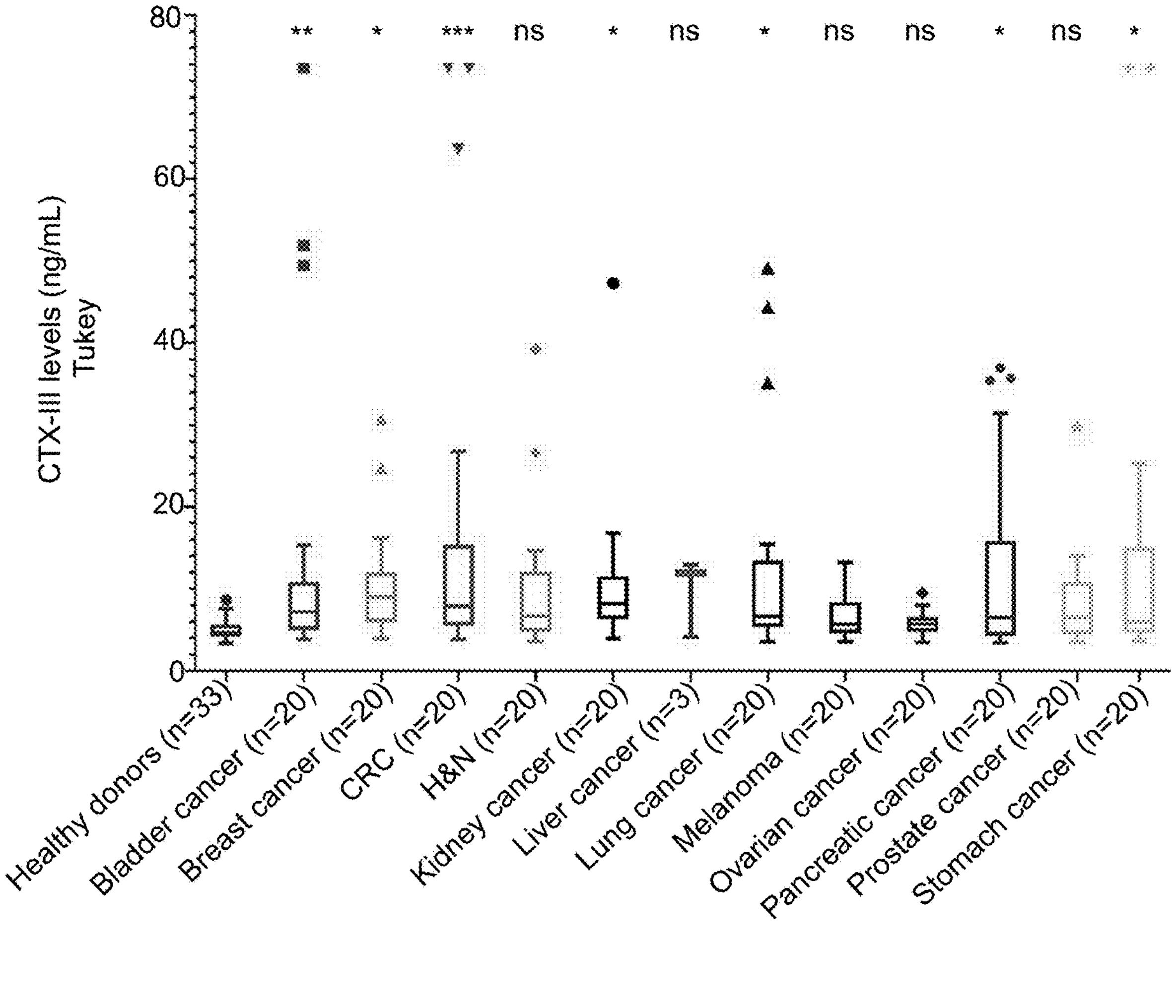

FIG. 15: Box plot illustrating the statistical difference between CTX-III levels of Healthy individuals against 12 types of cancer plotted with the 10-90 percentile. The significance was calculated by ordinary one-way ANOVA and depicted as follows: p>0.05 NS; p<0.05*; p<0.01; p<0.001*.

Figure 16A:
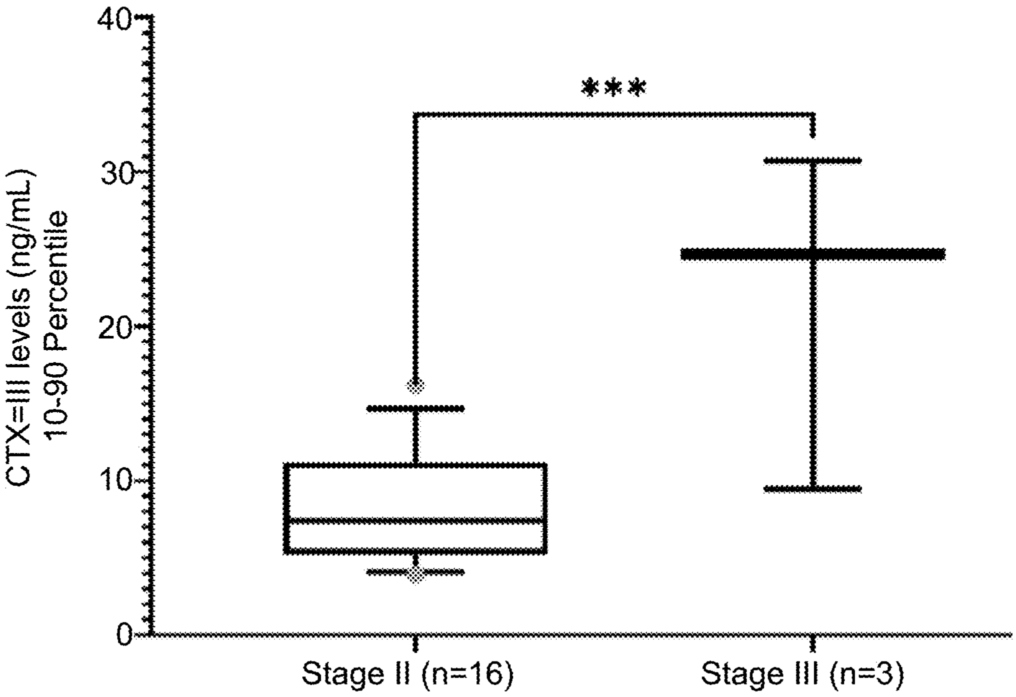
Figure 16B:
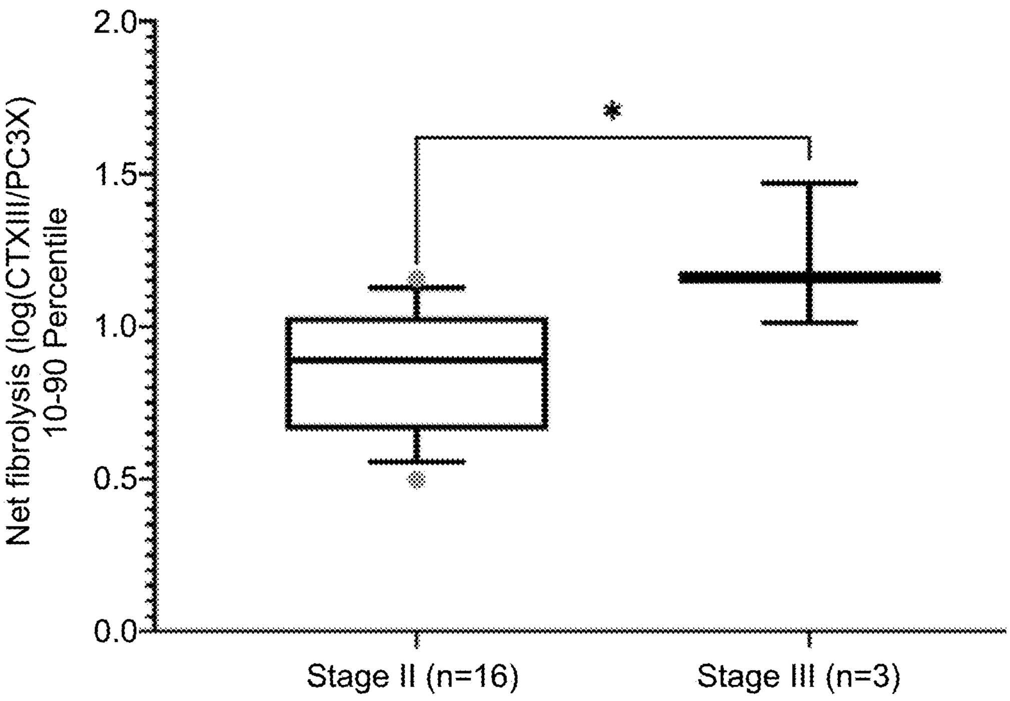

FIGS. 16A-16B: The levels of CTX-III (FIG. 16A) and the net fibrolysis FIG. 16B) was plotted for breast cancer patients in either stage II or stage III. Data is presented as a box plot with 10-90 percentile. The significant differentiation was calculated by parametric t-test and depicted as: p<0.05 *; p<0.001 ***.

EXAMPLE 1

Methods and Materials

Reagents

All reagents used in the experiments were high quality chemicals from companies such as Merck (Whitehouse Station, NJ, USA) and Sigma Aldrich (St. Louis, MO, USA). The synthetic peptides used for monoclonal antibody production and assay development and validation were 1) Immunogenic peptide: Keyhole Limpet Hemocyanin (KLH)-CGG-KAGGFAPYYG, 2) Coating peptide: Biotin-KAGGFAPYYG, 3) Selection peptide: KAGGFAPYYG (SEQ ID NO: 1) or CKAGGFAPYYG×CKAGGFAPYYG (SEQ ID NO: 16) (dimer linked by a N-terminal disulphide bridge), 4) Elongated peptide: KAGGFAPYYGD (SEQ ID NO: 4) or CKAGGFAPYYGD×CKAGGFAPYYGD (SEQ ID NO: 17) (dimer linked by a N-terminal disulphide bridge), 5) Truncated peptide: KAGGFAPYY (SEQ ID NO: 5) or CKAGGFAPYY×CKAGGFAPYY (SEQ ID NO: 18) (dimer linked by a N-terminal disulphide bridge), and 6) Rat dimeric peptide: CKSGGFSPYYG×CKSGGFSPYYG. The dimeric peptides were only used for the assay development and validation. All the synthetic peptides were purchased from Genscript, Piscataway, NJ, USA.

Monoclonal Antibody Production and Clone Characterization

The target neo-epitope (1212'-KAGGFAPYYG-'1221) located in the C-terminal telopeptide of type III collagen was analysed for its uniqueness and the sequence homology with rat and mouse using protein blast (FIG. 1).

Generation of monoclonal antibodies was carried out in four- to six week-old Balb/C mice. The mice were immunized subcutaneously with 200 μL emulsified antigen and 50 μg immunogenic peptide (KLH-CGG-KAGGFAPYYG) using Freund's incomplete adjuvant (Sigma-Aldrich). The mice were immunized with two-week intervals until stable serum titer levels were reached. The mouse with the highest serum titer was selected for fusion. The mouse rested one month and immunized intravenously with 50 μg immunogenic peptide in 100 μL 0.9% NaCl solution. After 3 days, splenocytes were isolated for cell fusion. In brief, splenocytes were fused with SP2/0 myeloma cells to produce hybridoma cells and then cloned in culture dishes using the semi-medium method. The clones were plated into 96-well microtiter plates, and limited dilution was used to secure monoclonal growth. The supernatants were screened for reactivity against the selection peptide (KAGGFAPYYG (SEQ ID NO: 1)) and the elongated peptide (KAGGFAPYYGD (SEQ ID NO: 4)) an indirect competitive ELISA using streptavidin precoated plates (Roche, Hvidovre, Denmark, cat. No 11940279), which were coated with 4 ng/mL of the coating peptide (biotin-KAGGFAPYYG). All reagents were diluted in 50 mM PBS, 1% BSA, 1% Tween-20, 150 mM NaCl, pH 7.4. The two best monoclones were selected for final inhibition, testing their reactivity towards the selection peptide (KAGGFAPYYG (SEQ ID NO: 1)) and not the elongated (KAGGFAPYYGD (SEQ ID NO: 4)), the truncated peptide (KAGGFAPYY (SEQ ID NO: 5)), or the immunogenic peptide (KLH-CGG-KAGGFAPYYG. Prior to purification of the most optimal monoclone, the antibody was isotype tested using the sandwich ELISA kit, the SBA Clonotyping™ System-HRP (Southern Biotech, Birmingham, AL, USA). The monoclone with the best reactivity was purified using protein-G column according to the manufacturer's instructions (GE healthcare Life Sciences, Little Chalfont, Buckinghamshire, UK).

The antibodies generated were sequenced and the CDRs determined.

The sequence of the chains are as follows (CDRs underlined and in bold; Constant region in italics):

Heavy Chain Sequence (Mouse IgG isotype)
(SEQ ID NO: 19)

QVQLQQSGAELVRPGVSVKISCKGSGHTFTDHGMHWVKQSQAKSLEWIG
VISTYYGDATYNQKFKGKATMTVDKSSSTAYMELARLTSEDSAIYYCAR
SMGGNYVGTGFAYWGQGTLVTVSA*AKTTAPSVYPLAPVCGDTTGSSVTL*
*GCLVKGYFPEPVTLTWNSGSLSSGVHTFPAVLQSDLYTLSSSVTVTSST*
*WPSQSITCNVAHPASSTKVDKKIEPRGPTIKPCPPCKCPAPNLLGGPSV*
*FIFPPKIKDVLMISLSPIVTCVVVDVSEDDPDVQISWFVNNVEVHTAQT*
*QTHREDYNSTLRVVSALPIQHQDWMSGKEFKCKVNNKDLPAPIERTISK*
*PKGSVRAPQVYVLPPPEEEMTKKQVTLTCMVTDFMPEDIYVEWTNNGKT*
*ELNYKNTEPVLDSDGSYFMYSKLRVEKKNWVERNSYSCSVVHEGLHNHH*
*TTKSFSRTPGK*

CDR-H1:
(SEQ ID NO: 9)
DHGMH

CDR-H2:
(SEQ ID NO: 10)
VISTYYGDATYNQKFKG

CDR-H3:
(SEQ ID NO: 11)
SMGGNYVGTGFAY

Light Chain Sequence (Mouse Kappa Isotype)
(SEQ ID NO: 20)

DIVMTQAAPSVPVTPGESVSISCRSSKSLLHSNGNTYLYWFLQRPGQSP
QLLIYRMSNLASGVPDRFSGSGSGTAFTLRISRVEAEDVGVYYCMQHLE
FPLTFGAGTKLELK*RADAAPTVSIFPPSSEQLTSGGASVVCFLNNFYPK*
*DINVKWKIDGSERQNGVLNSWTDQDSKDSTYSMSSTLTLTKDEYERHNS*
*YTCEATHKTSTSPIVKSFNRNE*

CDR-L1:
(SEQ ID NO: 6)
RSSKSLLHSNGNTYLY

CDR-L2:
(SEQ ID NO: 7)
RMSNLAS

CDR-L3:
(SEQ ID NO: 8)
MQHLEFPLT.

Assay Development

Monoclonal Antibody Labelling

The monoclonal NBH-242 antibody used as the capture antibody was labelled with biotin by adding 110 μL $Na_2CO_3$/$NaHCO_3$ buffer, pH 9.6 to 1 mL (1 mg/mL) of the antibody, followed by 13.3 μL of biotinamidohexanoic acid N-hydroxysuccinimide ester (Sigma Aldrich, St. Louis, MO, USA, cat. No B2643). The solution was incubated at 20° C. for 1 hour with end-over-end rotation. Subsequently, 110 μL of 0.2 M ethanolamine, pH 8.0 was added to the solution and incubated as before. The solution was dialysed overnight in a Zeba 7k MWCO desalting column (Thermo Scientific, Waltham, MA, USA, cat No. 89889) submerged in 1×PBS at 4° C. Additionally, a portion of the monoclonal antibody was labelled with horseradish peroxidase (HRP) and used as the detection antibody. HRP labelling was performed using the peroxidase labelling kit from Roche, purchased from Sigma Aldrich, St. Louis, MO, USA, cat 11829696001, and done according to the manufactures protocol.

Direct Sandwich ELISA Protocol 96-well plates precoated with streptavidin (Roche Diagnostic's, Hvidovre, Denmark, cat. No. 11940279) were coated with 100 μL of the biotinylated antibody targeting the CTX-III fragment diluted 1+100 in assay buffer (50 mM PBS, 1% BSA, 1% Tween-20, 150 mM NaCl, pH 7.4) for 30 minutes at room temperature rotating at 300 rounds-per-minute (rpm). Unbound biotinylated capture antibody was discarded, and the wells were washed with washing buffer (25 mM TRIZMA, 50 mM NaCl, 0.036% Bronidox L5, 0.1% Tween 20) using a standardized ELISA plate washing machine (BioTek® Instruments, Microplate washer, ELx405 Select CW, Winooski, USA). All samples and the detection antibody were diluted in incubation buffer (50 mM PBS, 1% BSA, 1% Tween-20, 150 mM NaCl, 5% Liquid II, pH 7.4), with the detection antibody being diluted 1+100. 20 μL of sample material and controls were incubated with 100 μL HRP labelled detection antibody targeting the CTX-III fragment, at 4° C. for 20 hours and agitated at 300 rpm. Unbound primary antibody and sample was discarded, and the wells were washed with washing buffer. Subsequently, 100 μL chemiluminescence substrate was added to the wells, plates were incubated for 3 minutes at 20° C. in the dark rotating 300 rpm. Finally, the luminescence emitted was quantified with an ELISA reader (VersaMAX; Molecular Devices, Wokingham Berkshire, UK) set to measure the luminescence at 450 nm and 650 nm. With the results obtained from a 2-fold serial dilution of the dimeric selection peptide (CKAGGFAPYYG x CKAGGFAPYYG (SEQ ID NO: 16)), a standard curve was plotted using a 4-parametric mathematical fit model. Unknown sample measurements were interpolated with the standard curve to obtain the concentration (ng/mL) of the CTX-III fragment.

Technical Validation

The lower limit of detection (LLOD) was determined from 21 zero samples (i.e. incubation buffer) and calculated as the mean+3× standard deviation, whereas the upper limit of detection (ULOD) was determined from 10 measurements of the dimeric selection peptide calculated as the mean+3× standard deviation. The inter- and intra-assay variation was determined by 10 independent runs of five quality control (QC) samples with minimum three of these being healthy human plasma EDTA samples (Valley Biomedical, Winchester, VA, USA), with each run consisting of double determinations of the samples. The acceptance criteria for the inter- and intra-assay variation was 15% and 10%, respectively. Assay linearity was determined by calculating the percentage recovery (100%±20%) of a 1:6-fold dilution of healthy human plasma EDTA samples with a significant concentration, using the undiluted sample as reference. Specificity of the assay was determined by calculating the percentage recovery of the dimeric elongated peptide, the dimeric truncated peptide, and the dimeric rat peptide measurements towards the 100% sample of the dimeric selection peptide. The accuracy of sample measurements was determined by spiking two samples of healthy human plasma EDTA with a significant concentration, and subsequently calculating the percentage recovery between the theoretical and the actual measurements. Interference from biotin, lipids, and haemoglobin was tested by spiking healthy human plasma EDTA samples with a known concentration of the interferent. Subsequently, the percentage recovery between the control sample and the low or high interferent samples were calculated.

Analyte and Reagent Stability

The stability of the CTX-III fragment was determined by calculating the percentage recovery of three healthy human plasma EDTA samples from the non-stressed sample. The samples underwent up to four cycles of freeze and thaw or were subjected to 2, 4, 24, or 48 hours of incubation at either 4° C. or 20° C.

In vitro Cleavage Assay

Clinical Cohort Measurement

Biomarker Assay

Assessment of type III collagen formation was performed using the PRO-C3 (32) competitive ELISA targeting a neo-epitope in the N-terminal propeptide. In brief, streptavidin coated 96-well plates were incubated for 30 min at 20° C., 300 rpm with 100 μL of biotinylated coater peptide diluted 1+100 in a PBS buffered coating solution containing protein stabilizers and preservatives. Following incubation, the coating solution was discarded, and the wells washed five times in washing buffer (25 mM TRIZMA, 50 mM NaCl, 0.036% Bronidox L5, 0.1% Tween 20) using a standardized ELISA plate washing machine (BioTek® Instruments, Microplate washer, ELx405 Select CW, Winooski, USA). 20 μL of sample material was added to the appropriate wells with subsequent addition of 100 μL of HRP-labelled antibody diluted 1+100 in the incubation buffer. The plates were incubated for 20 hours at 4° C., 300 rpm after which they were washed as previously described. Tetramethylbenzidine (TMB, Kem-En-Tec cat. No. 438OH, Taastrup, Denmark) was used as the colorimetric reagent with 100 μL/well with 15 min incubation agitating 300 rpm in the dark. The reaction was stopped with the addition of 100 μL of 1% $H_2SO_4$ and the optical density was read at 450 nm with 650 nm as reference using an ELISA reader (VersaMAX; Molecular Devices, Wokingham, UK). The concentration of PRO-C3 within the analysed samples was determined by interpolation with the 4-parametric logarithmic standard curve generated through a 2-fold serial dilution of the selection peptide.

Results

Monoclonal Antibody Production and Characterization

Alignment of the rat-, mouse-, and human sequence of type III collagen revealed two amino acid differences (designated by ":" in FIG. 1). Isotype characterization determined the antibody NBH-242 used for the assay development to be an IgG2a κ-light chain. In the final inhibition the monoclonal antibody did not show any reactivity towards the elongated-, truncated-, or the immunogenic-peptide, observed by the lack of signal inhibition. Testing the reactivity towards the selection peptide demonstrated an increasing signal inhibition with the peptide concentration, thus illustrating its binding to the antibody in the indirect competitive ELISA (FIG. 2).

Technical Validation

In the development of the sandwich ELISA, the monoclonal NBH-242 antibody was used as both the capture and detection antibody. The measurement range of the human CTX-III ELISA was determined by calculating the LLOD and the ULOD, which provided a range from 0.92-15.94 ng/mL. The technical performance of the assay determined by calculating the inter- and intra-assay variations was acceptable with variations of 14.8% and 5.4%, respectively (Table 4). Assay linearity was tested in healthy human plasma EDTA samples, which resulted in a mean recovery of 108.9%, thus within the acceptable range of 100%±20%, (Table 5). Diluting the samples any further resulted in concentration below the measurement range. By plotting the calculated percentage recovery, the specificity of the antibodies in the direct sandwich ELISA towards the dimeric peptides was tested. Here, antibodies showed no reactivity towards either the dimeric elongated-, dimeric truncated-, or the dimeric rat-peptide, while showing reactivity towards an increasing concentration of the dimeric selection peptide illustrated by the increasing luminescence (y-axis) (FIG. 3). Spiking healthy human plasma EDTA samples with another healthy human plasma EDTA sample, resulted in mean recoveries of 102.2% (Table 6). None of the tested interferents demonstrated an effect on the sample measurements in the healthy human plasma EDTA samples with a mean recovery within the acceptable range (100%±20%) (Table 7).

TABLE 4

Inter- and Intra-assay variation for the CTX-III assay by using five QC samples (three of these was healthy human plasma EDTA samples with the last two being the dimeric selection peptide). The variation (%) is calculated as the mean of 10 individual double determinations of each sample.

| CTX-III sample | Mean value (ng/ml) | Intra-assay variation (%) | Inter-assay variation (%) |
|---|---|---|---|
| #1 | 3.16 | 6.7 | 12.5 |
| #2 | 9.13 | 8.3 | 12.9 |
| #3 | 3.10 | 4.0 | 30.5 |
| #4 | 4.03 | 2.2 | 2.6 |
| #5 | 1.60 | 5.8 | 15.3 |
| Average | | 5.4 | 14.8 |

TABLE 5

The sample dilution recovery of four healthy Human Plasma EDTA samples (HP).

| Undiluted | HP (n = 4) 100% |
|---|---|
| 5:6 | 101.5 |
| 4:6 | 100.8 |
| 1:2 | 124.3 |
| Average | 108.9 |

TABLE 6

Healthy human plasma EDTA samples with a significant concentration was spiked with each other and the spiking recovery (%) calculated between the measured- and theoretical-sample measurement.

| Samples spiked | Spiking recovery (%) |
|---|---|
| HP1 + HP2 | 117.3 |
| HP2 + HP3 | 115.9 |
| HP4 + HP2 | 90.2 |
| HP5 + HP2 | 101.9 |
| HP5 + HP6 | 85.6 |
| Average | 102.2 |

TABLE 7

The interference from haemoglobin, biotin, and lipids in three healthy human plasma EDTA samples. The recovery (%) is calculated from the low and high concentration of the interferent to the pure plasma EDTA sample.

| CTX-III | Haemoglobin | | Biotin | | Lipid | |
|---|---|---|---|---|---|---|
| sample | Conc. | Recovery | Conc. | Recovery | Conc. | Recovery |
| HP1 | | 109.2 | | 97.2 | | 111.1 |
| | | 10.46 | | 102.4 | | 100.7 |
| HP2 | | 103.6 | | 103.4 | | 91.5 |
| | | 111.9 | | 98.3 | | 93.1 |
| HP3 | | 112.5 | | 103.5 | | 99.3 |
| | | 118.1 | | 98.1 | | 108.9 |

Analyte and Reagent Stability

The stability of the analyte in healthy human plasma EDTA samples was stable for up to four cycles of freeze/thaw (Table 8). The mean recovery for incubation at 4° C. of the healthy human plasma EDTA samples was 92.5% with stability up to 48 hours in all samples. At 20° C. the mean recovery was 114.7%, with three out of four samples demonstrating analyte stability up to 24 hours. (Table 9).

TABLE 8

| Freeze/Thaw cycle no. | Recovery (%), HP (n = 4) |
|---|---|
| 1 | 100 |
| 2 | 83.6 |
| 3 | 104.5 |
| 4 | 104.9 |
| Average | 97.7 |

TABLE 9

| Incubation time and temperature | Recovery (%), HP (n = 4) |
|---|---|
| 0 h/4° | 100 |
| 2 h/4° | 93.8 |
| 4 h/4° | 93.0 |
| 24 h/4° | 91.7 |
| 48 h/4° | 83.8 |
| 0 h/20° | 100 |
| 2 h/20° | 109.7 |
| 4 h/20° | 115.8 |
| 24 h/20° | 121.5 |
| 48 h/20° | 126.6 |

Discussion

Based on the production of a monoclonal antibody targeting a neo-epitope in the C-terminal telopeptide of type III collagen following C-proteinase cleavage, a novel CTX-III sandwich ELISA was developed by utilizing the NBH-242 monoclonal antibody to detect cross-linked fragments of type III collagen. In brief, the assay demonstrated high specificity towards the human neo-epitope with the ability to detect the analyte in human plasma EDTA samples. Additionally, the assay showed to be technically stable with an acceptable inter- and intra-assay variation, linearity, and accurate measurements.

Characterization and Technical Validation

During the antibody characterization, the monoclonal antibody reactivity was tested in a competitive ELISA towards variations of the neo-epitope sequence, and while this showed the high specificity of the antibody, the peptides used were monomeric and did therefore not validate the antibodies use in a sandwich ELISA. Thus, a set of dimeric peptides was designed containing two identical sequences of the different peptide variations mentioned earlier, cross-linked through a disulphide bond located N-terminal to the antibody binding site. Testing the reactivity towards the dimeric peptides, the antibody elicited a high specificity towards the dimeric human selection peptide, thus re-validating its high specificity towards the human neo-epitope sequence, while also demonstrating its potential usefulness in the detection of cross-linked fragments.

Due to the high specificity and the inability of the antibody to detect the rat sequence homolog, the assay development and validation focused on human sample material. Native reactivity was shown in human plasma EDTA samples, though most of the measured sample values were in the lower end of the measuring range, as can be observed from the HD levels in FIG. 3. Samples within the measuring range was selected for the technical validation of the assay, which revealed its technical stability. The inter- and intra-assay variations was acceptable, as was the dilution recovery of healthy human plasma EDTA samples, and the spiking recovery showing the accuracy of the assay.

Analyte and Reagent Stability

An important factor in the development and clinical use of an assay is the stability of the analyte, allowing the accurate measurement of sample material after various freeze and thaw cycles, and incubation at higher or lower temperatures. This is especially important when measuring clinical sample material where the exact sample handling may not be fully known. Testing the stability of the CTX-III analyte did not suggest any major instabilities, although careful handling of samples should always be a priority.

In the following examples the level of CTX-III was measured using the assay described above. The level of PROC3 was measured using the method described in WO 2014/170312 and the level of PC3X was measured using the assay described in WO2017/34172.

EXAMPLE 2—BARIATRIC SURGERY 58 patients with non-alcoholic fatty liver disease (NAFLD) having undergone bariatric surgery were sampled for blood at baseline and 6 months follow-up. A schematic overview of the patient demographics is provided in table 10, which include patient BMI, non-alcoholic fatty liver disease activity score (NAS), steatosis grade, inflammation grade, ballooning, and their fibrosis stage. Patient demographics were only obtained at baseline with demographics only provided for 45-48 of the patients. Prior to the surgical procedure, patients were put on a diet to encourage preoperative weight loss. The measured samples were plasma EDTA which had been stored at −80° C. until CTX-III measurement.

TABLE 10

Represent the bariatric surgery patient demographics at baseline.

| | | |
|---|---|---|
| BMI, mean kg/m$^2$ range | 51 | 38-66 |
| NAS score | | |
| <2, n % | 28 | 59.6% |
| | 9 | 19.1% |
| 3-4, n % | 10 | 21.3% |
| >5, n % | | |
| Steatosis grade | | |
| <5%, n % | 18 | 37.5% |
| 5-33%, n % | 16 | 33.3% |
| 33-66%, n % | 8 | 16.7% |
| >66%, n % | 6 | 12.5% |

TABLE 10-continued

| Represent the bariatric surgery patient demographics at baseline. | | |
|---|---|---|
| **Inflammation grade** | | |
| No foci, n % | 8 | 17.8% |
| <2 foci/200× field, n % | 22 | 48.9% |
| 2-4 foci/200× field, n % | 12 | 26.7% |
| >4 foci/200× field, n % | 3 | 6.7% |
| **Ballooning** | | |
| None, n % | 30 | 65.2% |
| Few ballooned cells, n % | 16 | 34.8% |
| Many ballooned cells, n % | 0 | 0% |
| **Fibrosis stage** | | |
| F0, n % | 17 | 36.2% |
| F1, n % | 25 | 53.2% |
| F2, n % | 5 | 10.6% |
| F3, n % | 0 | 0% |
| F4, n % | 0 | 0% |

Statistical Analysis

Comparisons of the CTX-III levels between the healthy plasma EDTA samples and the plasma EDTA samples from the cohort of bariatric surgery patients were done by applying one-way ANOVA (Kruskal-Wallis) correcting for the false discovery rate. Results are shown as the median CTX-III levels+Inter Quartile Range (IQR). All statistical analyses were performed in GraphPad Prism v.8.2.0 (Graph Pad Software, La Jolla, CA, USA). Asterisks indicate the following: *: p<0.05; : p<0.01; *: p<0.001; ****: p<0.0001; ns=non-significant difference.

Results

CTX-III Levels Relate to NAFLD

The levels of CTX-III were significantly higher in patients of NAFLD having undergone bariatric surgery, at baseline (p<0.0001), and 6 months follow-up (p<0.001) when compared with the levels of the Healthy human plasma EDTA Donors (HDs) (FIG. 4). Furthermore, the baseline (p<0.01) levels was significantly higher than the levels at the 6 months follow-up (FIG. 4).

Deposition of Type III Collagen

The ratio of PRO-C3 and CTX-III depicting the net deposition of type III collagen was significantly elevated in the bariatric surgery patients at the 6 months follow-up in comparison with the patients at baseline (p<0.0001) (FIG. 5).

Discussion

The development of the CTX-III assay demonstrated an ability to differentiate between HDs and NAFLD patients, including the differences between baseline levels and the 6 months follow-up levels.

CTX-III Levels Relate to NAFLD

NAFLD is one of the major chronic liver diseases affecting about one-quarter of the population (33), with one of the major causes being obesity which results in the accumulation of fat in the liver (34). This accumulation can then lead to initiation of the inflammatory cascade with the potential of formation of scar tissue, ultimately leading to a state of liver fibrosis (34). Here, the excessive accumulation of ECM components, including type III collagen (35) and the ECM related cross-linking enzyme LOXL2 (36) contribute to further the disease progression. As such, the potential and biological relevance of the novel CTX-III marker in a study of NAFLD patients having undergone bariatric surgery, was evaluated. By measuring the CTX-III levels in plasma EDTA samples obtained from the NAFLD patients at baseline and 6 months follow-up a significant difference between the patients at each timepoint was demonstrated. Furthermore, when comparing the CTX-III levels of the NAFLD patients with the HDs, patients diagnosed with NAFLD showed biomarker levels significantly higher at all time-points. This increased level of the CTX-III marker suggests a significantly increased level of fibrolysis taking place in the bariatric surgery patients. In combination with CTX-III, the liver fibrosis relevant PRO-C3 biomarker of type III collagen formation was also measured. Combining the two biomarker measurements provided a measure of type III collagen net deposition. Here, the deposition was increased from baseline to the 6 months follow-up suggesting a switch from degradation of mature cross-linked type III collagen to the formation of new collagen within the tissue. These data indicate the potential of the CTX-III marker in distinguishing between individuals with a known active disease as well as monitoring their levels of CTX-III over time. The CTX-III marker was unable to differentiate between patients based on their individual disease scores, including steatosis grade, inflammation grade, ballooning, BMI, fibrosis stage, or NAS score (data not shown).

EXAMPLE 3 HCV RELATED LIVER FIBROSIS

Study Description

A total of 158 patients diagnosed with Hepatitis C Virus (HCV) related liver fibrosis were sampled for blood at the time of screening and after 52 weeks with the measured sample material being plasma EDTA. Table 11 provides an overview of the total patient population, while table 12 represents the 47 patients of the placebo group.

TABLE 11

Demographic overview of patients at screening diagnosed with HCV related liver fibrosis

| HCV RELATED FIBROSIS | |
|---|---|
| N | 158 |
| AGE, YR | 51.6 |
| MEN, N (%) | 100 (63.3) |
| BMI, KG/M$^2$ | 28.6 |
| BASELINE ISHAK SCORE | 2.7 |
| AST, IU/I | 64 |
| FIBROTEST, IU | 0. |
| CTX-III, NG/ML | 4.5 |
| NET FIBROLYSIS, RATIO | 0.45 |

TABLE 12

Demographic overview of the patients within the placebo group showing data at time of screening

| | REGRESSORS | STABLE | PROGRESSORS | P VA |
|---|---|---|---|---|
| N | 5 | 31 | 11 | |
| AGE, YR | 50.2 | 51.5 | 48.7 | NS |
| MEN, N (%) | 5 (100) | 21 (67.7) | 7 (63.6) | NS |
| BMI, KG/M$^2$ | 32 | 30.3 | 31 | NS |
| BASELINE ISHAK SCORE | 2.8 | 2.5 | 2.8 | NS |
| DELTA ISHAK SCORE | −1 | 0 | 1.3 | <0.0 |
| AST, IU/I | 42.6 | 61 | 112 | 0.0 |
| FIBROTEST, IU | 0.6 | 0.6 | 0.7 | NS |
| CTX-III, NG/ML | 7.1 | 3.5 | 3 | <0.0 |
| NET FIBROLYSIS, RATIO | 0.63 | 0.43 | 0.31 | <0.0 |

Statistical Analysis

Comparisons of the CTX-III levels between the healthy plasma EDTA samples and the plasma EDTA samples from the cohort of HCV related liver fibrosis patients were done by applying non-parametric t-test or one-way ANOVA depending on the number of groups analysed (Mann-Whitney or Kruskal-Wallis). Data was corrected for False Discovery Rate. Results are shown as median CTX-III or net fibrolysis+Inter Quartile Range (IQR) unless otherwise stated. Biomarker tertial levels were defined as follow starting from lowest biomarker levels to highest: $1^{st}$-, $2^{nd}$-, and $3^{rd}$-tertile. All statistical analyses were performed in GraphPad Prism v.8.4.3 (Graph Pad Software, La Jolla, CA, USA) and MedCalc v.19.3 (MedCalc Software Ltd, 8400 Ostend, Belgium). Asterisks indicate the following: *: p<0.05; : p<0.01; *: p<0.001; ****: p<0.0001; ns=non-significant difference.

Results

Patients presenting with HCV related liver fibrosis was stratified according to their Ishak score at time of screening and their CTX-III levels compared to the levels of healthy donors. Independent of the degree of fibrosis, patients presenting with liver fibrosis had significantly (p<0.0001) elevated CTX-III levels at screening compared to the healthy donors (FIG. 6).

Calculating the degree of net fibrolysis (CTX-III/PRO-C3) at screening, a significant difference was discovered between patients presenting with various degree of fibrosis utilizing the Ishak classification (FIG. 7). Patients with an Ishak score of 1-2 elicited a higher degree of net fibrolysis compared to patients with a score of 4-5 (p<0.05). The same was true for patients with a score of 3, in which the levels were significantly elevated compared to patients with a score of 4-5 (p<0.05)

A total of 47 patients were treated with a placebo for 52 weeks after which their Ishak score were determined. Patients were then stratified according to their change in the Ishak score from screening to 52 weeks and defined as having either a Regressive-, Stable-, or Progressive-fibrotic phenotype. Plotting the CTX-III levels at screening of each phenotype, biomarker levels were found significantly elevated in patients having a spontaneous regressive phenotype compared to a progressive phenotype (p<0.01). Additionally, those presenting with a stable fibrotic phenotype demonstrated significantly higher CTX-III levels at screening compared to the progressive phenotype (p<0.05) (FIG. 8A). By calculating net fibrolysis at screening allowed for a more significant differentiation between patient phenotypes as patients with a regressive phenotype displayed significantly higher levels of fibrolysis (p<0.001) compared to a progressive phenotype, while the same was true when comparing the stable and progressive phenotype (p<0.01) (FIG. 8B).

Dividing patients of the placebo group in tertiles based on either their CTX-III levels or levels of fibrolysis at screening, demonstrated a significant decrease of the Ishak score of patients with high levels of CTX-III at screening (3rd tertile) compared to patients with low initial CTX-III levels (1st tertile) (FIG. 9A). Observing the Ishak score changes based upon net fibrolysis, patients with levels in the 3rd tertile presented with a significant decrease compared to patients of the 1st tertile (p<0.001). Additionally, patients having levels of fibrolysis in the 2nd tertile at screening also presented with a significant decrease in their Ishak score compared to the 1st tertile (p<0.01) (FIG. 9B).

Based on the receiver operator characteristic (ROC) and its summary statistic, the Youden index, an optimal cut-off value for a regressive fibrotic phenotype was determined for both CTX-III and fibrolysis levels at screening (Table 13). Levels of CTX-III>3.8 ng/mL at screening resulted in a significant reduction in the Ishak score compared to patients with levels lower than the cut-off value (p<0.01) (FIG. 10A). The same was true for the net fibrolysis in which patients with a ratio of cross-linked type III collagen degradation (CTX-III) and type III collagen formation (PRO-C3) above 0.5 experienced a significant reduction in the Ishak score (p<0.01) compared to patients presenting with low levels of fibrolysis (FIG. 10B).

TABLE 13

Identification of spontaneous regressors using a specific cut-off value of either CTX-III levels or degree of net fibrolysis as screening and their associated values from the ROC curve.

| BIOMARKER, CUT-OFF VALUE | SENSITIVITY, % (95% CI) | SPECIFICITY, % (95% CI) | PLR, (95% CI) | NLR, (95% CI) |
|---|---|---|---|---|
| CTX-III, 3.8 NG/ML | 80 (28.4-99.5) | 85.4 (70.8-94-4) | 5.5 (2.3-12.9) | 0.2 (0.04-1.4) |
| NET FIBROLYSIS, 0.5 | 80 (28.4-99.5) | 85.4 (70.8-94.4) | 5.5 (2.3-12.9) | 0.2 (0.04-1.4) |

ROC, RECIEVER OPERATING CHARACTERSTIC;
C; CONFIDENCE INTERVAL;
PLR, POSITIVE LIKELIHOOD RATIO;
NLR, NEGATIVE LIKELIHOOD RATIO

Patients were stratified based on cutoff levels determined by calculating the Youden index, with subsequent logistic regression calculating the odds ratio for being a regressor of fibrosis. This resulted in an odds ratio for being a spontaneous regressor of fibrosis of 19.4 times higher (p=0.0088) for patients with CTX-III levels ng/mL at screening compared with patients presenting with levels lower than this value. Observing patient levels of fibrolysis, a fibrolytic ratio ≥0.5 the odds ratio increased to 23.3 (p=0.0057) (FIG. 11).

Discussion

Type III Collagen in HCV Fibrosis

During the progression of fibrosis, pathogenic cell activation results in excessive formation of collagen within the ECM particularly the main fibrillar collagens of type I, III, and V. Combined with an increase of collagen cross-linking enzymes such as LOXLs and TGs, the increased fibrillar collagen deposition and subsequent cross-linking leads to increased tissue stiffening causing tissue disruption which may lead to organ failure (37). In HCV related liver fibrosis, unchecked viral infection results in loss of tissue homeostasis with resulting chronic inflammation causing expression of several inflammatory and fibrogenic cytokines including tumour growth factor-β1 (TGF-(β1). This cascade of fibrogenic cytokines ultimately activates quiescent hepatic stellate cells to transdifferentiate to myofibroblast (38). Myofibroblast constitutes the main effector cells of fibrosis responsible for ECM production and modulation of matrix stiffness mediated by extensive collagen cross-linking and ECM contraction (39). Accumulation of type III collagen in HCV related liver fibrosis have previously been shown with the biomarker PRO-C3 quantifying type III collagen formation through highly sensitive monoclonal antibodies targeting the $NH_2$ pro-peptide of type III collagen (40,41). With the known relation of PRO-C3 and a fibrogenic phenotype, the association between fibrolysis and the novel biomarker CTX-III was investigated. Similar to the results investigating CTX-III levels in NAFLD, patients suffering from HCV related fibrosis presented with elevated levels of cross-linked type III collagen degradation in comparison to HDs. Furthermore, increased levels of fibrolysis in patients with the lowest degree of fibrosis (Ishak score 1-2) were observed, suggesting an increase of fibrolysis of mature cross-linked type III collagen as well as a decrease in type III collagen formation. These data indicate upregulated proteolysis of the cross-linked fibrotic ECM, with net fibrolysis is capable of differentiating between patients based on the degree of fibrosis.

Resolution of Fibrosis

Though fibrosis was long thought to be irreversible, understanding of fibrosis has changed in recent years, now acknowledging fibrosis as a dynamic process of fibrogenesis and fibrolysis. As new anti-fibrotic therapeutics are being developed, which includes targets such as LOXL2/3 (42), the end goal of fibrotic resolution is within reach. However, in order to optimise clinical management highly sensitive and specific tools capable of assessing patients accordingly is needed. Serological biomarkers of ECM turnover could provide a non-invasive tool for this, as has previously been demonstrated with the PRO-C3 biomarker identifying patients with a spontaneous progressive fibrotic phenotype (43,44). Dividing patients according to whether their fibrotic phenotype regressed, remained stable, or progressed after 52 weeks, significant differences were observed in both CTX-III and net fibrolysis levels between a regressive and progressive phenotype at the time of screening. These data suggest a prognostic potential of the biomarkers, in which patients with initial high levels of cross-linked type III collagen degradation i.e. fibroylsis experience a spontaneous resolution of their fibrotic ECM compared to patients with a lower degree of fibrolysis.

Identification of Regressors. Consequences for Therapy

Calculating a cut-off value for the biomarkers, demonstrated how patients in this exploratory study with CTX-III levels ng/mL or fibrolysis levels≥5 at screening had 19.4- and 23.3-times higher chance of presenting with a regressive phenotype. Biomarker cut-off levels can be used at screening to identify spontaneous regressors. Patients presenting with a spontaneous resolution of fibrotic ECM may need a lower treatment dose compared to patients with low initial fibrolysis as determined by the biomarkers. Consequently, this would lead to better patient stratification during trials, decreased expenses, increased patient welfare, and potentially aid in treatment development.

EXAMPLE 4 EOSINOPHILIC ESOPHAGITIS

Methods

Patient Demographics and Clinical Evaluation

Twenty-nine adult EoE patients treated with an elimination diet were included for analysis. Dysphagia and EREF total score were assessed at baseline and after intervention by endoscopy.

TABLE 14

Display basic patient demographics of EoE patients at baseline and after intervention, including healthy donors. Demographics include age, gender, presence of dysphagia, and the Eosinophilic Esophagitis Reference Score (EREFS) total.

| | EoE patients at baseline | EoE patients after intervention | Healthy donors | P value |
|---|---|---|---|---|
| N | 29 | 29 | 20 | |
| Age, year range | 37 22-62 | 37 22-62 | 46 18-61 | 0.0039 |
| Gender, male % | 17 58.6% | 17 58.6% | 10 50% | NS |
| Dysphagia daily, n % | 14 48.3% | 3 10.3% | ND | <0.0001 |
| EREF total, mean range | 4.5 1-8 | 3.0 1-5 | ND | <0.0001 |

Statistical Analysis

Statistical variance between patient demographics and clinical parameters of patients at baseline and after intervention was determined by Fischer's Exact test for two groups or Chi square test for multiple groups.

Calculating the statistical differentiation between serum CTX-III of EoE patients at both timepoints and healthy donors were done by one-way ANOVA applying Kruskal-Wallis for non-parametric data. A p value below 0.05 was determined as being statistically significant.

Results

Cohort Description

There was a significant difference in the mean age of the EoE patients and healthy donors (p=0.0039), with the healthy donors being on average nine years older. Comparison of the EREF total score of the EoE patients at baseline and following the elimination diet, a significant reduction ($p<0.0001$) was observed (Table 14).

Diagnostic Potential of the CTX-III Biomarker, Distinguishing EoE Patients and Healthy Donors Serum CTX-III levels were significantly elevated at both baseline and after the elimination diet (after intervention) compared to healthy donors ($p<0.0001$). No significant differentiation was demonstrated between baseline and the after-intervention levels (FIG. 12).

Discussion

By applying the CTX-III biomarker in a study of 29 EoE patients with blood-sampling at baseline and following a 6-week elimination diet as well as healthy donors, elevated serum CTX-III in EoE patients was demonstrated. Located in the interstitial matrix, deposition of type III collagen during fibrosis in EoE would primarily occur in the subepithelial layer by activated myofibroblast (46,49). In the final steps of collagen maturation, high amounts of secreted cross-linking enzymes mediate an extensive formation of intra- and inter-molecular cross-links. The ability of the heavily cross-linked and pathological collagen matrix of EoE patients to initiate myofibroblast differentiation of healthy donor fibroblast, underlines the importance of the ECM in propagating EoE related fibrosis (59). Clinical symptoms caused by esophageal fibrosis occur later than the actual onset of subepithelial fibrosis with the risk doubling for every 10-year of disease duration (60). Thus, early evaluation of fibrotic extracellular matrix remodelling is critical for early initiation of treatment (61). Here, quantification of protease degraded metabolites of cross-linked type III collagen demonstrated a diagnostic potential of the CTX-III biomarker. With significantly elevated serum levels of CTX-III in patients diagnosed with EoE, the biomarker could provide a supportive diagnostic tool in EoE, and potentially also to serve as pharmacodynamic marker for EoE. Though no anti-fibrotic treatment or markers to monitor fibrostenosis development or resolution of fibrosis is currently available for EoE, studies are ongoing for therapeutics targeting especially key pro-inflammatory cytokines of EoE pathogenesis. Current therapeutic options include administration of topical steroids and elimination diets (62). These two therapies have demonstrated reduction of esophageal eosinophilia but have yet to demonstrate reduction of fibrosis.

Conclusion

In the current study, EoE patients were placed on a 6-week elimination diet which did not result in any significant effect on the serum CTX-III levels. Although no changes in CTX-III biomarker levels by short term dietary intervention was observed, the significantly elevated levels of protease degraded and cross-linked type III collagen in EoE patients indicates the biomarker's potential in type III collagen remodelling of EoE related fibrosis.

EXAMPLE 5—INFLAMMATORY BOWEL DISEASE

Methods

Patient Demographics and Pathological Evaluation

At the time of blood sampling patients were endoscopically assessed and scored according to the simple endoscopic score for CD (SES-CD). Patients with a SES-CD score of 0-1 was determined as endoscopically inactive, whereas a score>1 was determined as endoscopically active. Additionally, when a SES-CD score was unavailable, determination of an inactive or active disease was based patients Harvey-Bradshaw Index (HBI) score, which was determined on clinical parameters. A HBI score of 0-4 represented patients with a clinically inactive disease, while a score>4 determined patients with a clinically active disease.

Further patient stratification occurred by utilizing the Montreal classification for disease behaviour with patients separated into either the non-stricturing and non-penetrating (B1) or stricturing disease behaviour (B2). Patients in the Montreal A1 group for patients with an age of disease onset of 16 years or below, and/or patients with a Montreal B4 classification for perianal disease behaviour was excluded from the analysis.

TABLE 15

Summary of patient demographics and stratification according to endoscopic-, or clinical disease activity as well as endoscopic disease behaviour.

| | Healthy donors | Ulcerative Colitis | Crohn's Disease | B1 (non-stricturing non-penetrating) | B2 (stricturing) | P value (B1 vs. B2) |
|---|---|---|---|---|---|---|
| N | 20 | 102 | 61 | 37 | 19 | 0.008 |
| Age, mean | 46 | 45.1 | 36.1 | 32.4 | 42.9 | 0.0118 |
| range | 18-61 | 18-80 | 19-76 | 19-76 | 18-72 | |
| Sex, male | 10 | 57 | 33 | 21 | 10 | NS |
| (n %) | 50% | 55.9 | 54.1% | 56.8% | 52.6% | |
| BMI, mean | ND | 26.3 | 25.4 | 26.1 | 24.7 | NS |
| range | | 17.4-43.6 | 15.6-66.6 | 15.6-66.6 | 18.0-33.6 | |
| Smoking, | ND | 8 | 18 | 9 | 5 | NS |
| yes (n %) | | 7.8% | 29.5% | 24.3% | 26.3% | |
| SES-CD | ND | ND | 4 | 2 | 1 | NS |
| 0-1 (n %) | | | | 5.4% | 5.3% | |
| HBI 0-4 (n | ND | ND | 29 | 19 | 10 | NS |
| %) | | | | 51.4% | 52.6 | |
| Montreal A1 | ND | ND | 10 | 5 | 4 | NS |
| (n %) | | | 16.4% | 13.5% | 21.1% | |
| Montreal B4 | ND | ND | 5 | 3 | 0 | 0.0026 |
| (n %) | | | 8.2% | 8.1% | 0% | |

Not determined (ND); Not significant, p > 0.05 (NS)

Statistical Analysis

Statistical variance between patient demographics and pathological parameters of patients in the B1 and B2 Montreal classification was determined by Fischer's Exact test.

Evaluation of plasma CTX-III or net fibrolysis (log(CTX-III/PRO-C3)) between healthy donors and patients diagnosed with either CD or ulcerative colitis (UC) was done by applying t-test or one-way ANOVA dependent on the number of comparing groups. Statistical difference was calculated by Kruskal-Wallis for non-parametric one-way ANOVA and either Mann-Whitney or unpaired t-test for non-parametric and parametric data. A p value below 0.05 was determined as being statistically significant.

Results

Patient Demographics and Pathological Evaluation

There were statistical higher number of patients in the B1 group compared to the number of patients in B2 (p=0.008). The age of patients with B1 were significantly younger than patients with a B2 classification (p=0.0118). Furthermore, patients with a B1 classification had a significant higher number of patients who also presented with perianal manifestations (B4) compared to patients with B2 (p=0.0026). No significant difference was demonstrated between the remaining demographics and pathological parameters.

Plasma CTX-III is Increased in Patients with Chronic Intestinal Inflammation

CD-, and UC-patients demonstrated significantly higher levels of plasma CTX-III compared to the healthy donors (p<0.0001). No statistical difference was found between patients of CD and UC (FIG. 13).

Differentiation of Luminal and Stricturing Disease Manifestations by Quantification of Plasma CTX-III Plasma CTX-III was significantly elevated in CD patients presenting with an inactive disease and a non-stricturing and non-penetrating disease (B1) behaviour. The levels were elevated compared to patients with stricturing disease (B2) manifestations ($p<0.01$) (FIG. 14A). Additionally, by calculating net cross-linked fibrolysis (log (CTX-III/PC3X)) or net fibrolysis (log (CTX-III/PRO-C3)) non-stricturing and non-penetrating disease (B1) patients demonstrated higher levels of fibrolysis when compared to patients with stricturing disease (B2) ($p<0.05$, and $p<0.01$) (FIG. 14B+FIG. 14C).

Discussion

In this study the degree of fibrolysis in IBD patients was investigated by quantifying levels of protease degraded metabolites of cross-linked type III collagen (CTX-III) as well as the net cross-linked fibrolysis either by the CTX-III/PC3X ratio or net fibrolysis by the CTX-III/PRO-C3 ratio. The main findings in this study were as follows: 1) CTX-III biomarker levels were significantly elevated in IBD patients when compared to the healthy donors (FIG. 13), and 2) Quantifying CTX-III or levels of cross-linked or non-cross-linked net fibrolysis (log (CTX-III/PC3X or PRO-C3)) could differentiate patients in clinical remission presenting with a luminal or structuring disease behaviour (FIGS. 14A-14C The characteristic chronic inflammation of IBD maintaining activation of pathological wound healing is recognized as the key driver of extensive ECM remodelling. In CD patient's expression of fibrillar collagens were found significantly elevated compared to healthy individuals (70), with histological evaluation demonstrating excessive deposition in the different tissue layers of the intestines from the submucosa to the mucosa muscularis (68). Furthermore, both inflammatory cells and activated fibroblast cells produce increased amounts of MMPs resulting in increased collagen degradation, which in severe cases can result in the formation of fistulas.

Earlier studies by Haaften et al. (71) demonstrated the use of type III collagen biomarkers reflecting MMP mediated degradation and formation in differentiating CD patients based on endoscopic evaluation of disease behaviours. Patients with stricturing disease were associated with increased levels of the collagen formation markers reflecting the excessive deposition of collagens within the tissue, whereas collagen degradation was increased in patients with penetrating disease (71).

Here, increased levels of fibrolysis are demonstrated by quantifying proteolytic metabolites of cross-linked type III collagen and assessing the overall net fibrolysis in CD patients with an inactive disease presenting with a non-stricturing and non-penetrating disease behaviour (B1). These patients could be considered to present a less severe disease manifestation compared to patients with a stricturing disease (B2), and combined with an inactive disease, suggest a low degree of active inflammation as well. Enzymatic formation of intra- and inter-molecular cross-links of the fibrillar collagens deposited in the interstitial matrix of CD patients, represents the final step in collagen maturation. Thus, proteolytic degradation of cross-linked type III collagen would be associated with fibrolysis of the mature collagen fibrils. Patients with stricturing disease present with a high amount of collagen formation causing stricture formation, which combined with extensive collagen cross-linking could inhibit proteolytic degradation. This would be observed as the decreased levels of fibrolysis demonstrated in the current study. Therefore, patients with a non-stricturing and non-penetrating disease in which type III collagen deposition is increased though potentially cross-linked to a lesser extent, degradation and clearance of pathological type III collagen deposition is increased. These differences in the molecular processes of type III collagen remodelling between a non-stricturing and non-penetrating and a stricturing disease can thus be quantified by utilization of the CTX-III biomarker, and the ratio with either PC3X or PRO-C3 for net fibrolysis.

With the limitations of endoscopy and histological evaluation of intestinal fibrosis, inclusion of biomarkers such as CTX-III reflecting true fibrolysis, could prove beneficial in the clinical setting. By evaluating type III collagen remodelling on the molecular level by minimally invasive biomarkers, data supporting endoscopy and histology could be provided. The biomarkers could identify subclinical disease behaviours as well as providing subclinical information of treatment response. As therapeutics in fibrostenosis of CD is advancing, biomarkers such as CTX-III could be utilized for the assessment of fibrosis resolution.

Conclusion

The data presented show an increased degree of proteolytic activity releasing cross-linked metabolites of type III collagen into the circulation of IBD patients. This was demonstrated for both CD and UC patients compared to healthy individuals. Additionally, CD patients were stratified based on being in endoscopic and/or clinical remission (inactive), with subsequent stratification according to a Montreal classified non-stricturing and non-penetrating (B1) or stricturing disease (B2) behaviour. Here, patients in the B1 Montreal classification demonstrated the highest degree of fibrolysis compared to patients with a B2 classification.

EXAMPLE 6—CANCER

Methods

Assay procedures were carried out as described above. These assays include CTX-III and PRO-C3.

The cohort included 20 patients each of pancreatic-, colorectal-, kidney-, stomach-, ovarian-, breast-, bladder-, lung-, melanoma-, head and neck- and prostate-cancer. It also included 3 liver cancer patients and 33 healthy controls. All cancer samples were obtained from Proteogenex (Los Angeles, CA, USA) and the healthy controls were obtained from BioIVT (Westbury, NY, USA).

TABLE 16

Cohort demographics

| | Healthy (N = 33) | Cancer (N = 223) | Total (N = 256) | CTX-III, median (ng/mL) |
|---|---|---|---|---|
| Diagnosis | | | | |
| Healthy | 33 (100%) | 0 (0%) | 33 (12.9%) | 4.66 |
| bladder cancer | 0 (0%) | 20 (9.0%) | 20 (7.8%) | 7.17 |
| breast cancer | 0 (0%) | 20 (9.0%) | 20 (7.8%) | 8.93 |
| CRC | 0 (0%) | 20 (9.0%) | 20 (7.8%) | 7.90 |
| H&N cancer | 0 (0%) | 20 (9.0%) | 20 (7.8%) | 6.70 |
| kidney cancer | 0 (0%) | 20 (9.0%) | 20 (7.8%) | 8.18 |
| liver cancer | 0 (0%) | 3 (1.3%) | 3 (1.2%) | 11.96 |
| lung cancer | 0 (0%) | 20 (9.0%) | 20 (7.8%) | 6.62 |
| melanoma | 0 (0%) | 20 (9.0%) | 20 (7.8%) | 5.68 |
| ovarian cancer | 0 (0%) | 20 (9.0%) | 20 (7.8%) | 5.73 |

TABLE 16-continued

Cohort demographics

| | Healthy (N = 33) | Cancer (N = 223) | Total (N = 256) | CTX-III, median (ng/mL) |
|---|---|---|---|---|
| pancreatic cancer | 0 (0%) | 20 (9.0%) | 20 (7.8%) | 6.49 |
| prostate cancer | 0 (0%) | 20 (9.0%) | 20 (7.8%) | 6.48 |
| stomach cancer | 0 (0%) | 20 (9.0%) | 20 (7.8%) | 5.97 |
| Stages | | | | |
| I | 0 (0%) | 7 (3.1%) | 7 (2.7%) | |
| II | 0 (0%) | 49 (22.0%) | 49 (19.1%) | |
| III | 0 (0%) | 93 (41.7%) | 93 (36.3%) | |
| IV | 0 (0%) | 74 (33.2%) | 74 (28.9%) | |
| Missing | 33 (100%) | 0 (0%) | 33 (12.9%) | |
| Age (years) | | | | |
| Mean (SD) | 57.7 (5.69) | 59.3 (11.2) | 59.1 (10.7) | |
| Median | 57.0 49.0, | 61.0 30.0, | 60.0 30.0, | |
| Min, Max | 69.0 | 87.0 | 87.0 | |
| Missing | 0 (0%) | 1 (0.4%) | 1 (0.4%) | |
| Sex | | | | |
| Male | 21 (63.6%) | 121 (54.3%) | 142 (55.5%) | |
| Female | 12 (36.4%) | 102 (45.7%) | 114 (44.5%) | |
| Ethnicity | | | | |
| Black | 13 (39.4%) | 0 (0%) | 13 (5.1%) | |
| Caucasian | 11 (33.3%) | 223 (100%) | 234 (91.4%) | |
| Hispanic | 9 (27.3%) | 0 (0%) | 9 (3.5%) | |

CRC: Colorectal cancer
H&N: Head & neck cancer

Results

Blood Levels of Protease Degraded Fragments of Cross-Linked Type ILL Collagen in Cancer Serum CTX-III in healthy individuals and patients diagnosed with cancer revealed significantly elevated levels in seven out of twelve cancer types when comparing with healthy individuals. The biomarker levels were found elevated in bladder cancer (p<0.01), breast cancer (p<0.05), CRC (p<0.001), kidney cancer (p<0.05), lung cancer (p<0.05), pancreatic cancer (p<0.05), and stomach cancer (p<0.05).

Patients with H&N-, liver-, ovarian, prostate-cancer, and melanoma did not demonstrate significantly elevated levels of CTX-III compared to healthy individuals (p>0.05). However, median CTX-III levels of all twelve types of cancer were elevated compared to the healthy individuals, with liver cancer demonstrating the highest median level of 11.96 (Table 1).

Stage III Breast Cancer is Associated with Increased Fibrolysis

When stratifying patients with breast cancer according to cancer stage, a significantly elevated level of CTX-III in patients with stage III breast cancer compared to patients with stage II (p<0.001) was observed. Additionally, by calculating the degree of net fibrolysis utilizing the ratio of CTX-III and PRO-C3, significantly higher levels of net fibrolysis were observed in patients with stage III compared to stage II (p<0.05) (FIGS. 16A-16B).

Discussion

The investigation of the CTX-III biomarkers potential in evaluating the degree of proteolytic degradation of cross-linked type III collagen as well as the net fibrolysis in various types of cancer resulted in the following: 1) Levels of CTX-III were significantly elevated in seven out of twelve types of cancer compared to the healthy individuals, and 2) Patients with stage III breast cancer presented with higher serum CTX-III and net fibrolysis in comparison with stage II patients.

Whereas a healthy individual will experience a balanced ECM remodelling in which old collagens are degraded and replaced maintaining tissue homeostasis, this process is severely skewed in the tumor stroma. In the tumor stroma, cells such as CAFs drive the formation of an increasingly stiffer ECM through the deposition and cross-linking of mainly type I collagen but also type II, III, V, and XI. A primary cause of the increased matrix stiffness is the quantity of intra- and inter-molecular cross-links within the fibrillar collagens mediated by the enzymatic actions of LOXL(L)s and TG280.

Embedded within the CTX-III neo-epitope is a Lys suggested to be involved in LOX(L) mediated cross-linking (81), thereby allowing for specific quantification of cross-linked fragments released following proteolytic degradation of type III collagen. As such, increased release of MMPs, deposition of type III collagen and LOX(L) mediated cross-linking characterizing the tumor stroma would be indicated by increased levels of the CTX-III biomarker.

In agreement with this theory, increased levels of the CTX-III biomarker were observed in the current study in which the biomarker could differentiate between healthy individuals and cancer patients, identifying individuals with an underlying pathological degradation and cross-linking of type III collagen. However, of the twelve types of cancer investigated, H&N-, liver-, ovarian, prostate-cancer, and melanoma did not demonstrate a level of fibrolysis significantly higher than that of the healthy individuals. Though the levels in the current study were not statistically different from the CTX-III level of the healthy individuals, an increase was observed on median CTX-III of cancer patients. This indicates an overall elevated degree of proteolytic degradation of cross-linked type III collagen in these patients. The lack of statistical differentiation could be caused by a limited sample size, which is especially true observing the liver cancer patients consisting of only three patients.

Furthermore, both the CTX-III biomarker levels and the overall degree of net fibrolysis (CTX-III/PRO-C3) were elevated in the later stages of breast cancer. These data indicate the use of the CTX-III biomarker in diagnosing cancer patients, and potentially the biomarkers ability to stratify patients according to the severity of their disease. A significant differentiation was observed between stage III and stage IV breast cancer patients in terms of fibrolysis.

Targeting cross-linked collagen fragments for the assessment of pathological collagen remodelling in cancer patients was recently indicated in a study by Christina Jensen et al. Here, the researchers investigated the blood-based biomarker PC3X in a study of hepatocellular carcinoma together with the PRO-C3 biomarker 82. While PRO-C3 quantifies cross-linked and non-cross-linked N-terminal propeptides of type III collagen, reflecting type III collagen formation, the PC3X biomarker specifically targets cross-linked N-terminal propeptides. PC3X levels in hepatocellular carcinoma patients compared to PRO-C3 indicated increased levels of cross-linked type III collagen, supporting the increased quantity of collagen cross-linking in the tumor stroma.

In recent years the enzymatic cross-linking of collagens has been gaining interest within the therapeutic field of cancer83. As mentioned, enzymes such as LOX(L)s and TG2 drive the increasing quantity of cross-links, but the biochemical nature of the cross-links is also of critical importance. The enzymatic actions of especially intra- and extra-cellularly expressed lysyl hydroxylase 2 have shown to promote metastasis and reduce survival. LH2 mediates the hydroxylation of specific Lys within the collagen α-chains resulting in a higher degree of Lys hydroxylated derived cross-links. Due to the important mechanistic roles in governing matrix stiffness and thereby enhancing tumor progression, LOXL2 and LH2 has been identified as targets for future therapeutic options (84).

Thus, utilizing blood-based biomarkers specifically targeting metabolites of cross-linked collagens could provide a quantitative measure reflecting CAF activity and the enzymatic activity of cross-linking enzymes. In a clinical setting, the biomarkers could potentially be utilized for diagnostic and prognostic purposes, separating patients based on the degree of fibrolysis and identify patients in which therapeutic options targeting collagen cross-linking would be beneficial.

CONCLUSION

Proteolytic fragments of cross-linked type III collagen reflecting fibrolysis were demonstrated to be released and quantifiable in twelve types of cancer, with median levels elevated in all types of cancer compared to healthy individuals. Though elevated in cancer patients, the CTX-III levels were only found significantly elevated in seven types of cancer. Furthermore, quantification of cross-linked type III collagen fibrolysis allowed differentiation between breast cancer patients in either stage II or stage III, with elevated levels associated with late-stage breast cancer.

It can be concluded that the CTX-III biomarker can be used for the quantification of cross-linked type III collagen fragments released into the circulation following proteolytic degradation, and thereby its use in a clinical setting of cancer patients.

SUMMARY

The development and validation of a highly neo-epitope specific ELISA capable of measuring cross-linked fragments of type III collagen has been demonstrated. The assay was able to distinguish between HDs and obese patients suffering from NAFLD, HDs and patients with liver fibrosis, HDs and patients with EoE, HDs and patients with chronic intestinal disease, and HDs and cancer patients illustrating the CTX-III marker's relevance as a disease marker in pathologies with known accumulation of type III collagen and increased levels of cross-linking enzymes.

Furthermore, the CTX-III biomarker and calculation of the net fibrolysis ratio (CTX-III/PRO-C3) using the PRO-C3 biomarker demonstrated elevated levels in HCV related liver fibrosis with the ability to differentiate patients according to their spontaneous fibrotic phenotype. Calculation of net fibrolysis was also able to differentiate patients according to their disease severity in chronic intestinal diseases, in particular Crohn's disease, and cancer, such as breast cancer. Thus, the CTX-III biomarker and the related net fibrolysis ratio was not only capable of identifying patients with HCV related liver fibrosis, chronic intestinal disease or cancer but could also be applied as a prognostic biomarker potentially predicting response at screening.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

The following references are cited herein:

REFERENCES

1. Baiocchini, A. et al. Extracellular Matrix Molecular Remodeling in Human Liver Fibrosis Evolution. *PLoS One* 11, e0151736 (2016).
2. Stallmach, A., Schuppan, D., Riese, H. H., Matthes, H. & Riecken, E. O. Increased collagen type III synthesis by fibroblasts isolated from strictures of patients with Crohn's disease. *Gastroenterology* 102, 1920-1929 (1992).
3. Rasmussen, D. G. K. et al. Collagen turnover profiles in chronic kidney disease. *Sci. Rep.* 9, 1-11 (2019).
4. Shahzeidi, S. et al. Enhanced type III collagen gene expression during bleomycin induced lung fibrosis. *Thorax* 48, 622-8 (1993).
5. Philp, C. J. et al. Extracellular Matrix Cross-Linking Enhances Fibroblast Growth and Protects against Matrix Proteolysis in Lung Fibrosis. *Am. J. Respir. Cell Mol. Biol.* 58, 594-603 (2018).
6. Liu, F. et al. Feedback amplification of fibrosis through matrix stiffening and COX-2 suppression. *J. Cell Biol.* 190, 693-706 (2010).
7. Liu, F. et al. Mechanosignaling through YAP and TAZ drives fibroblast activation and fibrosis. *Am. J. Physiol. Lung Cell. Mol. Physiol.* 308, L344-57 (2015).
8. Huang, X. et al. Matrix stiffness-induced myofibroblast differentiation is mediated by intrinsic mechanotransduction. *Am. J. Respir. Cell Mol. Biol.* 47, 340-8 (2012).
9. Lin, Y.-C., Sung, Y. K., Jiang, X., Peters-Golden, M. & Nicolls, M. R. Simultaneously Targeting Myofibroblast Contractility and Extracellular Matrix Cross-Linking as a Therapeutic Concept in Airway Fibrosis. *Am. J. Transplant* 17, 1229-1241 (2017).
10. Eyre, D. R. & Wu, J.-J. Collagen Cross-Links. in *Topics in Current Chemistry* 247, 207-229 (2005).
11. Herchenhan, A. et al. Lysyl Oxidase Activity Is Required for Ordered Collagen Fibrillogenesis by Tendon Cells. *J. Biol. Chem.* 290, 16440-50 (2015).
12. Ida, T. et al. Extracellular matrix with defective collagen cross-linking affects the differentiation of bone cells. *PLoS One* 13, e0204306 (2018).
13. Levental, K. R. et al. Matrix crosslinking forces tumor progression by enhancing integrin signaling. *Cell* 139, 891-906 (2009).
14. Engler, A. J., Sen, S., Sweeney, H. L. & Discher, D. E. Matrix Elasticity Directs Stem Cell Lineage Specification. *Cell* 126, 677-689 (2006).
15. Collighan, R. J. & Griffin, M. Transglutaminase 2 cross-linking of matrix proteins: biological significance and medical applications. *Amino Acids* 36, 659-70 (2009).
16. Cai, L., Xiong, X., Kong, X. & Xie, J. The Role of the Lysyl Oxidases in Tissue Repair and Remodeling: A Concise Review. *Tissue Eng. Regen. Med.* 14, 15-30 (2017).

17. Merkel, J. R., DiPaolo, B. R., Hallock, G. G. & Rice, D. C. Type I and type III collagen content of healing wounds in fetal and adult rats. *Proc. Soc. Exp. Biol. Med.* 187, 493-7 (1988).
18. Richeldi, L. et al. Efficacy and safety of nintedanib in idiopathic pulmonary fibrosis. *N. Engl. J. Med.* 370, 2071-2082 (2014).
19. Noble, P. W. et al. Pirfenidone for idiopathic pulmonary fibrosis: analysis of pooled data from three multinational phase 3 trials. *Eur. Respir. J.* 47, 243-53 (2016).
20. Distler, O. et al. Nintedanib for Systemic Sclerosis-Associated Interstitial Lung Disease. *N. Engl. J. Med.* 380, 2518-2528 (2019).
21. Govani, S. M., Stidham, R. W. & Higgins, P. D. R. How early to take arms against a sea of troubles? The case for aggressive early therapy in Crohn's disease to prevent fibrotic intestinal strictures. *J. Crohns. Colitis* 7, 923-7 (2013).
22. Wells, A. U. et al. What's in a name? That which we call IPF, by any other name would act the same. *Eur. Respir. J.* 51, 1-12 (2018).
23. Schilter, H. et al. The lysyl oxidase like 2/3 enzymatic inhibitor, PXS-5153A, reduces crosslinks and ameliorates fibrosis. *J. Cell. Mol. Med.* 23, 1759-1770 (2019).
24. Wang, Z. et al. Cardiac fibrosis can be attenuated by blocking the activity of transglutaminase 2 using a selective small-molecule inhibitor. *Cell Death Dis.* 9, 613 (2018).
25. Holvoet, T. et al. Treatment of Intestinal Fibrosis in Experimental Inflammatory Bowel Disease by the Pleiotropic Actions of a Local Rho Kinase Inhibitor. *Gastroenterology* 153, 1054-1067 (2017).
26. Sharma, S., Khalili, K. & Nguyen, G. C. Non-invasive diagnosis of advanced fibrosis and cirrhosis. *World J. Gastroenterol.* 20, 16820-30 (2014).
27. Berchtold, L. et al. Diagnosis and assessment of renal fibrosis: the state of the art. *Swiss Med. Wkly.* 147, w14442 (2017).
28. D'Haens, G. et al. Challenges in the Pathophysiology, Diagnosis and Management of Intestinal Fibrosis in Inflammatory Bowel Disease. *Gastroenterology* (2019). doi:10.1053/j.gastro.2019.05.072
29. Meyer, K. C. Pulmonary fibrosis, part I: epidemiology, pathogenesis, and diagnosis. *Expert Rev. Respir. Med.* 11, 343-359 (2017).
30. Rosenquist, C., Qvist, P., Bjarnason, N. & Christiansen, C. Measurement of a more stable region of osteocalcin in serum by ELISA with two monoclonal antibodies. *Clin. Chem.* 41, 1439-1445 (1995).
31. Reijman, M. et al. A new marker for osteoarthritis: Cross-sectional and longitudinal approach. *Arthritis Rheum.* 50, 2471-2478 (2004).
32. Nielsen, M. J. et al. The neo-epitope specific PRO-C3 ELISA measures true formation of type III collagen associated with liver and muscle parameters. *Am. J. Transl. Res.* 5, 303-315 (2013).
33. Younossi, Z. M. et al. Global epidemiology of nonalcoholic fatty liver disease-Meta-analytic assessment of prevalence, incidence, and outcomes. *Hepatology* 64, 73-84 (2016).
34. Friedman, S. L., Neuschwander-Tetri, B. A., Rinella, M. & Sanyal, A. J. Mechanisms of NAFLD development and therapeutic strategies. *Nat. Med.* 24, 908-922 (2018).
35. Luo, Y. et al. An Evaluation of the Collagen Fragments Related to Fibrogenesis and Fibrolysis in Nonalcoholic Steatohepatitis. *Sci. Rep.* 8, 12414 (2018).
36. Dongiovanni, P. et al. Insulin resistance promotes Lysyl Oxidase Like 2 induction and fibrosis accumulation in non-alcoholic fatty liver disease. *Clin. Sci.* (*Lond*). 131, 1301-1315 (2017).
37. Weiskirchen, R., Weiskirchen, S. & Tacke, F. Organ and tissue fibrosis: Molecular signals, cellular mechanisms and translational implications. *Mol. Aspects Med.* 65, 15 (2019).
38. Sebastiani, G., Gkouvatsos, K. & Pantopoulos, K. Chronic hepatitis C and liver fibrosis. *World J. GastroenteroL* 20, 11033-53 (2014).
39. Klingberg, F., Hinz, B. & White, E. S. The myofibroblast matrix: implications for tissue repair and fibrosis. *J. Pathol.* 229, 298-309 (2013).
40. Nielsen, M. J. et al. Plasma Pro-C3 (N-terminal type III collagen propeptide) predicts fibrosis progression in patients with chronic hepatitis C. *Liver Int.* 35, 429-437 (2015).
41. Hansen, J. F. et al. PRO-C3: a new and more precise collagen marker for liver fibrosis in patients with chronic hepatitis C. *Scand. J. GastroenteroL* 53, 83-87 (2018).
42. Schilter, H. et al. The lysyl oxidase like 2/3 enzymatic inhibitor, PXS-5153A, reduces crosslinks and ameliorates fibrosis. *J. Cell. Mol. Med.* 23, 1759-1770 (2019).
43. Karsdal, M. A. et al. Fibrogenesis assessed by serological type III collagen formation identifies patients with progressive liver fibrosis and responders to a potential antifibrotic therapy. *Am. J. Physiol.—Gastrointest. Liver Physiol.* 311, G1009—G1017 (2016).
44. Karsdal, M. A. et al. Assessment of liver fibrosis progression and regression by a serological collagen turnover profile. *Am. J. Physiol. Gastrointest. Liver Physiol.* 316, G25—G31 (2019).
45. Kabat, E. A., T. T. Wu, H. M. Perry, K. S. Gottesman and C. Foeller (1987), Sequences of Proteins of Immunological Interest, United States Department of Health and Human Services, Bethesda, Md., p. 1
46. E. Cheng, R. F. Souza, S. J. Spechler, Tissue remodeling in eosinophilic esophagitis., Am. J. Physiol. Gastrointest. Liver Physiol. 303 (2012) G1175-87. https://doi.org/10.1152/ajpgi.00313.2012.
47. F. Rieder, I. Nonevski, J. Ma, Z. Ouyang, G. West, C. Protheroe, G. DePetris, A. Schirbel, J. Lapinski, J. Goldblum, T. Bonfield, R. Lopez, K. Harnett, J. Lee, I. Hirano, G. Falk, P. Biancani, C. Fiocchi, T-helper 2 cytokines, transforming growth factor β1, and eosinophil products induce fibrogenesis and alter muscle motility in patients with eosinophilic esophagitis., Gastroenterology. 146 (2014) 1266-77.e1-9. https://doi.org/10.1053/j.gastro.2014.01.051.
48. A. Mishra, M. Wang, V. R. Pemmaraju, M. H. Collins, P. C. Fulkerson, J. P. Abonia, C. Blanchard, P. E. Putnam, M. E. Rothenberg, Esophageal remodeling develops as a consequence of tissue specific IL-5-induced eosinophilia., Gastroenterology. 134 (2008) 204-14. https://doi.org/10.1053/j.gastro.2007.10.002.
49. M. H. Collins, Histopathology of eosinophilic esophagitis., Dig. Dis. 32 (2014) 68-73. https://doi.org/10.1159/000357012.
50. M. B. Single, F. J. Moawad, An Overview of the Diagnosis and Management of Eosinophilic Esophagitis., Clin. Transl. Gastroenterol. 7 (2016) e155. https://doi.org/10.1038/ctg.2016.4.
51. H. Saffari, K. A. Peterson, J. C. Fang, C. Teman, G. J. Gleich, L. F. Pease, Patchy eosinophil distributions in an esophagectomy specimen from a patient with eosinophilic esophagitis: Implications for endoscopic biopsy., J.

Allergy Clin. Immunol. 130 (2012) 798-800. https://doi.org/10.1016/j.jaci.2012.03.009.
52. J. A. Nielsen, D. J. Lager, M. Lewin, G. Rendon, C. A. Roberts, The optimal number of biopsy fragments to establish a morphologic diagnosis of eosinophilic esophagitis., Am. J. Gastroenterol. 109 (2014) 515-20. https://doi.org/10.1038/ajg.2013.463.
53. S. Ishihara, T. Shoda, N. Ishimura, S. Ohta, J. Ono, Y. Azuma, E. Okimoto, K. Izuhara, I. Nomura, K. Matsumoto, Y. Kinoshita, Serum Biomarkers for the Diagnosis of Eosinophilic Esophagitis and Eosinophilic Gastroenteritis., Intern. Med. 56 (2017) 2819-2825. https://doi.org/10.2169/internalmedicine.8763-16.
54. S. B. Min, C. M. Nylund, T. P. Baker, M. Ally, B. Reinhardt, Y.-J. Chen, L. Nazareno, F. J. Moawad, Longitudinal Evaluation of Noninvasive Biomarkers for Eosinophilic Esophagitis., J. Clin. Gastroenterol. 51 (2017) 127-135. https://doi.org/10.1097/MCG.0000000000000621.
55. W. T. van Haaften, J. H. Mortensen, M. A. Karsdal, A. C. Bay-Jensen, G. Dijkstra, P. Olinga, Misbalance in type III collagen formation/degradation as a novel serological biomarker for penetrating (Montreal B3) Crohn's disease, Aliment. Pharmacol. Ther. 46 (2017) 26-39. https://doi.org/10.1111/apt.14092.
56. W. T. van Haaften, J. H. Mortensen, A. K. Dige, H. Gronbk, C. L. Hvas, A.-C. Bay-Jensen, M. A. Karsdal, P. Olinga, T. Manon-Jensen, G. Dijkstra, Serological Biomarkers of Tissue Turnover Identify Responders to Anti-TNF Therapy in Crohn's Disease: A Pilot Study., Clin. Transl. Gastroenterol. 11 (2020) e00217. https://doi.org/10.14309/ctg.0000000000000217.
57. J. M. Colizzo, S. B. Clayton, J. E. Richter, Intrabolus pressure on high-resolution manometry distinguishes fibrostenotic and inflammatory phenotypes of eosinophilic esophagitis., Dis. Esophagus Off. J. Int. Soc. Dis. Esophagus. 29 (2016) 551-7. https://doi.org/10.1111/dote.12360.
58. D. A. Katzka, D. M. Geno, A. Ravi, T. C. Smyrk, P. Lao-Sirieix, A. Miremadi, A. Miramedi, I. Debiram, M. O'Donovan, H. Kita, G. M. Kephart, L. A. Kryzer, M. Camilleri, J. A. Alexander, R. C. Fitzgerald, Accuracy, safety, and tolerability of tissue collection by Cytosponge vs endoscopy for evaluation of eosinophilic esophagitis., Clin. Gastroenterol. Hepatol. 13 (2015) 77-83.e2. https://doi.org/10.1016/j.cgh.2014.06.026.
59. Y. Kasagi, K. Dods, J. X. Wang, P. M. Chandramouleeswaran, A. J. Benitez, F. Gambanga, J. Kluger, T. Ashorobi, J. Gross, J. W. Tobias, A. J. Klein-Szanto, J. M. Spergel, A. Cianferoni, G. W. Falk, K. A. Whelan, H. Nakagawa, A. B. Muir, Fibrostenotic eosinophilic esophagitis might reflect epithelial lysyl oxidase induction by fibroblast-derived TNF-α., J. Allergy Clin. Immunol. 144 (2019) 171-182. https://doi.org/10.1016/j.jaci.2018.10.067.
60. E. S. Dellon, H. P. Kim, S. L. W. Sperry, D. A. Rybnicek, J. T. Woosley, N. J. Shaheen, A phenotypic analysis shows that eosinophilic esophagitis is a progressive fibrostenotic disease., Gastrointest. Endosc. 79 (2014) 577-85.e4. https://doi.org/10.1016/j.gie.2013.10.027.
61. A. B. Muir, T. Brown-Whitehorn, B. Godwin, A. Cianferoni, Eosinophilic esophagitis: early diagnosis is the key., Clin. Exp. Gastroenterol. 12 (2019) 391-399. https://doi.org/10.2147/CEG.S175061.
62. J. Armbruster-Lee, C. P. Cavender, J. A. Lieberman, A. E. Samarasinghe, Understanding fibrosis in eosinophilic esophagitis: Are we there yet?, J. Leukoc. Biol. 104 (2018) 31-40. https://doi.org/10.1002/JLB.5MR1017-395R.
63. A. H. J. Naber, D. J. de Jong, Assessment of disease activity in inflammatory bowel disease; relevance for clinical trials., Neth. J. Med. 61 (2003) 105-10. http://www.ncbi.nlm.nih.gov/pubmed/12852718.
64. S. Vermeire, S. Schreiber, W. J. Sandborn, C. Dubois, P. Rutgeerts, Correlation between the Crohn's disease activity and Harvey-Bradshaw indices in assessing Crohn's disease severity., Clin. Gastroenterol. Hepatol. 8 (2010) 357-63. https://doi.org/10.1016/j.cgh.2010.01.001.
65. J. Satsangi, M. S. Silverberg, S. Vermeire, J.-F. Colombel, The Montreal classification of inflammatory bowel disease: controversies, consensus, and implications., Gut. 55 (2006) 749-53. https://doi.org/10.1136/gut.2005.082909.
66. M. F. Graham, R. F. Diegelmann, C. O. Elson, W. J. Lindblad, N. Gotschalk, S. Gay, R. Gay, Collagen content and types in the intestinal strictures of Crohn's disease., Gastroenterology. 94 (1988) 257-65. https://doi.org/10.1016/0016-5085(88)90411-8.
67. E. Shimshoni, D. Yablecovitch, L. Baram, I. Dotan, I. Sagi, ECM remodelling in IBD: Innocent bystander or partner in crime? The emerging role of extracellular molecular events in sustaining intestinal inflammation, Gut. 64 (2015) 367-372. https://doi.org/10.1136/gutjnl-2014-308048.
68. I. O. Gordon, D. Bettenworth, A. Bokemeyer, A. Srivastava, C. Rosty, G. de Hertogh, M. E. Robert, M. A. Valasek, R. Mao, S. Kurada, N. Harpaz, P. Borralho, R. K. Pai, R. K. Pai, R. Odze, R. Feakins, C. E. Parker, T. Nguyen, V. Jairath, M. E. Baker, D. H. Bruining, J. G. Fletcher, B. G. Feagan, F. Rieder, Stenosis Therapy and Anti-Fibrotic Research (STAR) Consortium, Histopathology Scoring Systems of Stenosis Associated With Small Bowel Crohn's Disease: A Systematic Review., Gastroenterology. 158 (2020) 137-150.e1. https://doi.org/10.1053/j.gastro.2019.08.033.
69. M. P. Moy, J. Sauk, M. S. Gee, The Role of MR Enterography in Assessing Crohn's Disease Activity and Treatment Response., Gastroenterol. Res. Pract. 2016 (2016) 8168695. https://doi.org/10.1155/2016/8168695.
70. C. Alexakis, J. P. Caruelle, A. Sezeur, J. Cosnes, J. P. Gendre, H. Mosnier, L. Beaugerie, D. Gallot, M. Malafosse, D. Barritault, P. Kern, Reversal of abnormal collagen production in Crohn's disease intestinal biopsies treated with regenerating agents., Gut. 53 (2004) 80-90. http://www.ncbi.nlm.nih.gov/pubmed/14684581.
71. W. T. van Haaften, J. H. Mortensen, M. A. Karsdal, A. C. Bay-Jensen, G. Dijkstra, P. Olinga, Misbalance in type III collagen formation/degradation as a novel serological biomarker for penetrating (Montreal B3) Crohn's disease, Aliment. Pharmacol. Ther. 46 (2017) 26-39. https://doi.org/10.1111/apt.14092.
72. C. Bonnans, J. Chou, Z. Werb, Remodelling the extracellular matrix in development and disease., Nat. Rev. Mol. Cell Biol. 15 (2014) 786-801. https://doi.org/10.1038/nrm3904.
73. N. I. Nissen, M. Karsdal, N. Willumsen, Collagens and Cancer associated fibroblasts in the reactive stroma and its relation to Cancer biology, J. Exp. Clin. Cancer Res. 38 (2019) 115. https://doi.org/10.1186/s13046-019-1110-6.
74. C. J. Hanley, F. Noble, M. Ward, M. Bullock, C. Drifka, M. Mellone, A. Manousopoulou, H. E. Johnston, A. Hayden, S. Thirdborough, Y. Liu, D. M. Smith, T. Mellows, W. John Kao, S. D. Garbis, A. Mirnezami, T. J.

Underwood, K. W. Eliceiri, G. J. Thomas, A subset of myofibroblastic cancer-associated fibroblasts regulate collagen fiber elongation, which is prognostic in multiple cancers, Oncotarget. 7 (2016) 6159-6174. https://doi.org/10.18632/oncotarget.6740.
75. B. Erdogan, D. J. Webb, Cancer-associated fibroblasts modulate growth factor signaling and extracellular matrix remodeling to regulate tumor metastasis, Biochem. Soc. Trans. 45 (2017) 229-236. https://doi.org/10.1042/BST20160387.
76. J. S. Park, J. H. Lee, Y. S. Lee, J. K. Kim, S. M. Dong, D. S. Yoon, Emerging role of LOXL2 in the promotion of pancreas cancer metastasis, Oncotarget. 7 (2016) 42539-42552. https://doi.org/10.18632/oncotarget.9918.
77. C. C. L. Wong, A. P. W. Tse, Y. P. Huang, Y. T. Zhu, D. K. C. Chiu, R. K. H. Lai, S. L. K. Au, A. K. L. Kai, J. M. F. Lee, L. L. Wei, F. H. C. Tsang, R. C. L. Lo, J. Shi, Y. P. Zheng, C. M. Wong, I. O. L. Ng, Lysyl oxidase-like 2 is critical to tumor microenvironment and metastatic niche formation in hepatocellular carcinoma, Hepatology. 60 (2014) 1645-1658. https://doi.org/10.1002/hep.27320.
78. S. Mariathasan, S. J. Turley, D. Nickles, A. Castiglioni, K. Yuen, Y. Wang, E. E. Kadel, H. Koeppen, J. L. Astarita, R. Cubas, S. Jhunjhunwala, R. Banchereau, Y. Yang, Y. Guan, C. Chalouni, J. Ziai, Y. Şenbabaoğlu, S. Santoro, D. Sheinson, J. Hung, J. M. Giltnane, A. A. Pierce, K. Mesh, S. Lianoglou, J. Riegler, R.A.D. Carano, P. Eriksson, M. Höglund, L. Somarriba, D. L. Halligan, M. S. Van Der Heijden, Y. Loriot, J. E. Rosenberg, L. Fong, I. Mellman, D. S. Chen, M. Green, C. Derleth, G. D. Fine, P. S. Hegde, R. Bourgon, T. Powles, TGFβ attenuates tumour response to PD-L1 blockade by contributing to exclusion of T cells, Nature. 554 (2018) 544-548. https://doi.org/10.1038/nature25501.
79. C. Jensen, D. H. Madsen, M. Hansen, H. Schmidt, I. M. Svane, M. A. Karsdal, N. Willumsen, Non-invasive biomarkers derived from the extracellular matrix associate with response to immune checkpoint blockade (anti-CTLA-4) in metastatic melanoma patients, J. Immunother. Cancer. 6 (2018) 152. https://doi.org/10.1186/s40425-018-0474-z.
80. D. Pankova, Y. Chen, M. Terajima, M. J. Schliekelman, B. N. Baird, M. Fahrenholtz, L. Sun, B. J. Gill, T. J. Vadakkan, M. P. Kim, Y.-H. Ahn, J. D. Roybal, X. Liu, E. R. Parra Cuentas, J. Rodriguez, I. I. Wistuba, C. J. Creighton, D. L. Gibbons, J. M. Hicks, M. E. Dickinson, J. L. West, K. J. Grande-Allen, S. M. Hanash, M. Yamauchi, J. M. Kurie, Cancer-Associated Fibroblasts Induce a Collagen Cross-link Switch in Tumor Stroma., Mol. Cancer Res. 14 (2016) 287-95. https://doi.org/10.1158/1541-7786.MCR-15-0307.
81. D. R. Eyre, J.-J. Wu, Collagen Cross-Links, in: Top. Curr. Chem., 2005: pp. 207-229. https://doi.org/10.1007/b103828.
82. C. Jensen, S. Holm Nielsen, M. Eslam, F. Genovese, M. J. Nielsen, R. Vongsuvanh, R. Uchila, D. van der Poorten, J. George, M. A. Karsdal, D. J. Leeming, N. Willumsen, Cross-Linked Multimeric Pro-Peptides of Type III Collagen (PC3X) in Hepatocellular Carcinoma—A Biomarker That Provides Additional Prognostic Value in AFP Positive Patients., J. Hepatocell. Carcinoma. 7 (2020) 301-313. https://doi.org/10.2147/JHC.S275008.
83. S. Ferreira, N. Saraiva, P. Rijo, A.S. Fernandes, LOXL2 Inhibitors and Breast Cancer Progression., Antioxidants (Basel, Switzerland). 10 (2021). https://doi.org/10.3390/antiox10020312.
84. Y. Qi, R. Xu, Roles of PLODs in Collagen Synthesis and Cancer Progression., Front. Cell Dev. Biol. 6 (2018) 66. https://doi.org/10.3389/fcell.2018.00066.

The invention claimed is:

1. A monoclonal antibody that specifically recognises and binds to a peptide having the C-terminus amino acid sequence KAGGFAPYYG (SEQ ID NO: 1), wherein the monoclonal antibody comprises complementarity determining regions (CDRs):

CDR-L1: (SEQ ID NO: 6)
RSSKSLLHSNGNTYLY,

CDR-L2: (SEQ ID NO: 7)
RMSNLAS,

CDR-L3 (SEQ ID NO: 8)
MQHLEFPLT,

CDR-H1: (SEQ ID NO: 9)
DHGMH,

CDR-H2: (SEQ ID NO: 10)
VISTYYGDATYNQKFKG, and

CDR-H3 (SEQ ID NO: 11)
SMGGNYVGTGFAY.

2. The monoclonal antibody of claim 1, wherein the monoclonal antibody is a monoclonal antibody raised against a synthetic peptide having the C-terminus amino acid sequence KAGGFAPYYG (SEQ ID NO: 1).

3. A sandwich immunoassay for detecting in a biological sample cross-linked CT-III, said cross-linked CT-Ill comprising at least two strands of CT-Ill joined together by inter-strand cross-linking, said method comprising:

contacting said biological sample comprising said cross-linked CT-Ill with a first monoclonal antibody bound to a surface, wherein each strand of CT-Ill comprised in the cross-linked CT-Ill comprises a C-terminal neo-epitope of CT-III generated by C-protease cleavage of intact type Ill collagen;

adding a second monoclonal antibody; and determining the amount of binding of said second monoclonal antibody;

wherein both said first monoclonal antibody and said second monoclonal antibody are specifically reactive with said C-terminal neo-epitope of CT-III, said neoepitope being comprised in a C-terminal amino acid sequence KAGGFAPYYG (SEQ ID NO: 1), wherein the first and second monoclonal antibodies each comprise complementarity-determining regions (CDRs):

CDR-L1:
(SEQ ID NO: 6)
RSSKSLLHSNGNTYLY,

CDR-L2:
(SEQ ID NO: 7)
RMSNLAS,

CDR-L3:
(SEQ ID NO: 8)
MQHLEFPLT,

CDR-H1:
(SEQ ID NO: 9)
DHGMH,

CDR-H2:
(SEQ ID NO: 10)
VISTYYGDATYNQKFKG, and

CDR-H3:
(SEQ ID NO: 11)
SMGGNYVGTGFAY.

4. The sandwich immunoassay of claim 3, wherein the sandwich immunoassay is used to quantify the amount of cross-linked CT-III in a biological sample.

5. The sandwich immunoassay of claim 3, wherein the biological sample is a biofluid selected from the group consisting of serum, plasma, urine, amniotic fluid, tissue supernatant, and cell supernatant.

6. The sandwich immunoassay of claim 3, wherein the second monoclonal antibody is radiolabeled, is linked to a fluorophore or is an enzyme-linked antibody.

7. The sandwich immunoassay of claim 3, wherein a further labeled antibody which recognises the second monoclonal antibody is used to determine the amount of binding of said second monoclonal antibody.

8. The sandwich immunoassay of claim 4, further comprising correlating the quantity of cross-linked CTIII determined by said method with standard disease samples of known disease severity to evaluate the severity of a disease.

9. The sandwich immunoassay of claim 4, further comprising quantifying the amount of PRO-C3 present in the biofluid sample, determining the ratio of cross-linked type III collagen (CTX-III) to N-terminal propeptide of type III collagen (PRO-C3).

10. The sandwich immunoassay of claim 9, further comprising correlating the ratio of cross-linked type III collagen (CTX-III) to N-terminal propeptide of type III collagen (PRO-C3) determined by said method with standard disease samples of known disease severity to evaluate the severity of a disease.

11. The sandwich immunoassay of claim 8, wherein the disease is non-alcoholic fatty liver disease, an HCV related liver disease, Crohn's disease, ulcerative colitis, breast cancer, bladder cancer, colorectal cancer, head and neck cancer, kidney cancer, lung cancer, pancreatic cancer, stomach cancer, ovarian cancer, liver cancer, prostate cancer, or melanoma.

12. A method for evaluating the efficacy of an antagonist drug targeting lysyl oxidases (LOXs), wherein said method comprises using the sandwich immunoassay of claim 3 to quantify the amount of cross-linked CT-Ill in at least two biological samples, said biological samples having been obtained from a subject at a first time point and at least one subsequent time point during a period of administration of the antagonist drug to said subject, and wherein a reduction in the quantity of cross-linked CT-Ill from said first time point to said at least one subsequent time point during the period of administration of the antagonist drug is indicative of an efficacious antagonist drug targeting LOXs.

13. The method of claim 12, wherein the method evaluates the efficacy of an antagonist drug targeting LOXL2.

14. A kit for use in a sandwich assay, the kit comprising:

a solid support to which is bound the first monoclonal antibody as defined in claim 1; and the second monoclonal antibody as defined in claim 1, said second monoclonal antibody comprising a label.

15. A method of identifying a patient with a fibrotic disease, the method comprising using the sandwich immunoassay of claim 3 to quantify the amount of cross-linked CT-III in a biofluid sample obtained from the patient, and correlating said amount of cross-linked CT-III with i) values associated with known patients with the fibrotic disease and/or normal healthy controls and/or ii) a predetermined cut-off value.

16. The method of claim 15, wherein the fibrotic disease is fibrosis and the method identifies the fibrosis response phenotype of the patient, said method further comprising quantifying the amount of N-terminal propeptide of type III collagen (PRO-C3) present in the biofluid sample, determining the ratio of cross-linked type III collagen (CTX-III) to N-terminal propeptide of type III collagen (PRO-C3), and correlating said ratio of cross-linked type III collagen (CTX-III) to N-terminal propeptide of type III collagen (PRO-C3) with a predetermined cut-off value.

17. The method of claim 15, wherein the cut-off value is at least 3.8 ng/mL cross-linked CT-III and/or a ratio of cross-linked type III collagen (CTX-III) to N-terminal propeptide of type III collagen (PRO-C3) of at least 0.5.

18. The method of claim 15, wherein the fibrotic disease is eosinophilic esophagitis, a chronic intestinal disease, a cancer, or fibrosis.

19. The method of claim 15, wherein said method identifies a patient who would benefit from a treatment with a medicament which targets collagen cross-linking.

* * * * *